United States Patent
Kim et al.

(10) Patent No.: US 12,063,852 B2
(45) Date of Patent: *Aug. 13, 2024

(54) ORGANIC ELECTROLUMINESCENCE DEVICE AND MONOAMINE COMPOUND FOR ORGANIC ELECTROLUMINESCENCE DEVICE

(71) Applicant: Samsung Display Co., LTD., Yongin-si (KR)

(72) Inventors: Dongjun Kim, Suwon-si (KR); Jongwoo Kim, Hwaseong-si (KR); Eunjae Jeong, Hwaseong-si (KR); Sanghyun Han, Hwaseong-si (KR)

(73) Assignee: Samsung Display Co., Ltd., Yongin-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 18/170,157

(22) Filed: Feb. 16, 2023

(65) Prior Publication Data

US 2023/0209999 A1    Jun. 29, 2023

Related U.S. Application Data

(63) Continuation of application No. 16/745,137, filed on Jan. 16, 2020, now Pat. No. 11,600,781.

(30) Foreign Application Priority Data

Mar. 21, 2019   (KR) ........................ 10-2019-0032405

(51) Int. Cl.
| | | |
|---|---|---|
| C07D 495/04 | (2006.01) | |
| C07D 493/04 | (2006.01) | |
| H10K 85/60 | (2023.01) | |
| H10K 50/15 | (2023.01) | |
| H10K 50/17 | (2023.01) | |

(52) U.S. Cl.
CPC ......... *H10K 85/636* (2023.02); *C07D 493/04* (2013.01); *C07D 495/04* (2013.01); *H10K 50/15* (2023.02); *H10K 50/17* (2023.02); *H10K 85/6572* (2023.02); *H10K 85/6574* (2023.02); *H10K 85/6576* (2023.02)

(58) Field of Classification Search
None
See application file for complete search history.

(56) References Cited

U.S. PATENT DOCUMENTS

| | | | |
|---|---|---|---|
| 4,720,432 A | 1/1988 | VanSlyke et al. | |
| 5,061,569 A | 10/1991 | VanSlyke et al. | |
| 6,242,115 B1 | 6/2001 | Thompson et al. | |
| 8,921,832 B2 | 12/2014 | Lee et al. | |
| 10,505,121 B2 | 12/2019 | Song et al. | |
| 10,629,830 B2 | 4/2020 | Fuchiwaki et al. | |
| 11,600,781 B2 * | 3/2023 | Kim ................... | H10K 85/636 |
| 2006/0115680 A1 | 6/2006 | Hwang et al. | |
| 2013/0175507 A1 | 7/2013 | Ma | |
| 2015/0243895 A1 | 8/2015 | Lim et al. | |
| 2015/0380663 A1 | 12/2015 | Kim | |
| 2016/0099423 A1 | 4/2016 | Kim et al. | |
| 2017/0125689 A1 | 5/2017 | Lee et al. | |
| 2017/0244047 A1 | 8/2017 | Lee | |
| 2018/0053902 A1 | 2/2018 | Kim et al. | |
| 2019/0252613 A1 | 8/2019 | Song | |
| 2020/0119283 A1 | 4/2020 | Uno | |
| 2020/0172524 A1 | 6/2020 | Park et al. | |

FOREIGN PATENT DOCUMENTS

| | | |
|---|---|---|
| CN | 106749412 A | 5/2017 |
| JP | 11-144873 A | 5/1999 |
| JP | 2003-133075 A | 5/2003 |
| JP | 2004-79265 A | 3/2004 |
| JP | 2006-151979 A | 6/2006 |
| JP | 4573923 B2 | 11/2010 |
| JP | 2013-093431 A | 5/2013 |
| JP | 2014-131981 A | 7/2014 |
| KR | 10-2015-0145033 A | 12/2015 |
| KR | 10-1717551 B1 | 3/2017 |
| KR | 10-1725224 B1 | 4/2017 |
| KR | 10-2017-0126400 A | 11/2017 |
| KR | 10-1857632 B1 | 5/2018 |
| KR | 10-1872580 B1 | 6/2018 |
| KR | 10-2018-0080603 A | 7/2018 |
| KR | 10-2019-0016781 A | 2/2019 |
| KR | 10-2019-0019550 A | 2/2019 |
| WO | WO 2019/031833 A1 | 2/2019 |

OTHER PUBLICATIONS

Machine translation of CN 106749412, translation generated Apr. 2022, 20 pages. (Year: 2022).
Machine translation of JP 2013093431, translation generated Apr. 2022, 65 pages. (Year: 2022).

* cited by examiner

*Primary Examiner* — Robert S Loewe
(74) *Attorney, Agent, or Firm* — Lewis Roca Rothgerber Christie LLP

(57) ABSTRACT

An organic electroluminescence device of an embodiment includes a first electrode, a second electrode on the first electrode, and an organic layer between the first electrode and the second electrode, wherein the organic layer includes a monoamine compound including a condensed three ring hetero compound and a condensed four ring hetero compound as substituents, and wherein the condensed four ring hetero compound includes two of at least one atom of an oxygen atom or a sulfur atom.

8 Claims, 3 Drawing Sheets

ORGANIC ELECTROLUMINESCENCE DEVICE AND MONOAMINE COMPOUND FOR ORGANIC ELECTROLUMINESCENCE DEVICE

CROSS-REFERENCE TO RELATED APPLICATION

This application is a continuation of U.S. application Ser. No. 16/745,137, filed Jan. 16, 2020, which claims priority to and the benefit of Korean Patent Application No. 10-2019-0032405, filed on Mar. 21, 2019, the entire content of which is hereby incorporated by reference.

BACKGROUND

Embodiments of the present disclosure herein relate to an organic electroluminescence device and a monoamine compound for an organic electroluminescence device.

Recently, the development of an organic electroluminescence device as an image display device is being actively conducted. Different from a liquid crystal display device, the organic electroluminescence device is a self-luminescent display device in which holes and electrons injected from a first electrode and a second electrode recombine in an emission layer, and a light emission material including an organic compound in the emission layer emits light to attain display.

In the application of an organic electroluminescence device to a display device, the decrease of the driving voltage, and the increase of the emission efficiency and the life of the organic electroluminescence device are beneficial, and development on materials for an organic electroluminescence device which is capable of stably attaining the requirements is being continuously researched.

SUMMARY

Embodiments of the present disclosure provide an organic electroluminescence device and a monoamine compound for an organic electroluminescence device, and, for example, an organic electroluminescence device having high efficiency and a monoamine compound included in a hole transport region of the organic electroluminescence device.

An embodiment of the present disclosure provides an organic electroluminescence device including a first electrode, a second electrode on the first electrode, and an organic layer between the first electrode and the second electrode. The organic layer includes a monoamine compound including a condensed three ring hetero compound and a condensed four ring hetero compound as substituents. The condensed four ring hetero compound includes two of at least one atom of an oxygen atom or a sulfur atom.

In an embodiment, the condensed three ring hetero compound may include any one selected from a nitrogen atom, a sulfur atom and an oxygen atom.

In an embodiment, the hetero compounds may be each independently combined with an amine group via a linker or a direct linkage.

In an embodiment, the organic layer may include a hole transport region on the first electrode, an emission layer on the hole transport region, and an electron transport region on the emission layer. The hole transport region may include the monoamine compound.

In an embodiment, the hole transport region may include a hole injection layer on the first electrode, and a hole transport layer on the hole injection layer. The hole injection layer or the hole transport layer may include the monoamine compound.

In an embodiment, the monoamine compound may be represented by the following Formula 1:

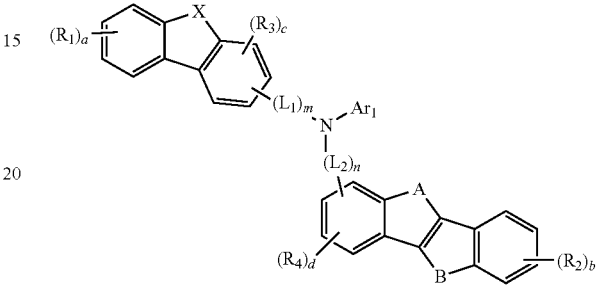

Formula 1

In Formula 1, X is $NAr_2$, S, or O, A and B are each independently O or S, $Ar_1$ and $Ar_2$ are each independently a substituted or unsubstituted aryl group of 6 to 30 carbon atoms for forming a ring, or a substituted or unsubstituted heteroaryl group of 2 to 30 carbon atoms for forming a ring, $R_1$ to $R_4$ are each independently a hydrogen atom, a deuterium atom, a halogen atom, a cyano group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, $L_1$ and $L_2$ are direct linkages, substituted or unsubstituted arylene groups of 6 to 30 carbon atoms for forming a ring, or substituted or unsubstituted heteroarylene groups of 2 to 30 carbon atoms for forming a ring, "a" and "b" are integers of 0 to 4, "c" and "d" are integers of 0 to 3, and "m" and "n" are integers of 0 to 2.

In an embodiment, Formula 1 may be represented by the following Formula 2 or Formula 3:

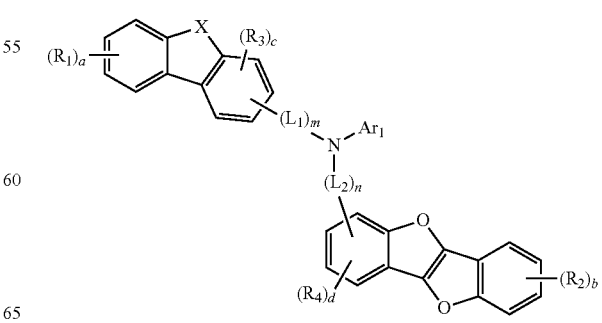

Formula 2

Formula 3

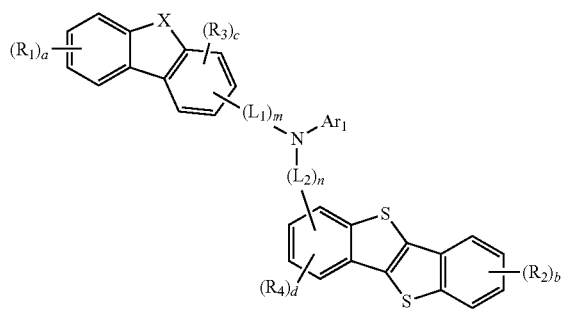

In Formula 2 and Formula 3, X, $Ar_1$, $R_1$ to $R_4$, $L_1$, $L_2$, "a" to "d", "m" and "n" are the same as defined with respect to Formula 1.

In an embodiment, Formula 1 may be represented by the following Formula 4 or Formula 5:

Formula 4

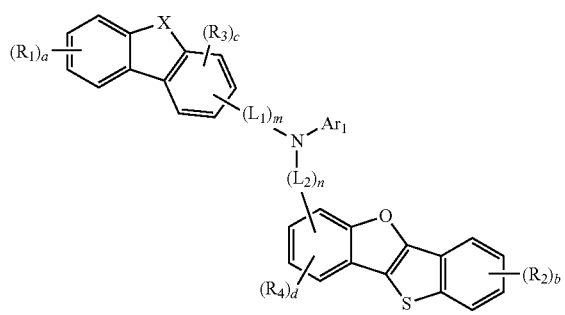

Formula 5

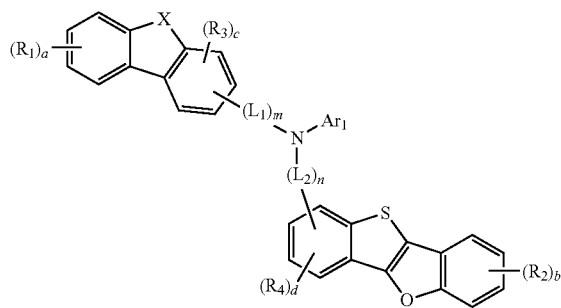

In Formula 4 and Formula 5, X, $Ar_1$, $R_1$ to $R_4$, $L_1$, $L_2$, "a" to "d", "m" and "n" are the same as defined with respect to Formula 1.

In an embodiment, "m" and "n" may be each independently 0 or 1, and $L_1$ and $L_2$ may be each independently a direct linkage or a substituted or unsubstituted arylene group of 6 to 12 carbon atoms for forming a ring.

In an embodiment, $Ar_1$ may be a substituted or unsubstituted aryl group of 6 to 18 carbon atoms for forming a ring.

In an embodiment, Formula 1 may be represented by the following Formula 6:

Formula 6

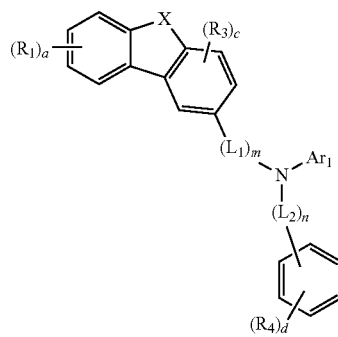

In Formula 6, X, A, B, $Ar_1$, $R_1$ to $R_4$, $L_1$, $L_2$, "a" to "d", "m" and "n" are the same as defined with respect to Formula 1.

In an embodiment of the present disclosure, there is provided an organic electroluminescence device including a first electrode, a second electrode on the first electrode, and an organic layer between the first electrode and the second electrode. The organic layer includes the monoamine compound represented by Formula 1.

In an embodiment, the organic layer may include a hole transport region on the first electrode, an emission layer on the hole transport region, and an electron transport region on the emission layer. The hole transport region may include the monoamine compound represented by Formula 1.

BRIEF DESCRIPTION OF THE FIGURES

The accompanying drawings are included to provide a further understanding of the subject matter of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Figure 1:
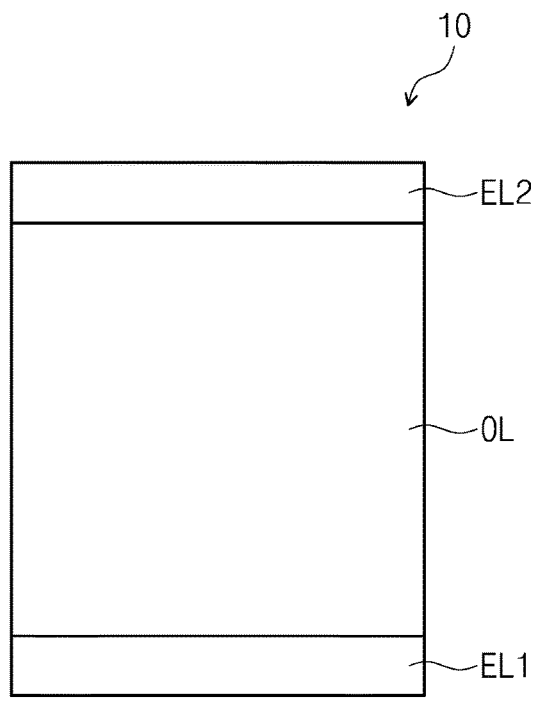
FIG. 1 is a cross-sectional view schematically illustrating an organic electroluminescence device according to an embodiment of the present disclosure.

Features of embodiments of the present disclosure will be easily understood from the description herein of embodiments of the present disclosure with reference to the accompanying drawings. The subject matter of the present disclosure may, however, be embodied in different forms and should not be construed as limited to the embodiments set forth herein. Rather, exemplary embodiments are provided so that the disclosure herein will be thorough and complete, and the spirit and scope of the present disclosure is sufficiently clear for a person skilled in the art.

Like reference numerals refer to like elements throughout. In the drawings, the dimensions of structures may be exaggerated for clarity of illustration. It will be understood that, although the terms first, second, etc. may be used herein to describe various elements, these elements should not be limited by these terms. These terms are only used to distinguish one element from another element. Thus, a first element could be termed a second element without departing from the spirit and scope of the present disclosure. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being "on" another part, it can be directly on the other part, or intervening layers may also be present. In addition, when a layer, a film, a region, a plate, etc. is referred to as being "under" another part, it can be "directly under" the other part, or intervening layers may also be present. Additionally, it will also be understood that when an element or layer is referred to as being "between" two elements or layers, it can be the only element or layer between the two elements or layers, or one or more intervening elements or layers may also be present.

First, an organic electroluminescence device according to an embodiment of the present disclosure will be explained with reference to FIGS. 1 to 4.

Figure 2:
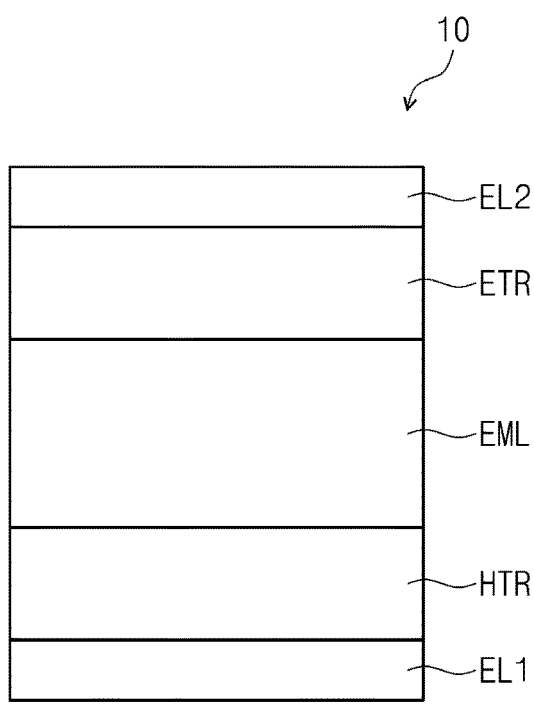
FIG. 2 is a cross-sectional view schematically illustrating an organic electroluminescence device according to an embodiment of the present disclosure.
Figure 3:
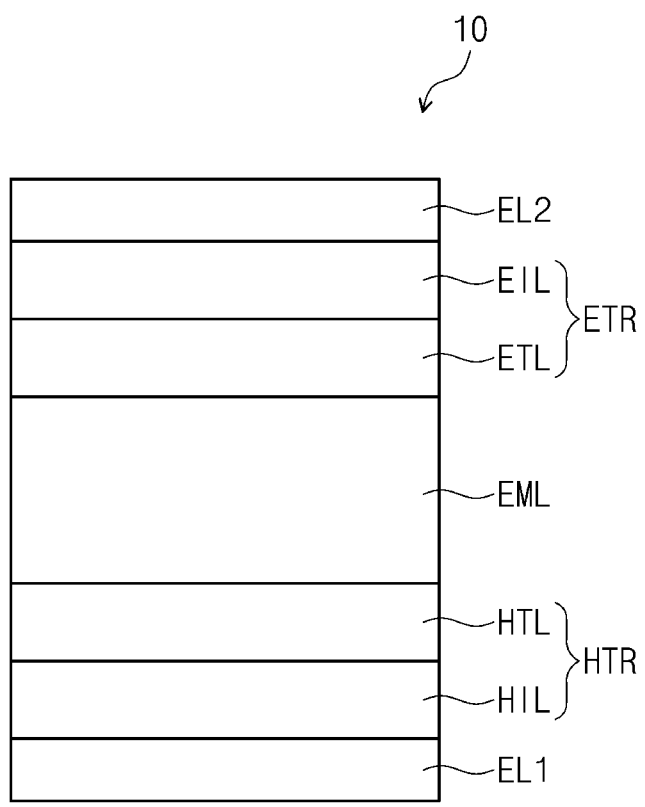
FIG. 3 is a cross-sectional view schematically illustrating an organic electroluminescence device according to an embodiment of the present disclosure.
Figure 4:
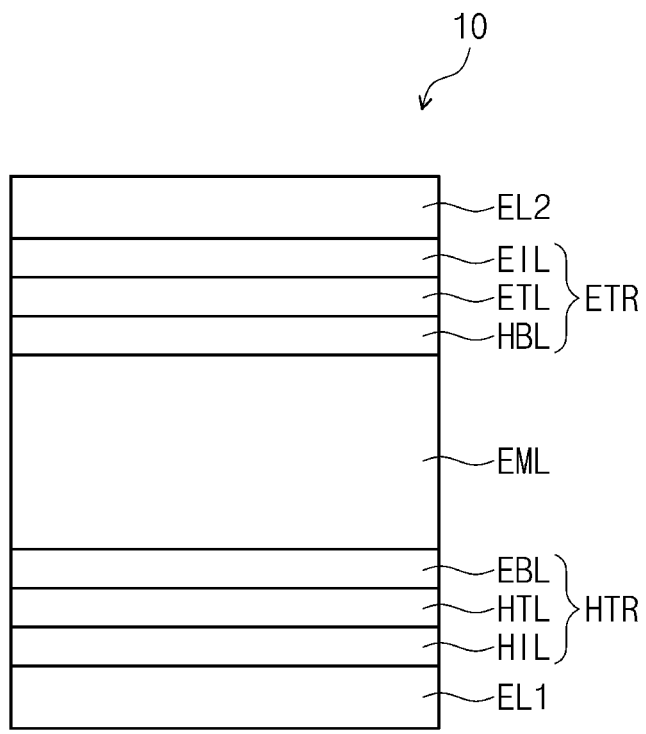
FIG. 4 is a cross-sectional view schematically illustrating an organic electroluminescence device according to an embodiment of the present disclosure.

FIG. 1 is a cross-sectional view schematically illustrating an organic electroluminescence device according to an embodiment. FIG. 2 is a cross-sectional view schematically illustrating an organic electroluminescence device according to an embodiment. FIG. 3 is a cross-sectional view schematically illustrating an organic electroluminescence device according to an embodiment. FIG. 4 is a cross-sectional view schematically illustrating an organic electroluminescence device according to an embodiment of the present disclosure.

Referring to FIG. 1, an organic electroluminescence device 10 according to an embodiment of the present disclosure includes a first electrode EL1, an organic layer OL and a second electrode EL2. The first electrode EL1 and the second electrode EL2 face each other, and the organic layer may be between the first electrode EL1 and the second electrode EL2.

When compared with FIG. 1, FIG. 2 shows the cross-sectional view of an organic electroluminescence device 10 of an embodiment, wherein the organic layer OL includes a hole transport region HTR, an emission layer EML, and an electron transport region ETR.

In addition, when compared with FIG. 2, FIG. 3 shows the cross-sectional view of an organic electroluminescence device 10 of an embodiment, wherein the hole transport region HTR includes a hole injection layer HIL and a hole transport layer HTL, and the electron transport region ETR includes an electron injection layer EIL and an electron transport layer ETL.

In addition, when compared with FIG. 2, FIG. 4 shows the cross-sectional view of an organic electroluminescence device 10 of an embodiment, wherein the hole transport region HTR includes a hole injection layer HIL, a hole transport layer HTL, and an electron blocking layer EBL, and the electron transport region ETR includes a hole blocking layer HBL, an electron transport layer ETL and an electron injection layer EIL.

The organic layer OL includes the monoamine compound according to an embodiment of the present disclosure. Hereinafter, the monoamine compound according to an embodiment of the present disclosure will be explained in more detail, and each layer of the organic electroluminescence device 10 will be explained.

As used in the present description, the term "substituted or unsubstituted" corresponds to substituted or unsubstituted with at least one substituent selected from the group consisting of a deuterium atom, a halogen atom, a cyano group, a nitro group, a silyl group, a boron group, a phosphine group, an alkyl group, an alkenyl group, an aryl group, and a heterocyclic group. In addition, each of the substituents may be substituted or unsubstituted. For example, a biphenyl group may be interpreted as an aryl group or a phenyl group substituted with a phenyl group.

In the present description, examples of the halogen atom may include a fluorine atom, a chlorine atom, a bromine atom and an iodine atom.

In the present description, the alkyl group may be a linear, branched, or cyclic type (e.g., a linear, branched, or cyclic alkyl group). The number of carbon atoms of the alkyl group may be 1 to 30, 1 to 20, 1 to 10, or 1 to 4. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

As used in the present description, the term "aryl group" refers to an optional functional group or substituent derived from an aromatic hydrocarbon ring. The aryl group may be a monocyclic aryl group or a polycyclic aryl group. The number of carbon atoms for forming a ring in the aryl group may be 6 to 30, 6 to 20, or 6 to 12. Examples of the aryl group may include phenyl, naphthyl, fluorenyl, anthracenyl, phenanthryl, biphenyl, terphenyl, quaterphenyl, quinquephenyl, sexiphenyl, biphenylene, triphenylenyl, pyrenyl, benzofluoranthenyl, chrysenyl, etc., without limitation.

In the present description, the fluorenyl group may be substituted, and two substituents may be combined with each other to form a spiro structure. Examples of the substituted fluorenyl group may include the following. However, embodiments of the present disclosure are not limited thereto.

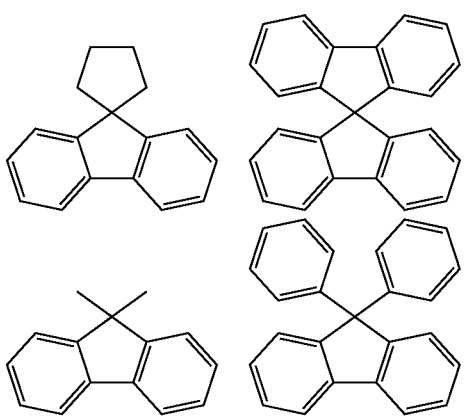

In the present description, the heteroaryl group may include one or more selected from O, N, P, Si and S as a heteroatom. In an embodiment, where the heteroaryl group includes two heteroatoms, the two heteroatoms may be the same or different. The number of carbon atoms for forming a ring of the heteroaryl group may be 2 to 30, or 5 to 12. The heteroaryl group may be monocyclic heteroaryl group or polycyclic heteroaryl group. The polycyclic heteroaryl group may have, for example, a two-ring or three-ring structure. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuranyl, etc., without limitation.

In the present description, the silyl group may include an alkyl silyl group and an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, embodiments of the present disclosure are not limited thereto.

In the present description, the explanation of the aryl group may also be applied to the arylene group except that the arylene group is a divalent group.

In the present description, the explanation on the heteroaryl group may also be applied to the heteroarylene group except that the heteroarylene group is a divalent group.

In an embodiment, the monoamine compound includes a condensed three ring hetero compound and a condensed four ring hetero compound as substituents, and the condensed four ring hetero compound includes two selected from at least one atom of an oxygen atom or a sulfur atom. For example, the condensed four ring hetero compound which is included in the monoamine compound may include two oxygen atoms. In some embodiments, the condensed four ring hetero compound which is included in the monoamine compound may include two sulfur atoms. In some embodiments, the condensed four ring hetero compound which is included in the monoamine compound may include one oxygen atom and one sulfur atom.

The condensed three ring hetero compound included in the monoamine compound may include at least one of a nitrogen atom, a sulfur atom or an oxygen atom.

In an embodiment, the condensed three ring hetero compound included in the monoamine compound may be combined with an amine group via a linker or may make a direct linkage with the amine group.

In an embodiment, the condensed four ring hetero compound included in the monoamine compound may be combined with an amine group via a linker or may make a direct linkage with the amine group.

The monoamine compound according to an embodiment is represented by the following Formula 1:

Formula 1

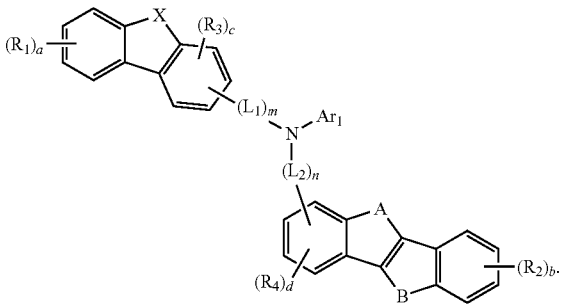

In Formula 1, X is $NAr_2$, S, or O.

In Formula 1, A and B are each independently O or S.

In Formula 1, $Ar_1$ and $Ar_2$ are each independently a substituted or unsubstituted aryl group of 6 to 30 carbon atoms for forming a ring, or a substituted or unsubstituted heteroaryl group of 2 to 30 carbon atoms for forming a ring.

In Formula 1, $R_1$ to $R_4$ are each independently a hydrogen atom, a deuterium atom, a halogen atom, a cyano group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In Formula 1, $L_1$ and $L_2$ are direct linkages, substituted or unsubstituted arylene groups of 6 to 30 carbon atoms for forming a ring, or substituted or unsubstituted heteroarylene groups of 2 to 30 carbon atoms for forming a ring.

In Formula 1, "a" and "b" are integers of 0 to 4. In some embodiments, if "a" is 2 or more, a plurality of $R_1$ groups are the same or different, and if "b" is 2 or more, a plurality of $R_2$ groups are the same or different.

In Formula 1, "c" and "d" are integers of 0 to 3. In some embodiments, if "c" is 2 or more, a plurality of $R_3$ groups are the same or different, and if "d" is 2 or more, a plurality of $R_4$ groups are the same or different.

In Formula 1, "m" and "n" are integers of 0 to 2. In some embodiments, if "m" is 2 or more, a plurality of $L_1$ groups are the same or different, and if "n" is 2 or more, a plurality of $L_2$ groups are the same or different.

In an embodiment, "m" and "n" in Formula 1 may be each independently 0, and $L_1$ and $L_2$ may be each independently a direct linkage.

In an embodiment, "m" and "n" in Formula 1 may be each independently 1, and $L_1$ and $L_2$ may be each independently a substituted or unsubstituted arylene group of 6 to 12 carbon atoms for forming a ring. $L_1$ and $L_2$, for example, may be each independently a substituted or unsubstituted phenylene group or a substituted or unsubstituted biphenylene group. However, embodiments of the present disclosure are not limited thereto.

In an embodiment, $Ar_1$ of Formula 1 may be a substituted or unsubstituted aryl group of 6 to 20 carbon atoms for forming a ring. For example, $Ar_1$ may be a substituted or unsubstituted phenyl group, a substituted or unsubstituted biphenyl group, a substituted or unsubstituted naphthyl group, or a substituted or unsubstituted fluorenyl group. However, embodiments of the present disclosure are not limited thereto.

In an embodiment, A and B in Formula 1 may be the same atom. In some embodiments, Formula 1 may be represented by the following Formula 2 or Formula 3:

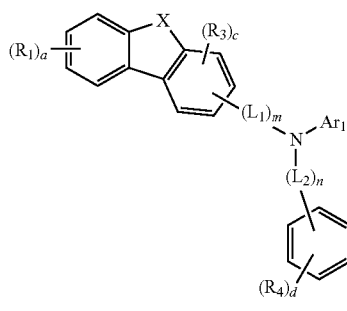

Formula 2

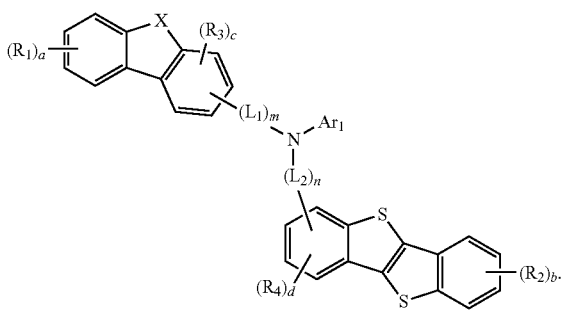

Formula 3

In Formula 2 and Formula 3, X, $Ar_1$, $R_1$ to $R_4$, $L_1$, $L_2$, "a" to "d", "m" and "n" are the same as defined with respect to Formula 1.

In an embodiment, A and B in Formula 1 may be different atoms from each other. In some embodiments, Formula 1 may be represented by the following Formula 4 or Formula 5:

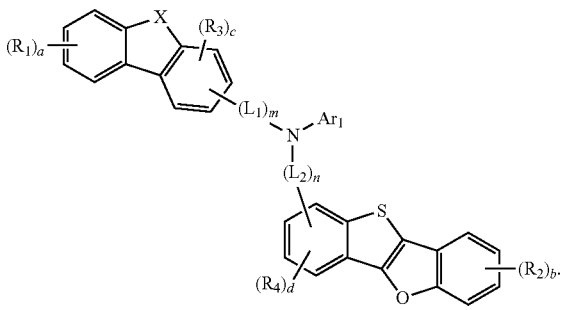

Formula 4

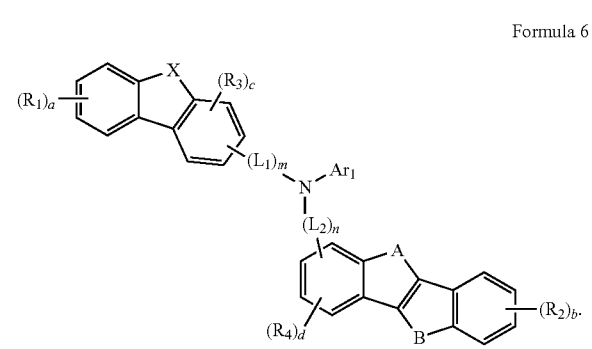

Formula 5

In Formula 4 and Formula 5, X, $Ar_1$, $R_1$ to $R_4$, $L_1$, $L_2$, "a" to "d", "m" and "n" are the same as defined with respect to Formula 1.

In an embodiment, Formula 1 may be represented by the following Formula 6:

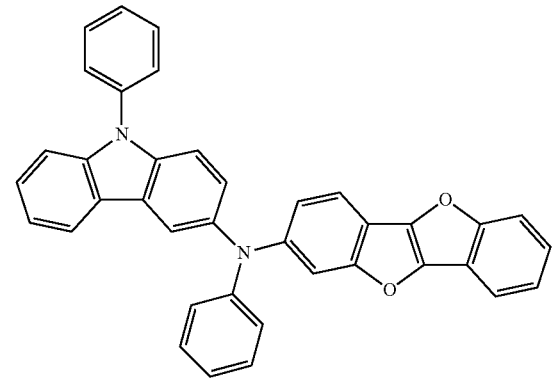

Formula 6

In Formula 6, X, A, B, $Ar_1$, $R_1$ to $R_4$, $L_1$, $L_2$, "a" to "d", "m" and "n" are the same as defined with respect to Formula 1.

The monoamine compound represented by Formula 1 according to an embodiment of the present disclosure may be at least one selected from the compounds represented in the following Compound Group 1, but embodiments of the present disclosure are not limited thereto:

Compound Group 1

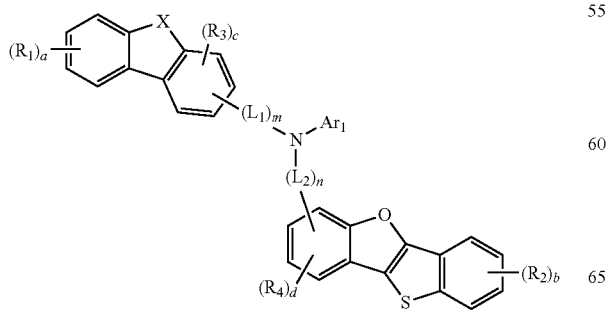

1

2
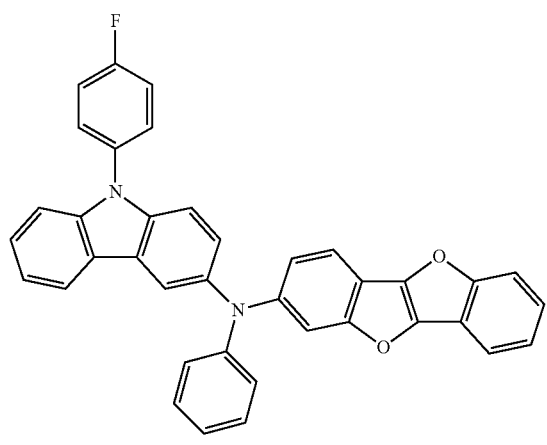
3
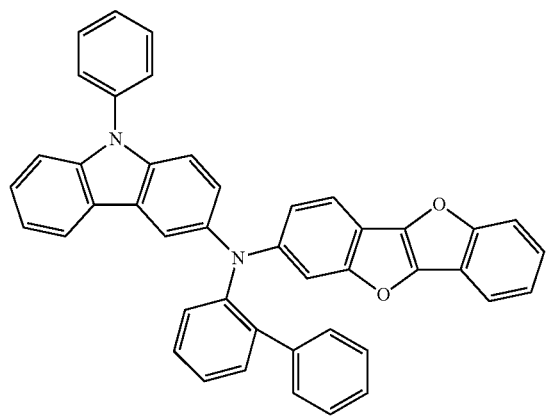
4
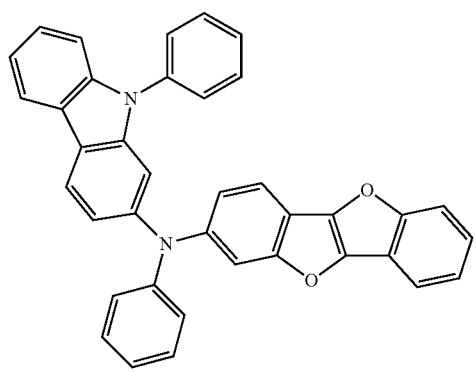
5
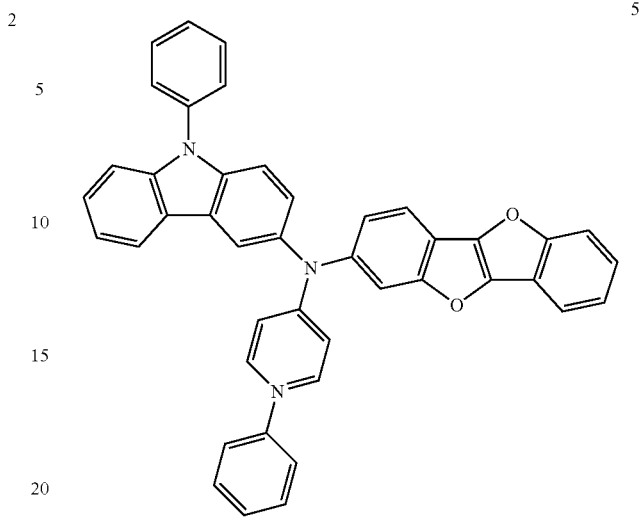
6
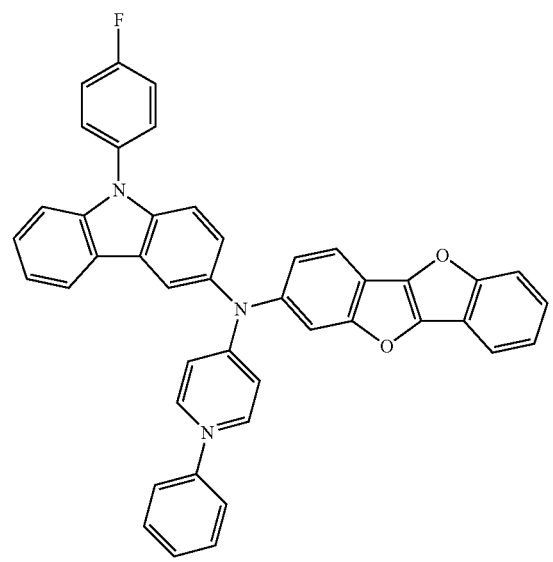
7
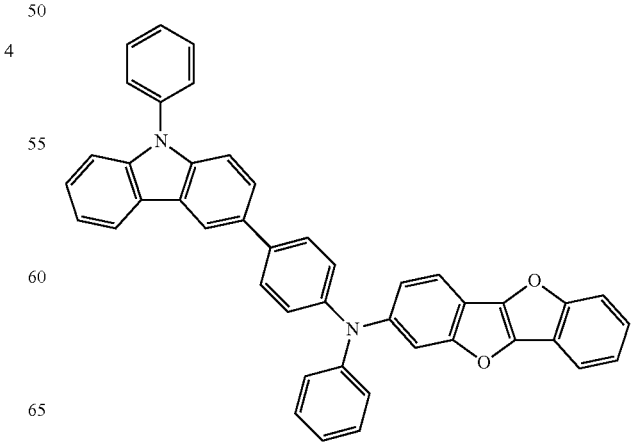

8
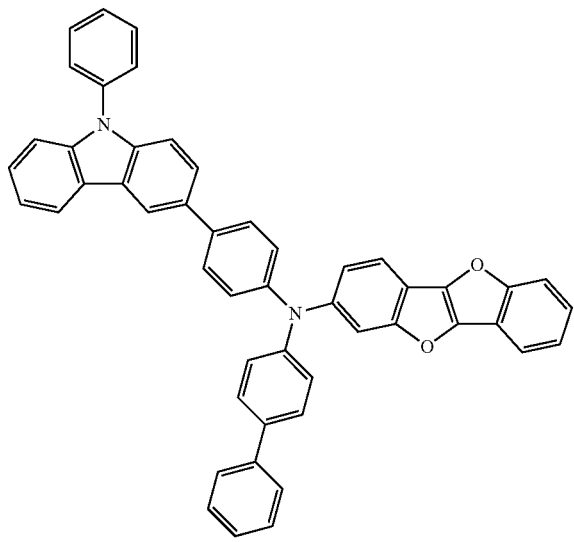
9
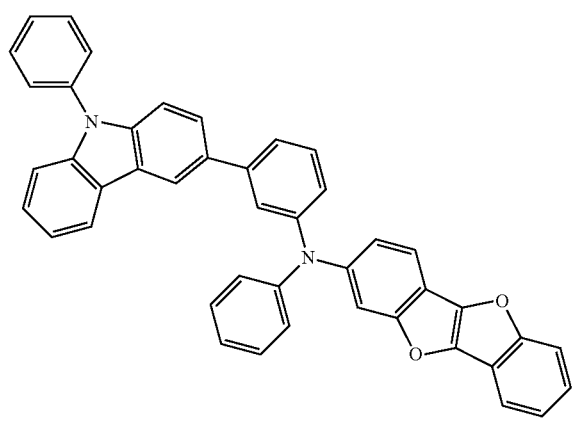
10
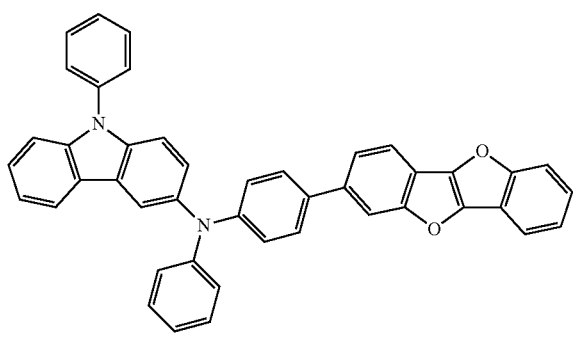
11
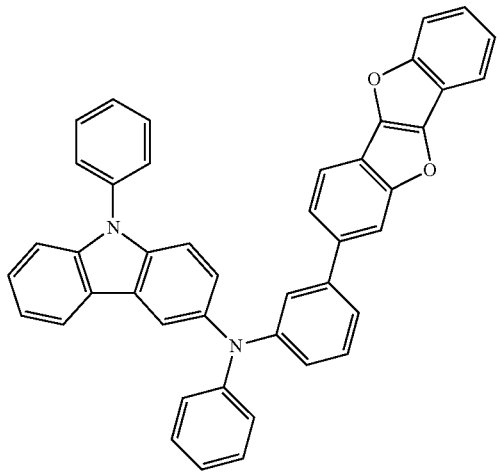
12
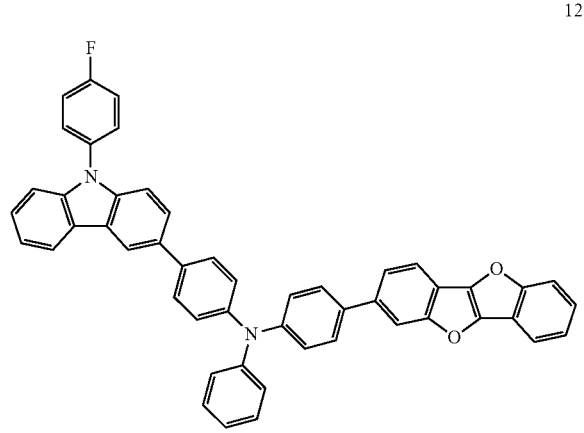 [SMILES: Fc1ccc(-n2c3ccccc3c3cc(-c4ccc(N(c5ccccc5)c5ccc(-c6ccc7c(c6)oc6c8ccccc8oc76)cc5)cc4)ccc32)cc1]
13
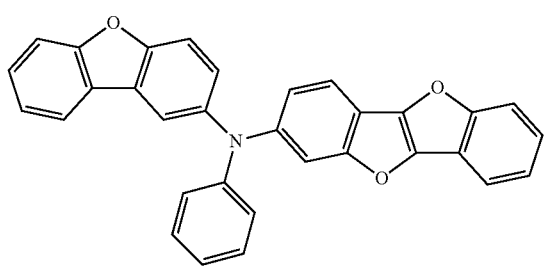
14
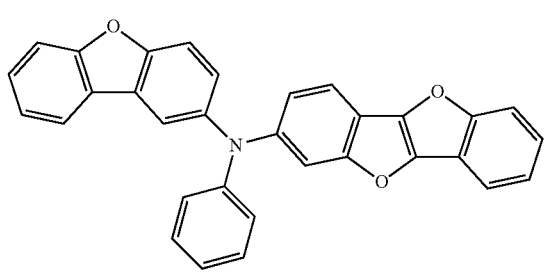

-continued
15
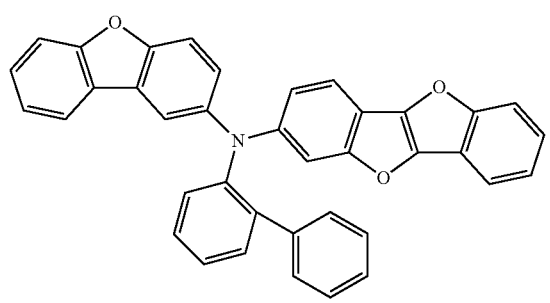
16
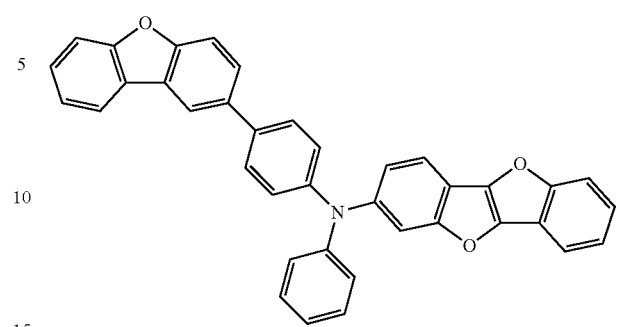
19
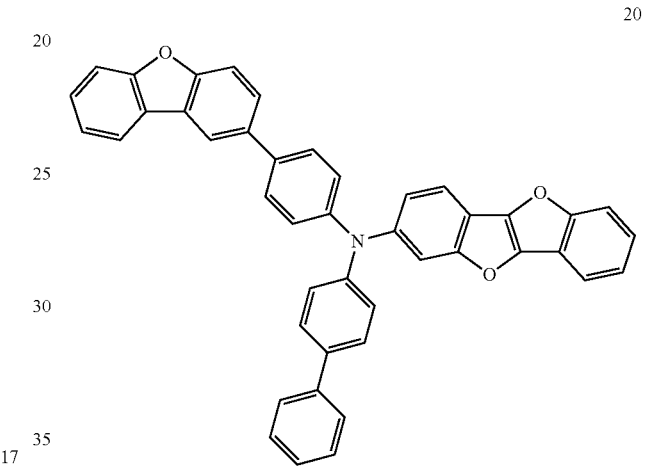
17
20
18
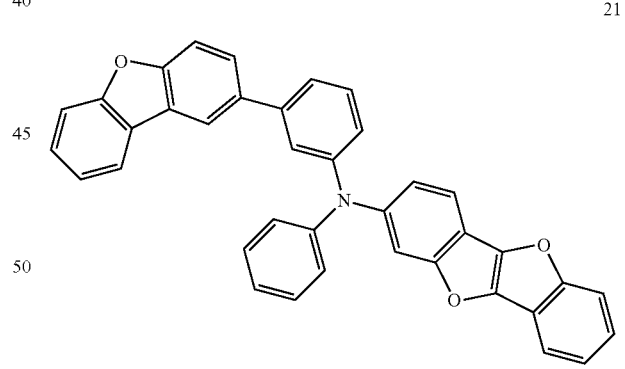
21
22
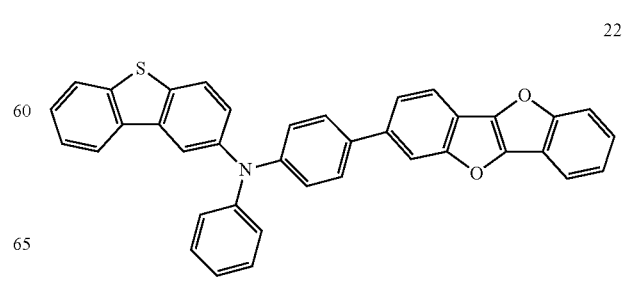

23
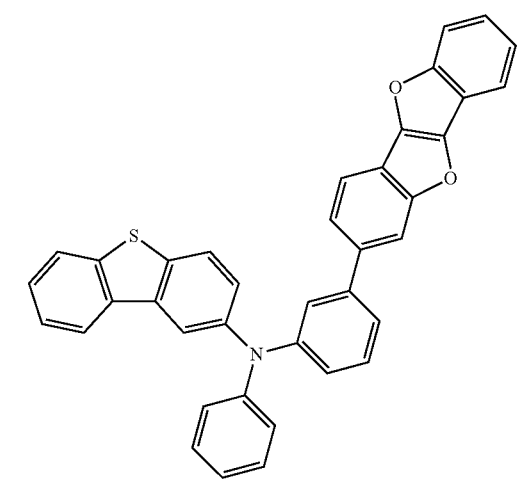
24
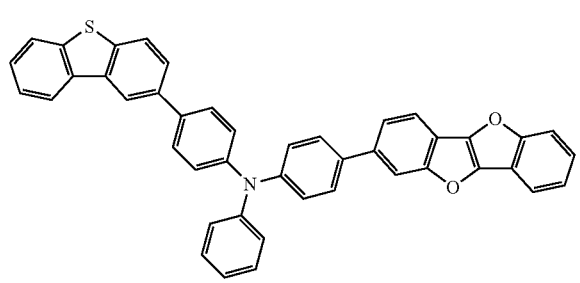
25
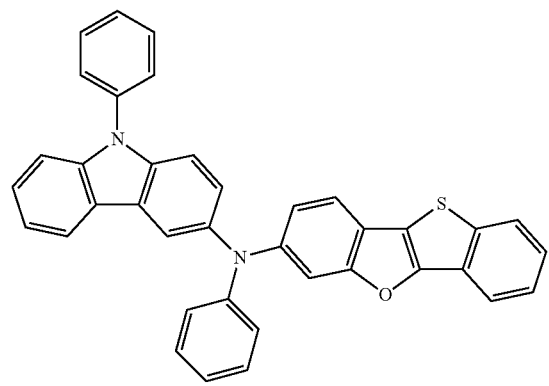
26
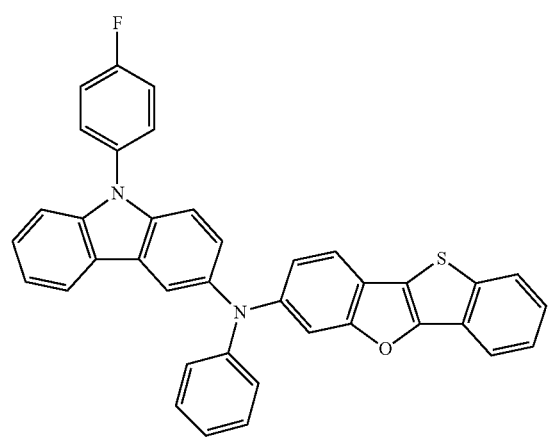
27
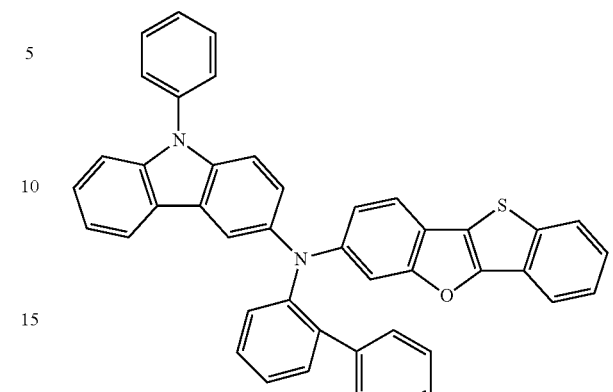
28
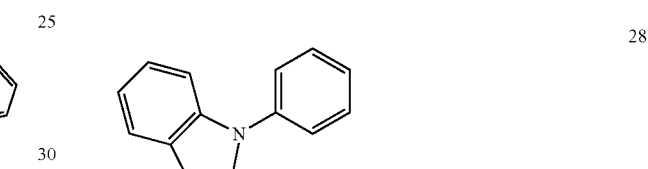
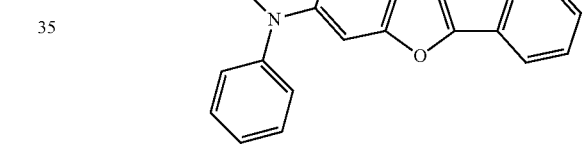
29
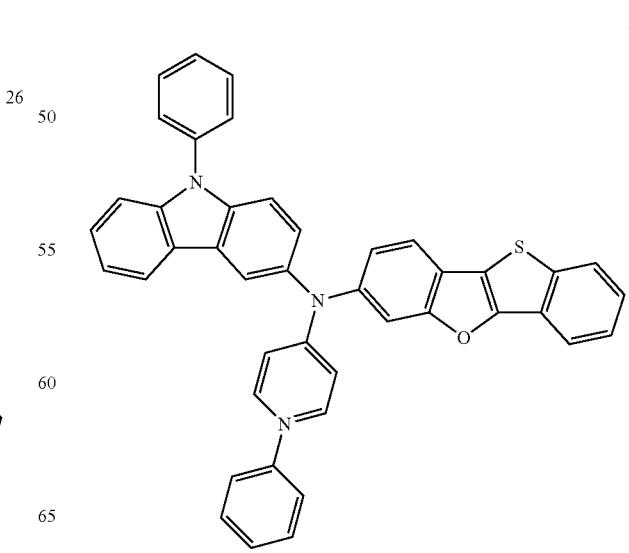

30
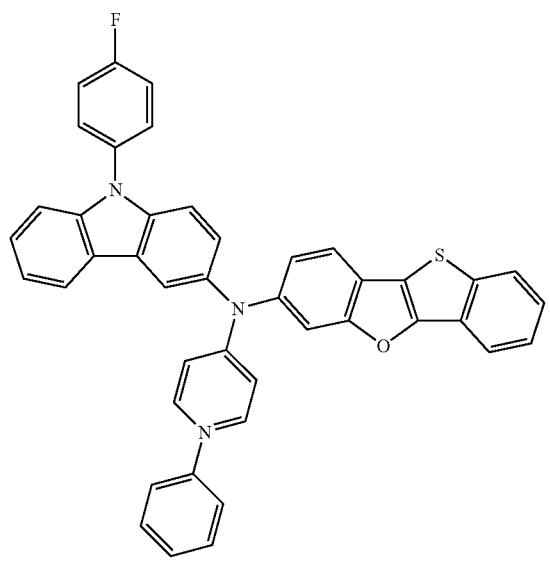
31
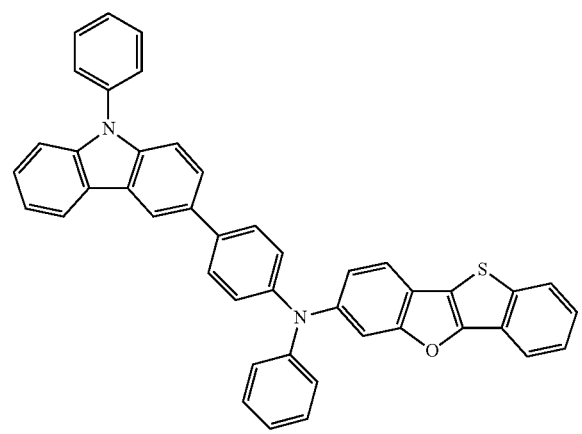
32
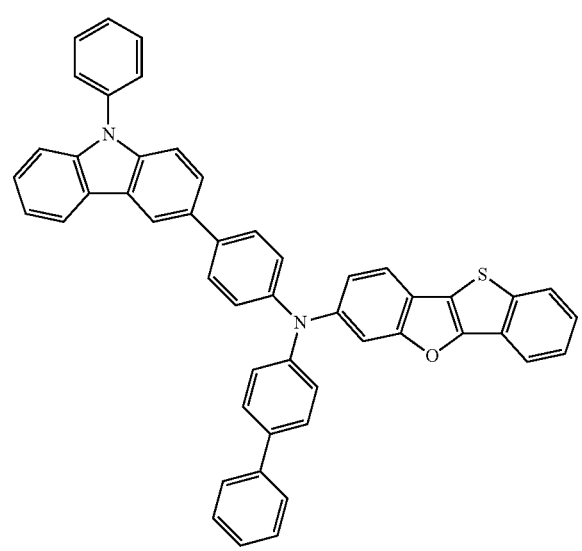
33
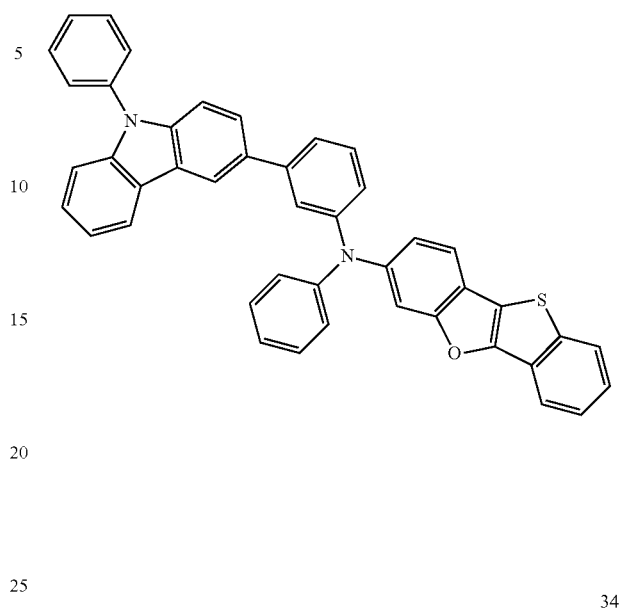
34
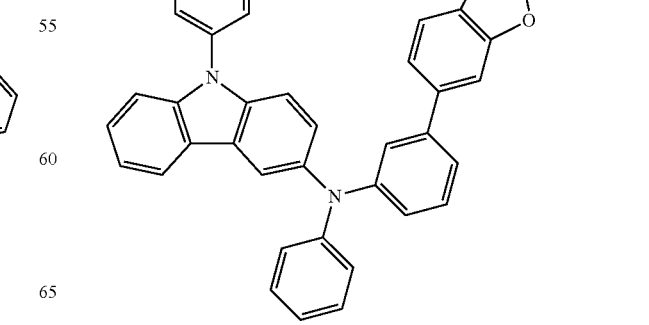
35

36
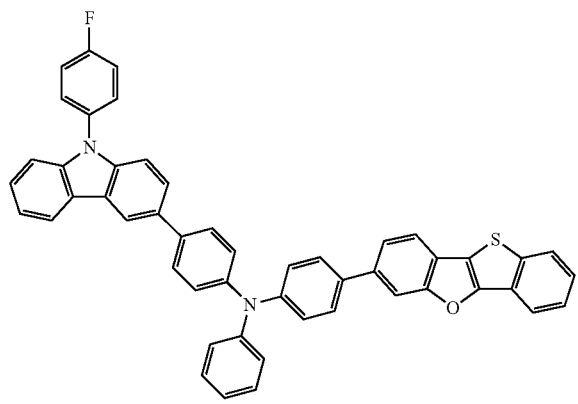
37
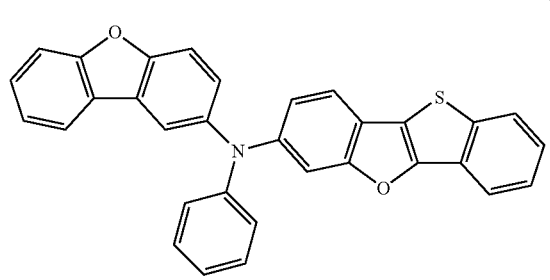
38
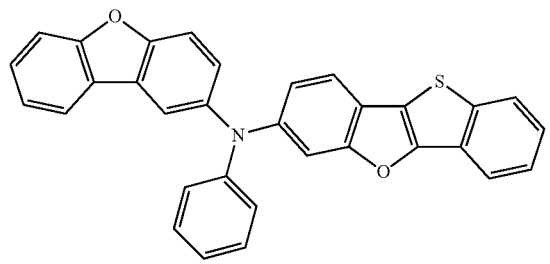
39
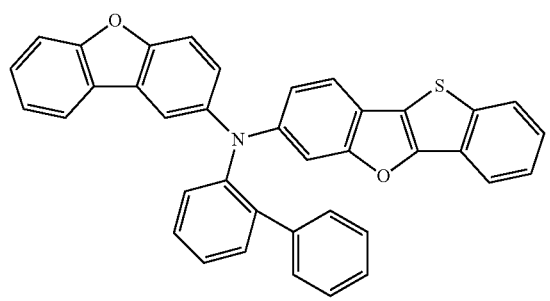
40
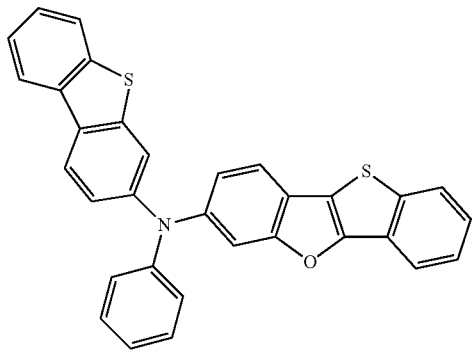
41
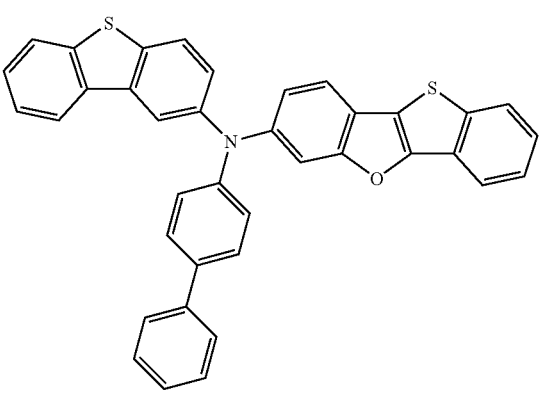
42
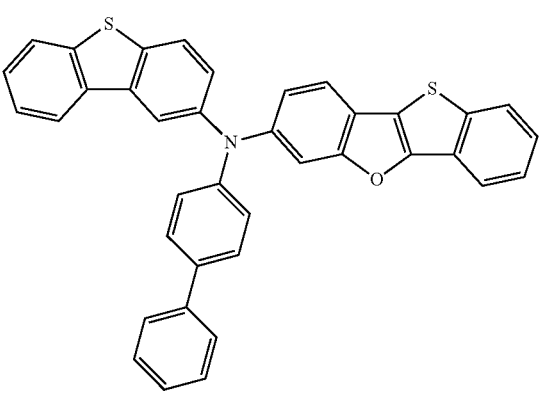
43
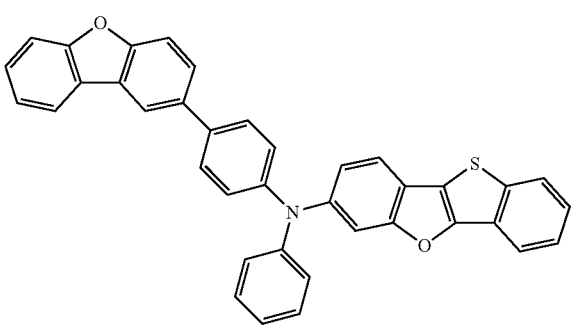

44
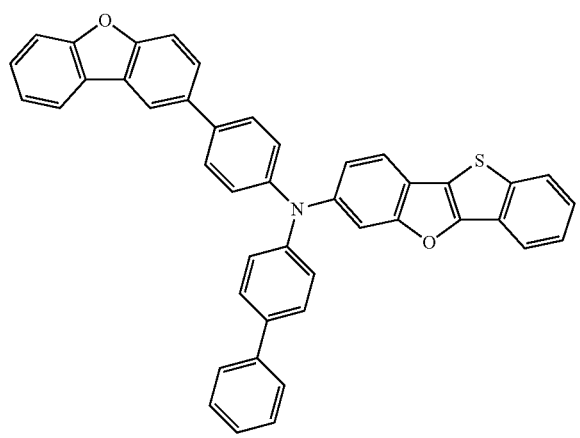
45
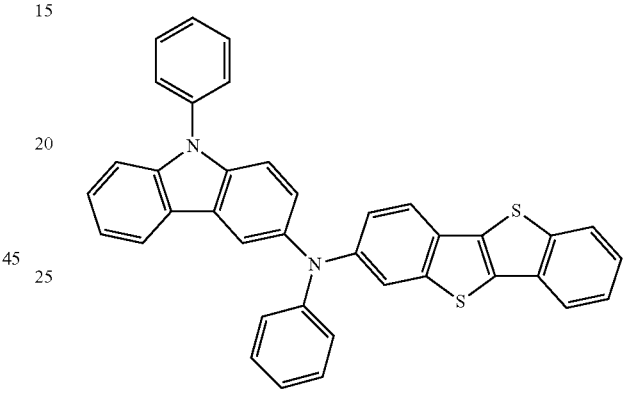
46
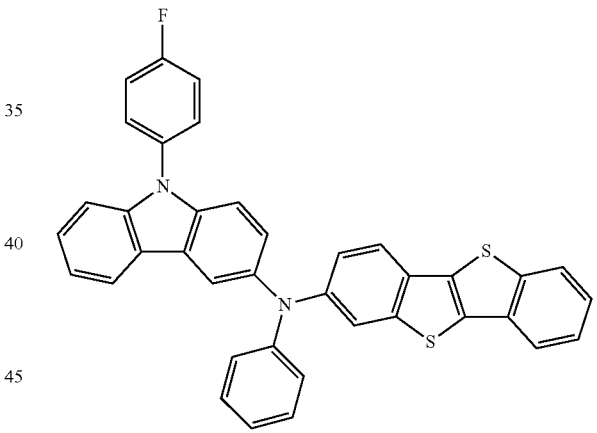
47
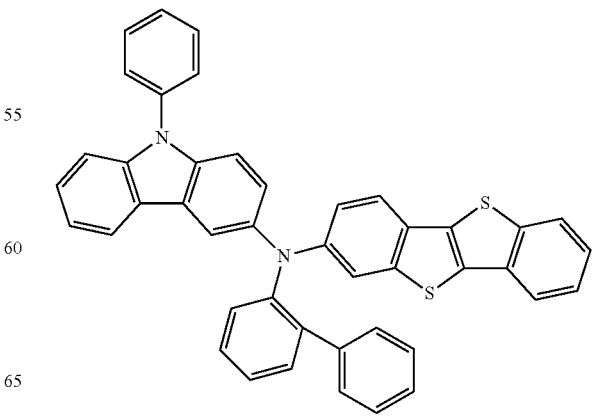
48
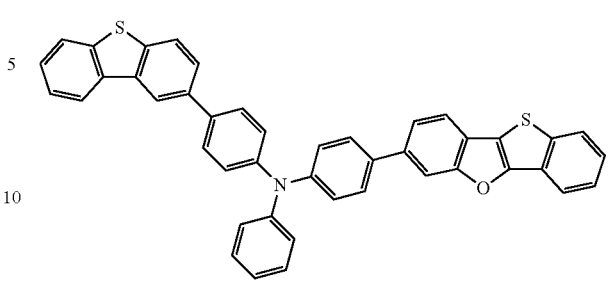
49
50
51

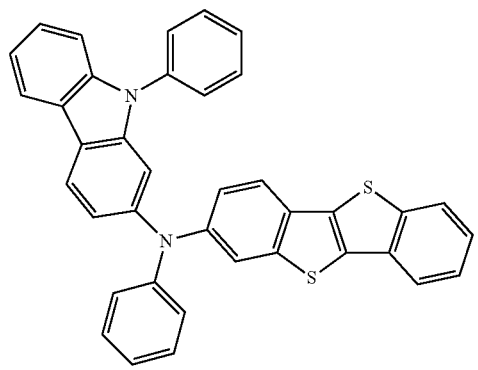
52
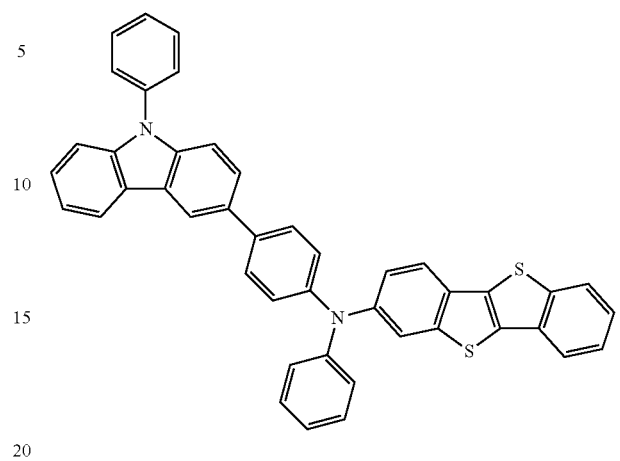
55
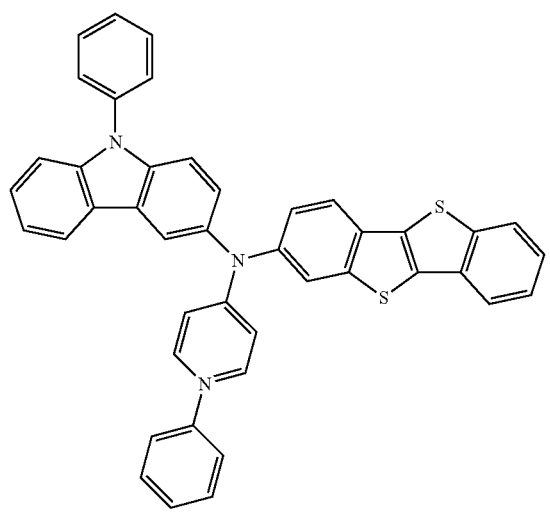
53
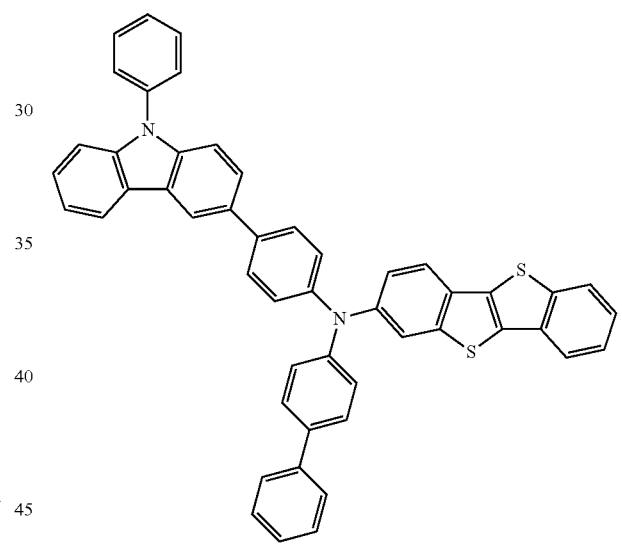
56
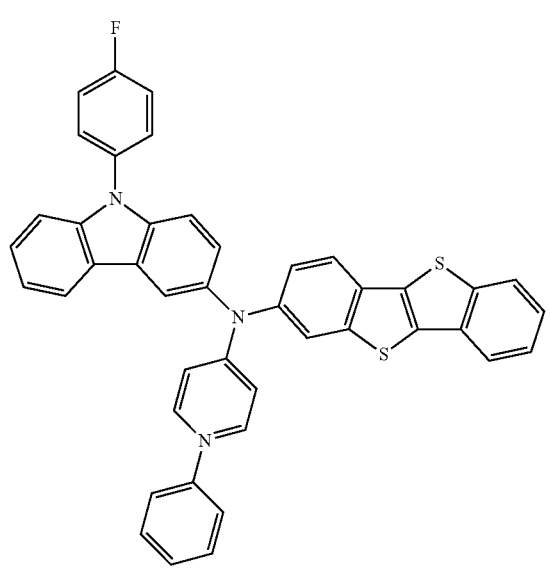
54
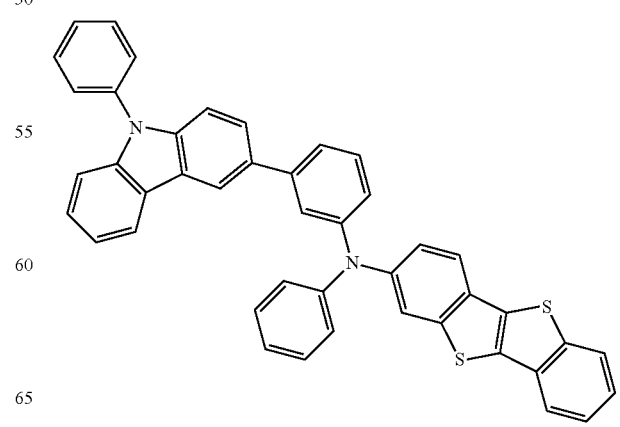
57

58
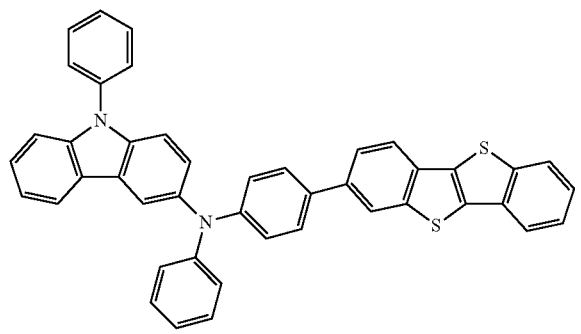
59
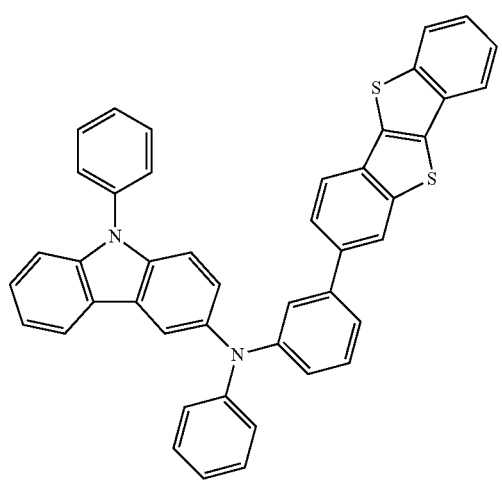
60
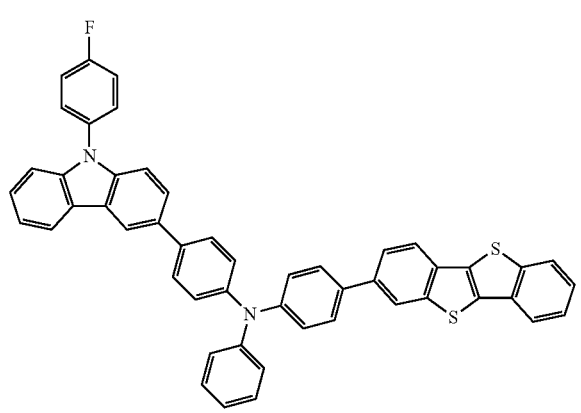
61
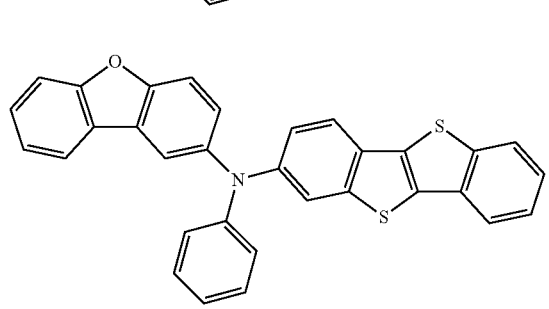
62
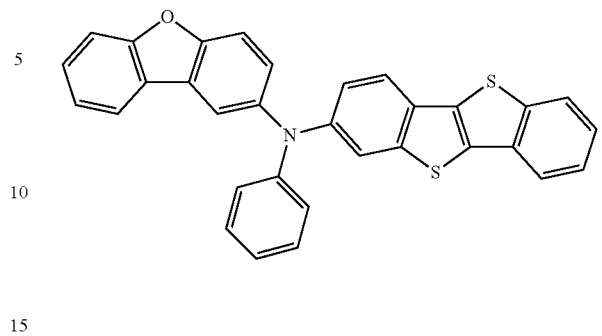
63
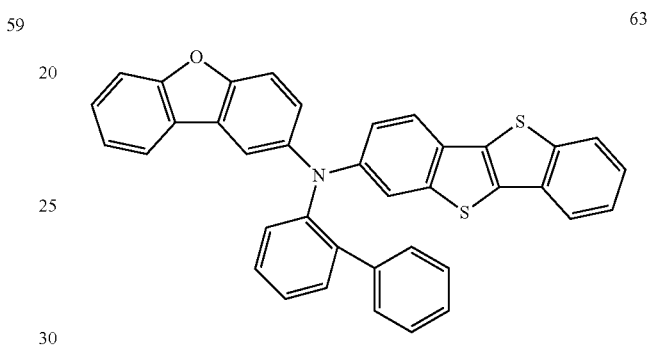
64
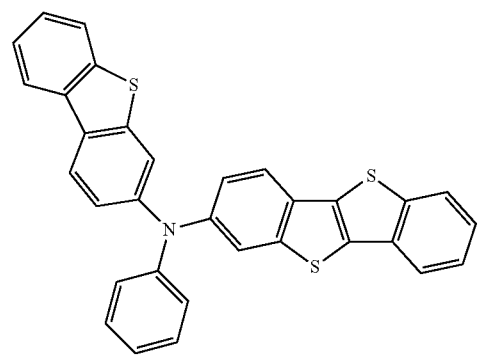
65
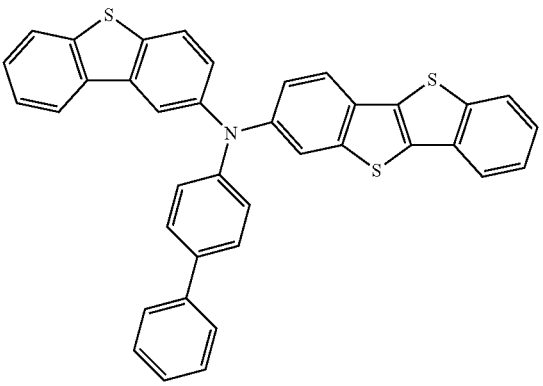

66
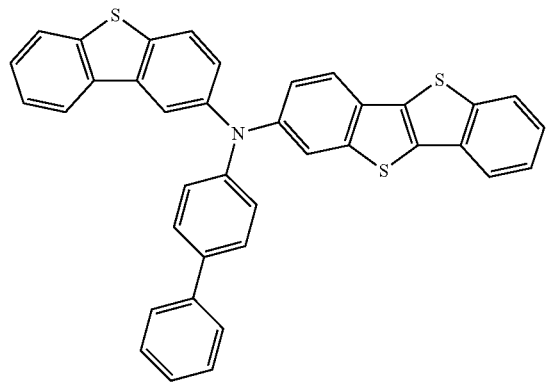
67
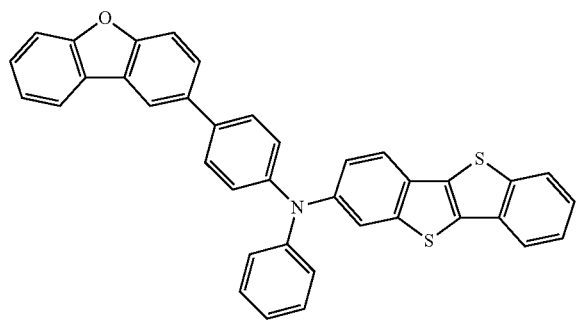
68
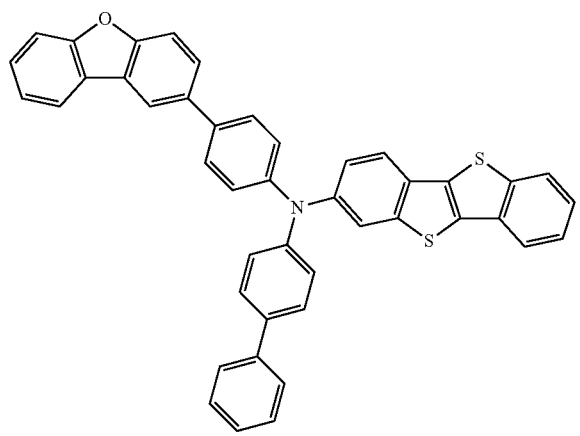
69
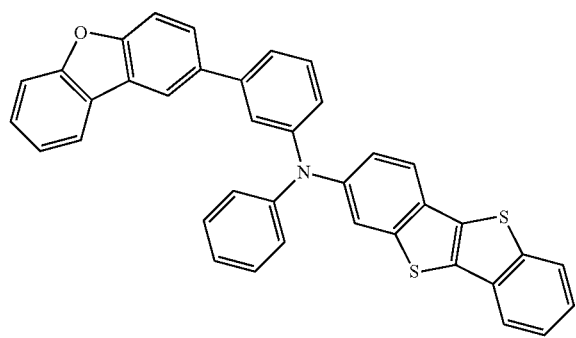
70
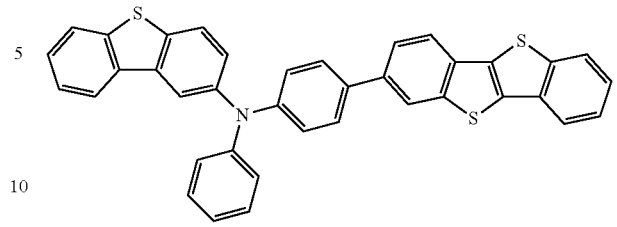
71
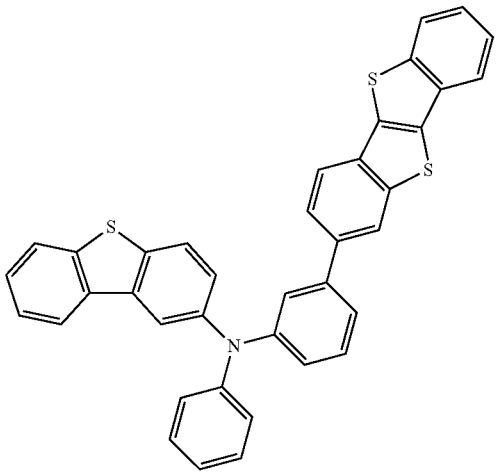
72
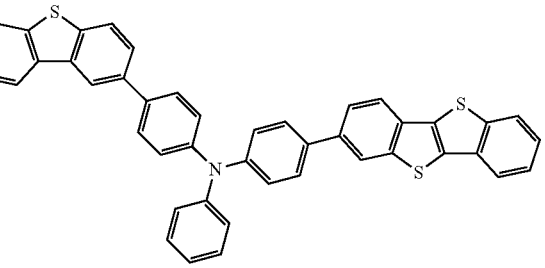
73
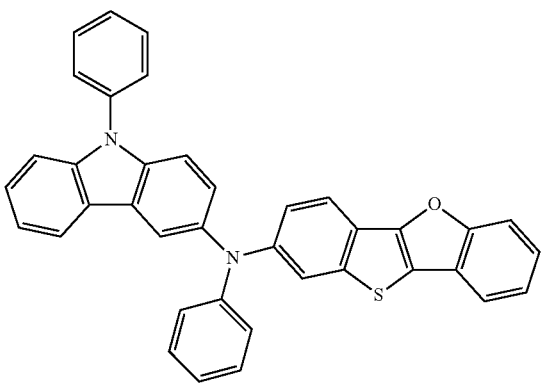

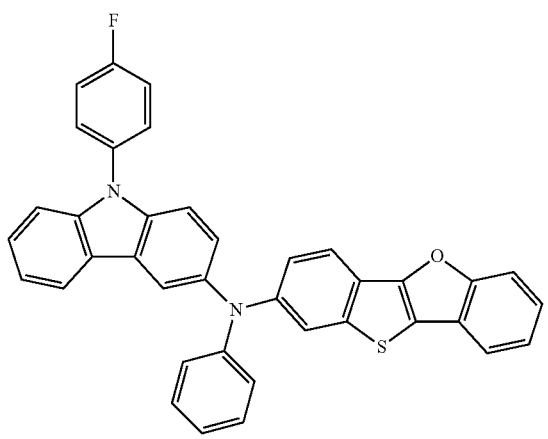
74
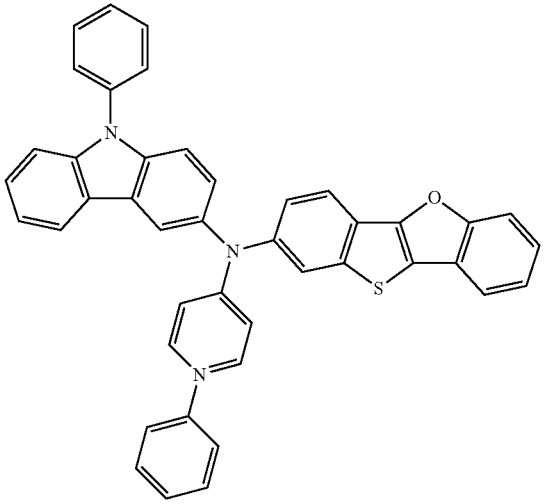
77
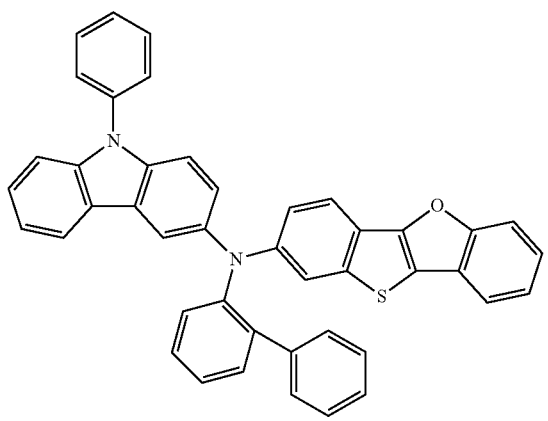
75
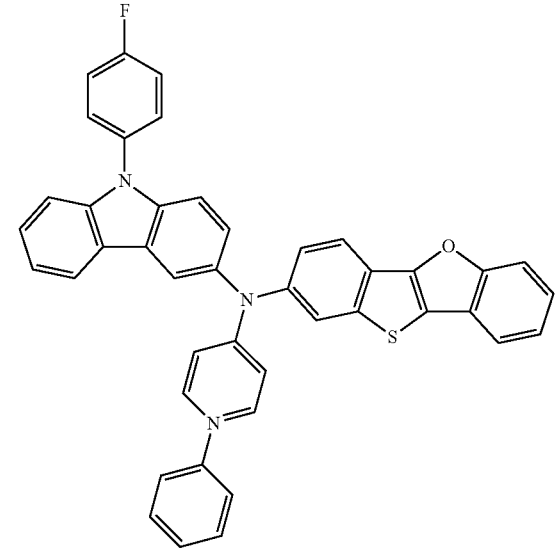
78
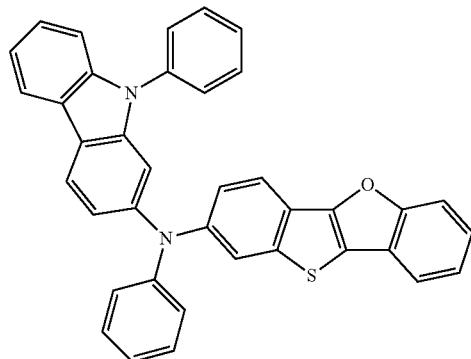
76
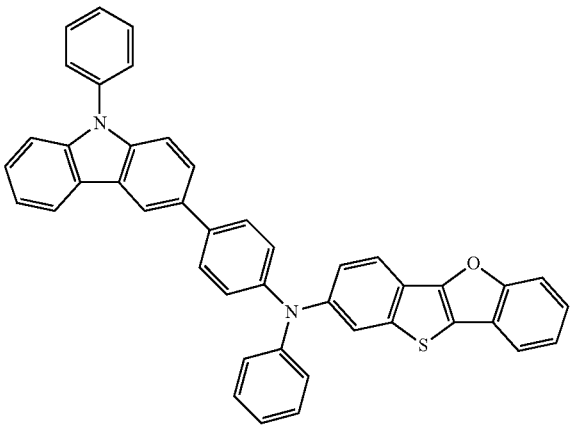
79

80
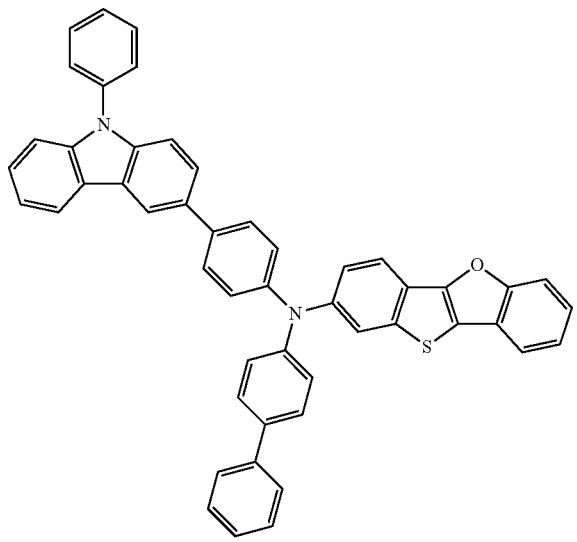
81
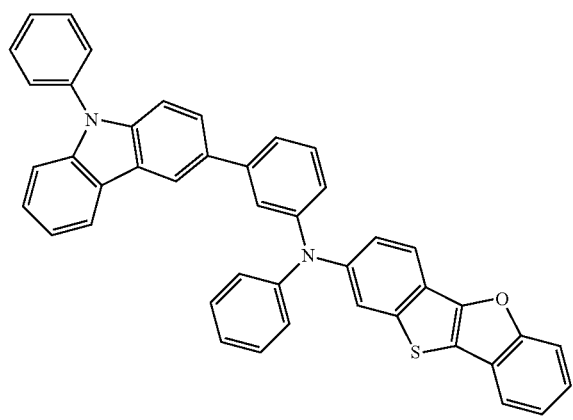
82
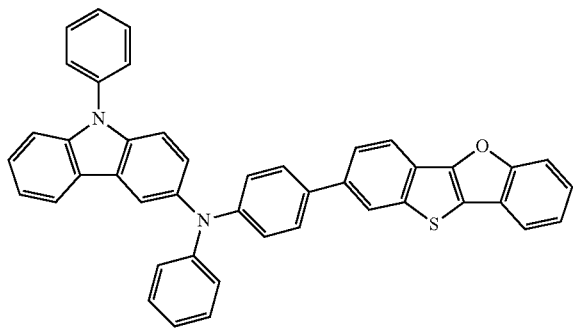
83
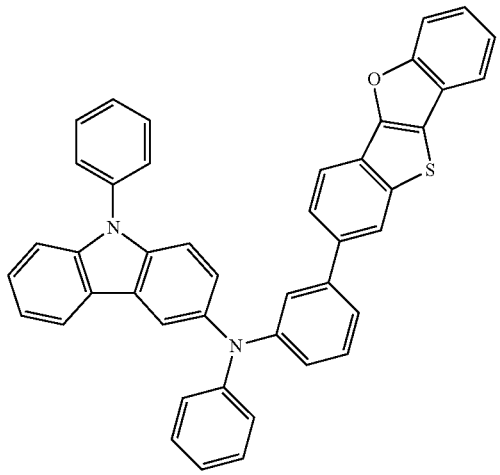
84
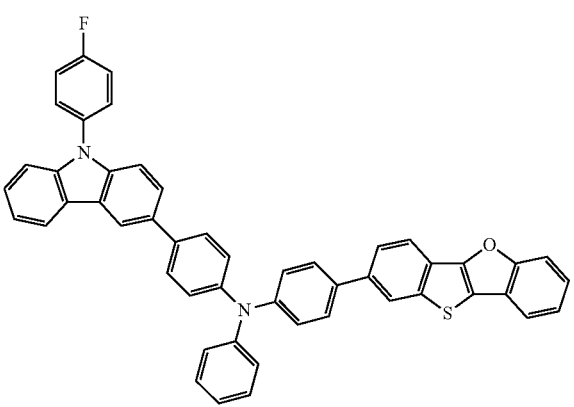
85
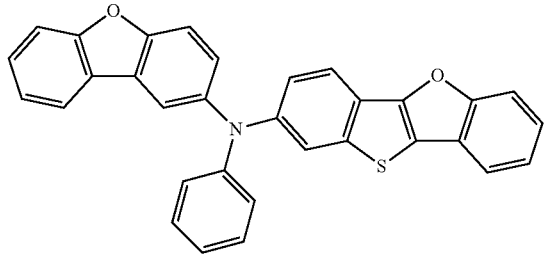
86

87
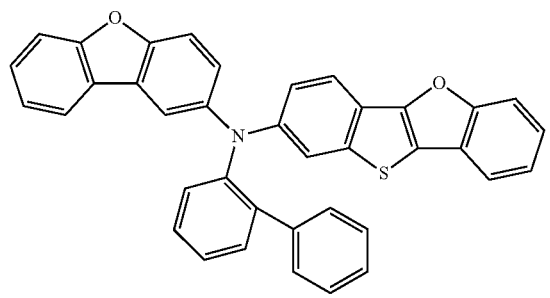
88
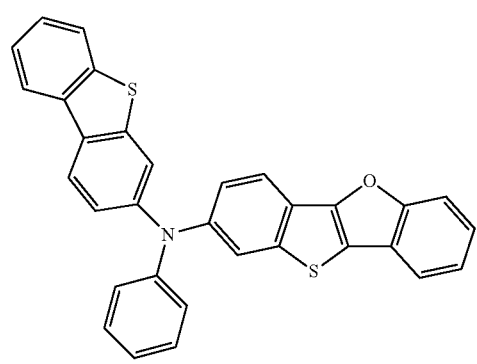
89
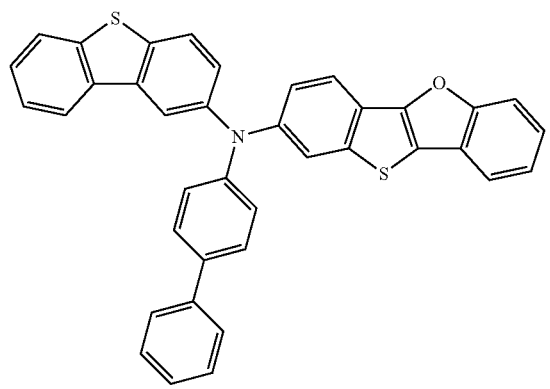
90
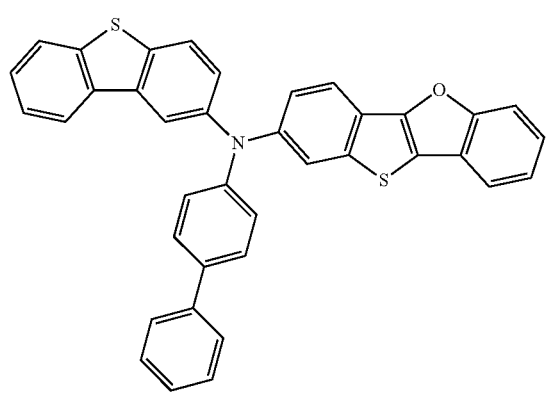
91
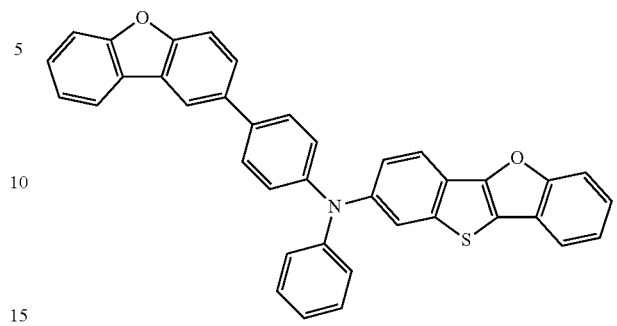
92
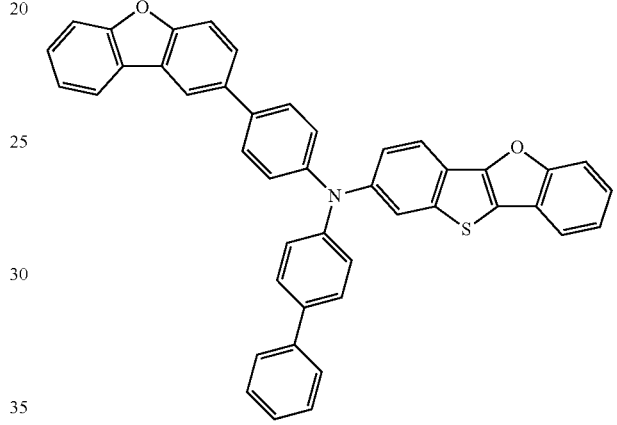
93
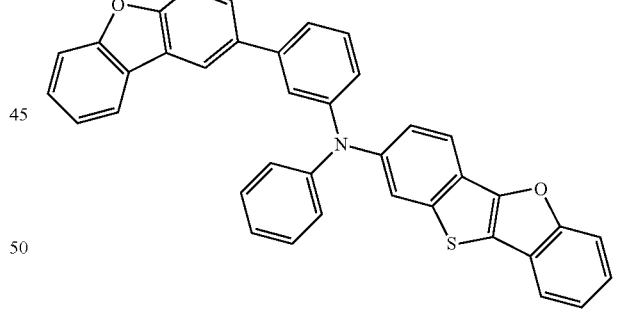
94
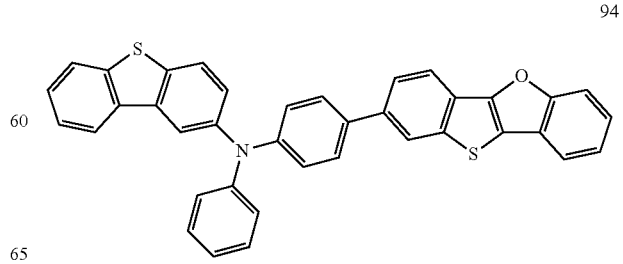

-continued

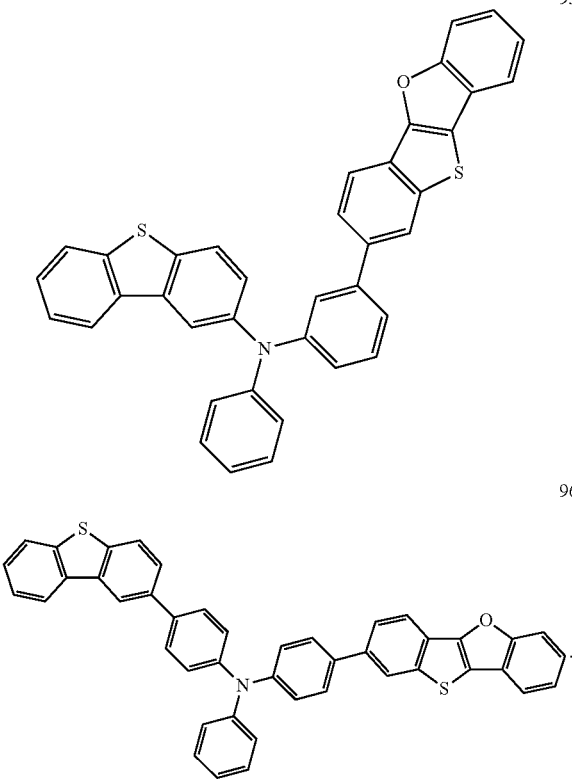

95

96

Referring to FIG. 1 to FIG. 4 again, the organic electroluminescence device according to embodiments of the present disclosure will be further described. The organic layer OL includes the above-described monoamine compound according to an embodiment of the present disclosure. For example, the organic layer OL includes the monoamine compound represented by Formula 1.

Hereinafter, explanation will be focused mainly on additional features of the monoamine compound according to embodiments of the present disclosure and features of the monoamine that are not described will be the same as the features of the monoamine compound described elsewhere herein.

The first electrode EL1 has conductivity (e.g., electrical conductivity). The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may include a transparent metal oxide such as indium tin oxide (ITO), indium zinc oxide (IZO), zinc oxide (ZnO), and indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the first electrode EL1 may have a multilayer structure including a reflective layer or a transflective layer, and a transmissive layer formed using ITO, IZO, ZnO, ITZO, etc. For example, the first electrode EL1 may include a three-layer structure of ITO/Ag/ITO.

The thickness of the first electrode EL1 may be from about 1,000 Å to about 10,000 Å, for example, from about 1,000 Å to about 3,000 Å.

The organic layer OL may be on the first electrode EL1. The organic layer OL may include a hole transport region HTR, an emission layer EML and an electron transport region ETR. If the organic layer OL includes the hole transport region HTR, the emission layer EML and the electron transport region ETR, at least one of these layers may include the monoamine compound according to an embodiment.

The hole transport region HTR is on the first electrode EL1. The hole transport region HTR may include at least one of a hole injection layer HIL, a hole transport layer HTL, a hole buffer layer, or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL, or a hole transport layer HTL, and may have a structure of a single layer formed using a hole injection material and a hole transport material. In some embodiments, the hole transport region HTR may have a structure of a single layer formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/ electron blocking layer EBL, without limitation.

In an embodiment, the hole transport region HTR may include the monoamine compound according to an embodiment of the present disclosure. The hole transport region HTR may have a multilayer structure having a plurality of layers, and one of the plurality of layers may include the monoamine compound represented by Formula 1. For example, the hole transport region HTR may include a hole injection layer HIL on the first electrode EL1 and the hole transport layer HTL on the hole injection layer HIL, and the hole transport layer HTL may include the monoamine compound represented by Formula 1. However, embodiments of the present disclosure are not limited thereto, and for example, the hole injection layer HIL may include the monoamine compound of an embodiment.

The hole transport region HTR may include one or two or more kinds of the monoamine compound of an embodiment. For example, the hole transport region HTR may include at least one selected from the compounds represented in Compound Group 1.

The hole transport region HTR may be formed using various suitable methods such as a vacuum deposition method, a spin coating method, a cast method, a Langmuir-Blodgett (LB) method, an inkjet printing method, a laser printing method, and a laser induced thermal imaging (LITI) method.

However, the hole transport region may further include the following materials in each layer.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4', 4"-tris(N,N-diphenylamino)triphenylamine (TDATA), 4,4', 4"-tris{N,N-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPD), triphenylamine-containing polyetherketone (TPAPEK), 4-isopropyl-4'-methyldiphenyliodonium tetrakis(pentafluorophenyl)borate, or dipyrazino[2,3-f: 2',3'-h]quinoxaline-2,3,6,7,10,11-hexacarbonitrile (HAT-CN).

The hole transport layer HTL may include the monoamine compound of an embodiment as described above. Any suitable materials generally used in the art for hole transport layers may be included in the hole transport layer, but embodiments of the present disclosure are not limited thereto. For example, the hole transport layer HTL may include carbazole derivatives such as N-phenyl carbazole and polyvinyl carbazole, fluorine derivatives, N,N'-bis(3-methylphenyl)-N,N'-diphenyl-[1,1-biphenyl]-4,4'-diamine (TPD), triphenylamine derivatives such as 4,4',4''-tris(N-carbazolyl)triphenylamine (TCTA), N,N'-di(naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The electron blocking layer EBL may include, for example, carbazole derivatives such as N-phenyl carbazole and polyvinyl carbazole, fluorine derivatives, N,N'-bis(3-methylphenyl)-N,N'-diphenyl-[1,1-biphenyl]-4,4'-diamine (TPD), triphenylamine derivatives such as 4,4',4''-tris(N-carbazolyl)triphenylamine (TCTA), N,N'-di(naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), mCP, etc.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, suitable or satisfactory hole transport properties may be achieved without substantial increase of a driving voltage.

The hole transport region HTR may further include a charge generating material in addition to the above-described materials to increase conductivity (e.g., electrical conductivity). The charge generating material may be dispersed uniformly or non-uniformly (e.g., irregularly) in the hole transport region HTR. The charge generating material may be, for example, a p-dopant. The p-dopant may be one of quinone derivatives, metal oxides, or cyano group-containing compounds, without limitation. However, embodiments of the present disclosure are not limited thereto.

For example, non-limiting examples of the p-dopant may include quinone derivatives such as tetracyanoquinodimethane (TCNQ) and 2,3,5,6-tetrafluoro-tetracyanoquinodimethane (F4-TCNQ), metal oxides such as tungsten oxide and molybdenum oxide, without limitation.

The hole transport region HTR may further include at least one of a hole buffer layer, or an electron blocking layer EBL. The hole buffer layer may compensate for an optical resonance distance according to the wavelength of light emitted from an emission layer EML and may increase light emission efficiency. Materials which may be included in a hole transport region HTR may be used as materials which may be included in a hole buffer layer. The electron blocking layer EBL is a layer playing the role of blocking the electron injection from the electron transport region ETR to the hole transport region HTR.

The emission layer EML is on the hole transport region HTR. The thickness of the emission layer EML may be, for example, from about 100 Å to about 1,000 Å, or from about 100 Å to about 600 Å. The emission layer EML may have a single layer formed using a single material, a single layer formed using a plurality of different materials, or a multilayer structure having a plurality of layers formed using a plurality of different materials.

As the materials of the emission layer EML, any suitable light-emitting materials available in the art may be used, and one selected from fluoranthene derivatives, pyrene derivative, arylacetylene derivative, anthracene derivatives, fluorene derivatives, perylene derivatives, chrysene derivatives, etc. may be used, without specific limitation. In some embodiments, pyrene derivatives, perylene derivatives, or anthracene derivatives may be used. For example, as the host material of the emission layer EML, anthracene derivatives represented by Formula 7 may be used.

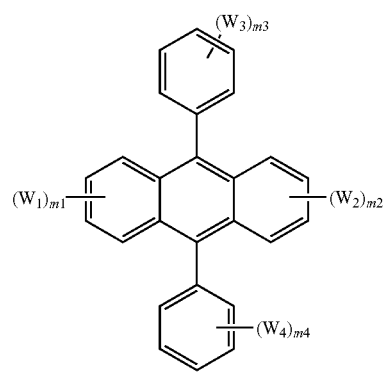

Formula 7

In Formula 7, $W_1$ to $W_4$ are each independently a hydrogen atom, a deuterium atom, a halogen atom, a substituted or unsubstituted silyl group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, or may be combined with an adjacent group to form a ring, where m1 and m2 are each independently an integer of 0 to 4, and m3 and m4 are each independently an integer of 0 to 5.

If m1 is 1, $W_1$ may not be a hydrogen atom, if m2 is 1, $W_2$ may not be a hydrogen atom, if m3 is 1, $W_3$ may not be a hydrogen atom, and if m4 is 1, $W_4$ may not be a hydrogen atom.

If m1 is 2 or more, a plurality of $W_1$ groups are the same or different. If m2 is 2 or more, a plurality of $W_2$ groups are the same or different. If m3 is 2 or more, a plurality of $W_3$ groups are the same or different. If m4 is 2 or more, a plurality of $W_4$ groups are the same or different.

The compound represented by Formula 7 may include the compounds represented by the following structures, but the compound represented by Formula 7 is not limited thereto:
a-1
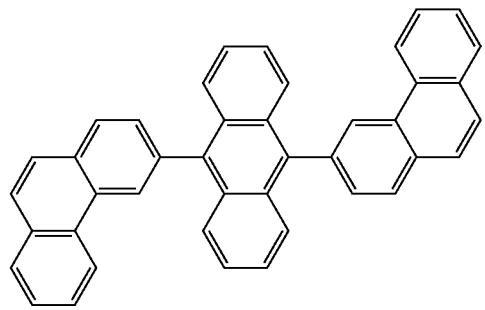
a-2
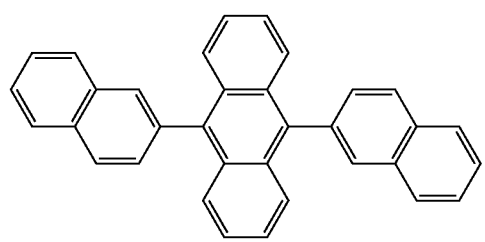
a-3
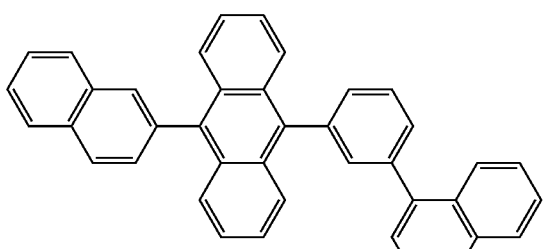
a-4
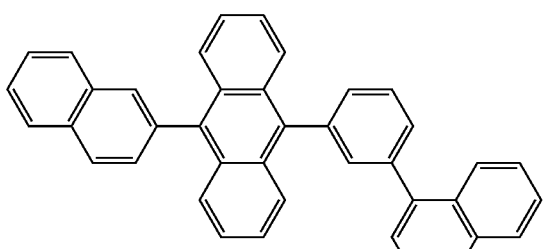
a-5
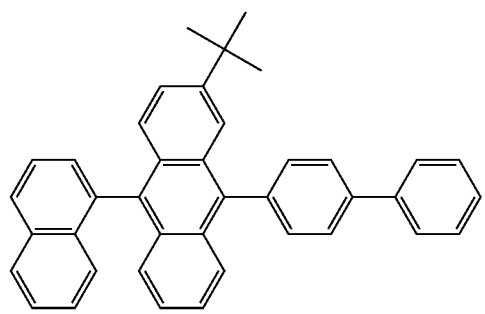
a-6
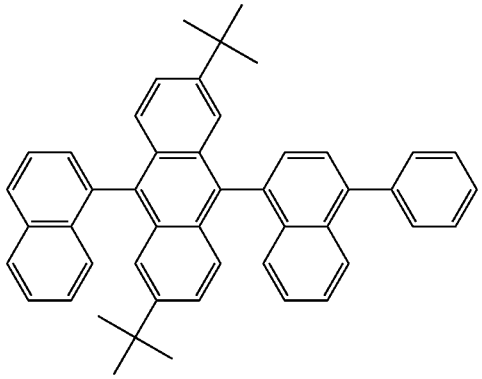
a-7
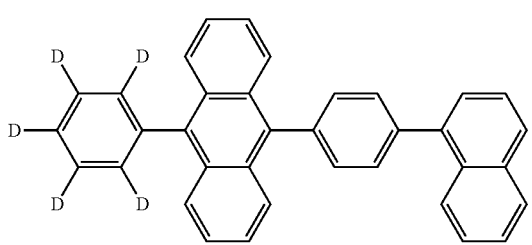
a-8
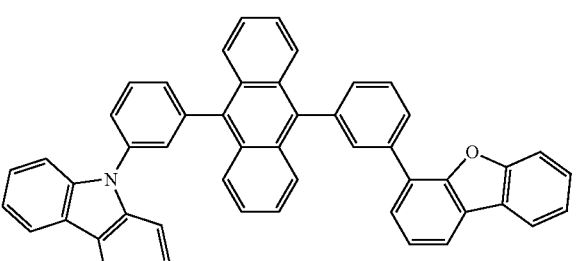
a-9
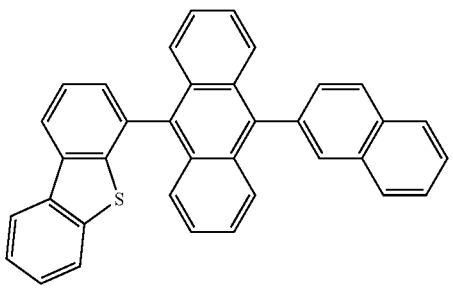
a-10
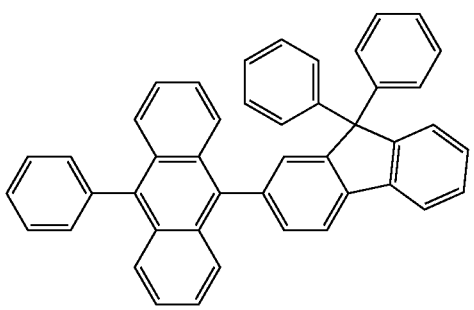

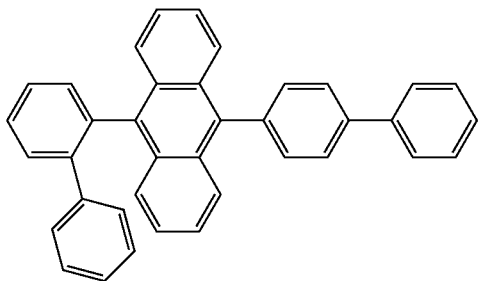

a-11

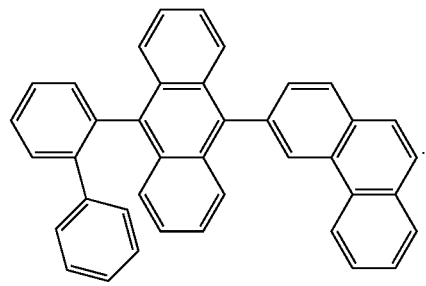

a-12

The emission layer EML may include, for example, a fluorescence material including any one selected from the group consisting of spiro-DPVBi, 2,2',7,7'-tetrakis(biphenyl-4-yl)-9,9'-spirobifluorene(spiro-sexiphenyl) (spiro-6P), distyryl-benzene (DSB), distyryl-arylene (DSA), a polyfluorene (PFO)-based polymer and a poly(p-phenylene vinylene) (PPV)-based polymer.

The emission layer EML may further include a dopant, and the dopant may use any suitable material available in the art as a dopant. For example, styryl derivatives (for example, 1,4-bis[2-(3-N-ethylcarbazolyl)vinyl]benzene (BCzVB), 4-(di-p-tolylamino)-4"-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (for example, 2,5,8,11-tetra-t-butylperylene (TBPe)), pyrene and the derivatives thereof (for example, 1,1-dipyrene, 1,4-dipyrenylbenzene, 1,4-bis(N,N-diphenylamino)pyrene, and 1,6-bis(N,N-diphenylamino)pyrene), 2,5,8,11-tetra-t-butylperylene (TBP), 1,3,5-tris(N-phenylbenzimidazole-2-yl)benzene (TPBi), etc., may be used as the dopant.

The emission layer EML may include, for example, tris(8-hydroxyquinolino)aluminum (Alq3), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(1-phenyl-1H-benzo[d]imidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane (DP-$SiO_4$), 2,8-bis(diphenylphosphoryl)dibenzofuran (PPF), etc.

The electron transport region ETR is on the emission layer EML. The electron transport region ETR may include at least one of an hole blocking layer HBL, an electron transport layer ETL, or an electron injection layer EIL, but embodiments of the present disclosure are not limited thereto.

The electron transport region ETR may have a single layer formed using a single material, a single layer formed using a plurality of different materials, or a multilayer structure including a plurality of layers formed using a plurality of different materials.

For example, the electron transport region ETR may have the structure of a single layer such as an electron injection layer EIL, or an electron transport layer ETL, and may have a structure of a single layer formed using an electron injection material and an electron transport material. In addition, the electron transport region ETR may have a single layer structure having a plurality of different materials, or a structure laminated from the emission layer EML of electron transport layer ETL/electron injection layer EIL, or hole blocking layer HBL/electron transport layer ETL/electron injection layer EIL, without limitation. The thickness of the electron transport region ETR may be, for example, from about 100 Å to about 1,500 Å.

The electron transport region ETR may be formed using various suitable methods such as a vacuum deposition method, a spin coating method, a cast method, a Langmuir-Blodgett (LB) method, an inkjet printing method, a laser printing method, and/or a laser induced thermal imaging (LITI) method.

If the electron transport region ETR includes an electron transport layer ETL, the electron transport region ETR may include tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-ylphenyl)-9,10-dinaphthylanthracene, 1,3,5-tris(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalene-2-yl)anthracene (ADN), or a mixture thereof. However, embodiments of the present disclosure are not limited thereto. The thickness of the electron transport layer ETL may be from about 100 Å to about 1,000 Å and may be, for example, from about 150 Å to about 500 Å. If the thickness of the electron transport layer ETL satisfies the above-described range, suitable or satisfactory electron transport properties may be obtained without substantial increase of a driving voltage.

If the electron transport region ETR includes the electron injection layer EIL, the electron transport region ETR may include a metal halide such as LiF, NaCl, CsF, RbCl, RbI, a metal of the lanthanides such as, for example, Yb, a metal oxide such as $Li_2O$, BaO, or a lithium quinolate (LiQ). However, embodiments of the present disclosure are not limited thereto. The electron injection layer EIL also may be formed using a mixture material of an electron transport material and an insulating organo metal salt. The organo metal salt may be a material having an energy band gap of about 4 eV or more. In some embodiments, the organo metal salt may include, for example, metal acetates, metal benzoates, metal acetoacetates, metal acetylacetonates, or metal stearates. The thickness of the electron injection layer EIL may be from about 1 Å to about 100 Å, and from about 3 Å to about 90 Å. If the thickness of the electron injection layer EIL satisfies the above described range, suitable or satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, embodiments of the present disclosure are not limited thereto.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the second electrode EL2 may have a multi-layered structure including a reflective layer or a transflective layer formed using the above-described materials, and a transparent conductive layer formed using ITO, IZO, ZnO, ITZO, etc.

In some embodiments, the second electrode EL2 may be connected with an auxiliary electrode. If the second electrode EL2 is connected with the auxiliary electrode, the resistance of the second electrode EL2 may be decreased.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may transition (e.g., relax) from an excited state to a ground state resulting in the emission of light.

If the organic electroluminescence device 10 is a top emission type (a top emission organic electroluminescence device), the first electrode EL1 may be a reflective electrode and the second electrode EL2 may be a transmissive electrode or a transflective electrode. If the organic electroluminescence device 10 is a bottom emission type (a bottom emission organic electroluminescence device), the first electrode EL1 may be a transmissive electrode or a transflective electrode and the second electrode EL2 may be a reflective electrode.

The organic electroluminescence device 10 according to embodiments of the present disclosure includes the monoamine compound of an embodiment, and accordingly, the increase of efficiency and life may be achieved. In addition, the effect of decreasing a driving voltage may be achieved.

Hereinafter, embodiments of the present disclosure will be explained in more detail with reference to examples and comparative examples. The embodiments are only illustrations for assisting the understanding of the present disclosure, and the scope of the present disclosure is not limited thereto.

Synthetic Examples

The monoamine compound according to an embodiment of the present disclosure may be synthesized, for example, as follows. However, the synthetic method of the monoamine compound according to an embodiment of the present disclosure is not limited thereto.

1. Synthesis of Compound 5
(1) Synthesis of Compound A

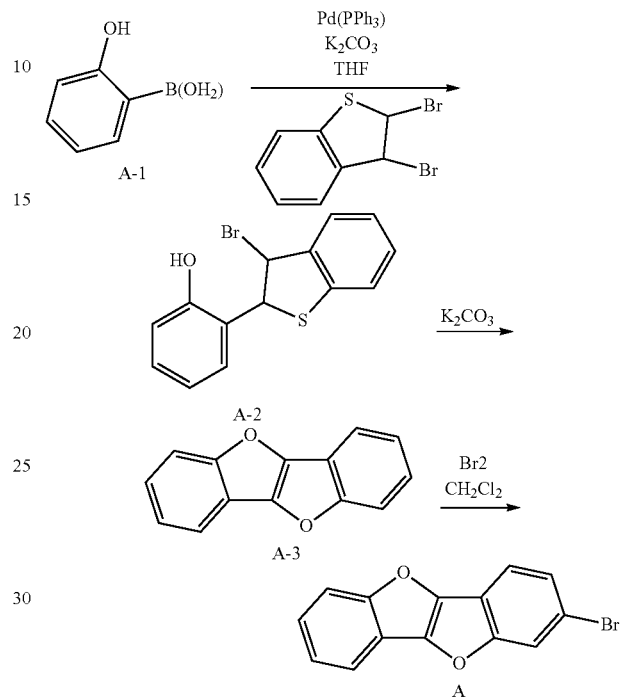

A-1 (1.1 g), 2,3-dibromo-2,3-dihydrobenzofuran (2.5 g), Pd(PPh$_3$)$_4$ (0.5 g) and K$_2$CO$_3$ (3.1 g) were dissolved in THF (50 ml) and stirred at about 80° C. for about 10 hours. The temperature of the reaction solution was decreased to room temperature and the reaction was quenched using water. The resultant product was extracted with ethyl ether three times. The organic layer thus separated was dried with anhydrous magnesium sulfate and then distilled at a reduced pressure. The crude product thus obtained was separated by column chromatography to obtain Intermediate A-2 (2.6 g, yield: 65%).

Intermediate A-2 (2.6 g) and K$_2$CO$_3$ (3.7 g) were dissolved in THF (50 ml) and stirred at about 80° C. for about 3 hours. The temperature of the reaction solution was decreased to room temperature and the reaction was quenched using water. The resultant product was extracted with ethyl ether three times. The organic layer thus separated was dried with anhydrous magnesium sulfate and then distilled at a reduced pressure. The crude product thus obtained was separated by column chromatography to obtain Intermediate A-3 (1.5 g, yield: 80%).

To Intermediate A-3 (1.5 g), Br$_2$ (1.24 g) dissolved in dichloromethane (30 ml) was added and then, stirred at room temperature for about 3 hours. The reaction solution was quenched with water, and an aqueous Na$_2$S$_2$O$_3$ solution (100 ml) was added thereto. Then, the resultant product was extracted with dichloromethane and water three times. The organic layer thus separated was dried with anhydrous magnesium sulfate and then distilled in a reduced pressure. The crude product thus obtained was separated by column chromatography to obtain Compound A (1.43 g, yield: 70%).

(2) Synthesis of Compound 5

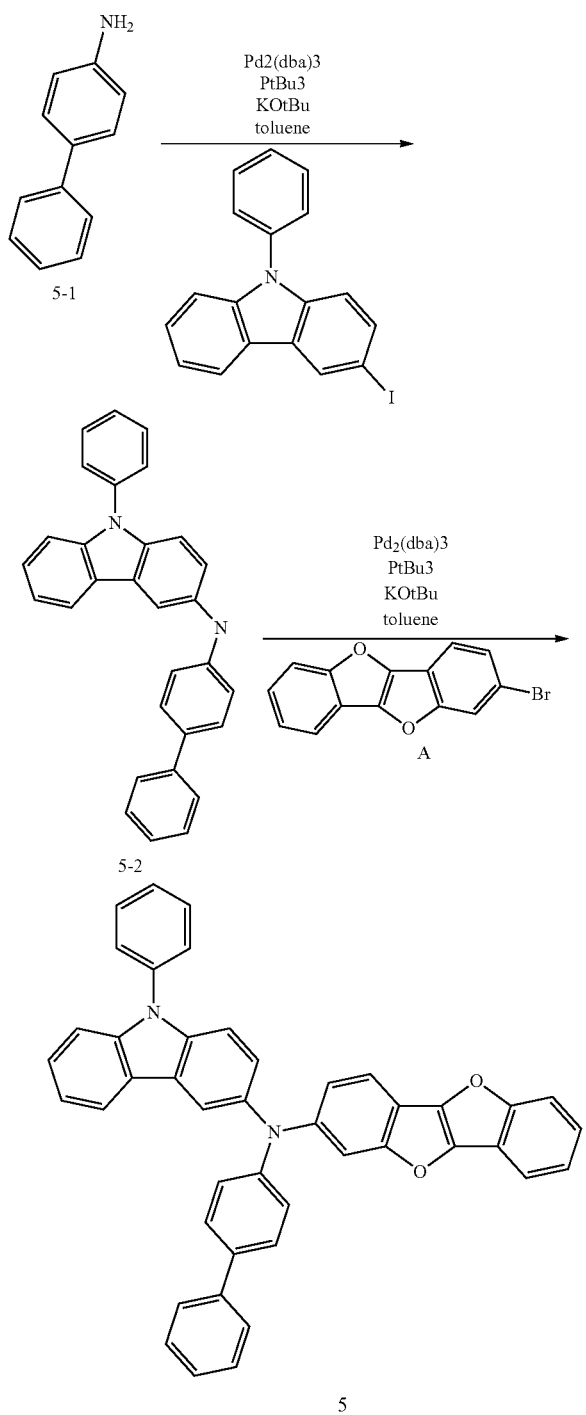

5-2

5

Reactant 5-1 (1.6 g), 3-iodo-9-phenyl-9H-carbazol (4.6 g), Pd$_2$(dba)$_3$ (0.5 g), PtBu$_3$ (0.2 ml) and KOtBu (2.8 g) were dissolved in toluene (50 ml) and stirred at about 85° C. for about 1 hour. The temperature of the reaction solution was decreased to room temperature and the reaction was quenched using water. The resultant product was extracted with ethyl ether three times. The organic layer thus separated was dried with anhydrous magnesium sulfate and then distilled in a reduced pressure. The crude product thus obtained was separated by column chromatography to obtain Intermediate 5-2 (2.6 g, yield: 65%).

Compound 5 (2.6 g, yield: 80%) was obtained according to substantially the same method as in the synthetic method of Intermediate 5-2 except for using Intermediate 5-2 (2.6 g) and Compound A (2.2 g) instead of reactant 5-1 and 3-iodo-9-phenyl-9H-carbazole.

2. Synthesis of Compound 24

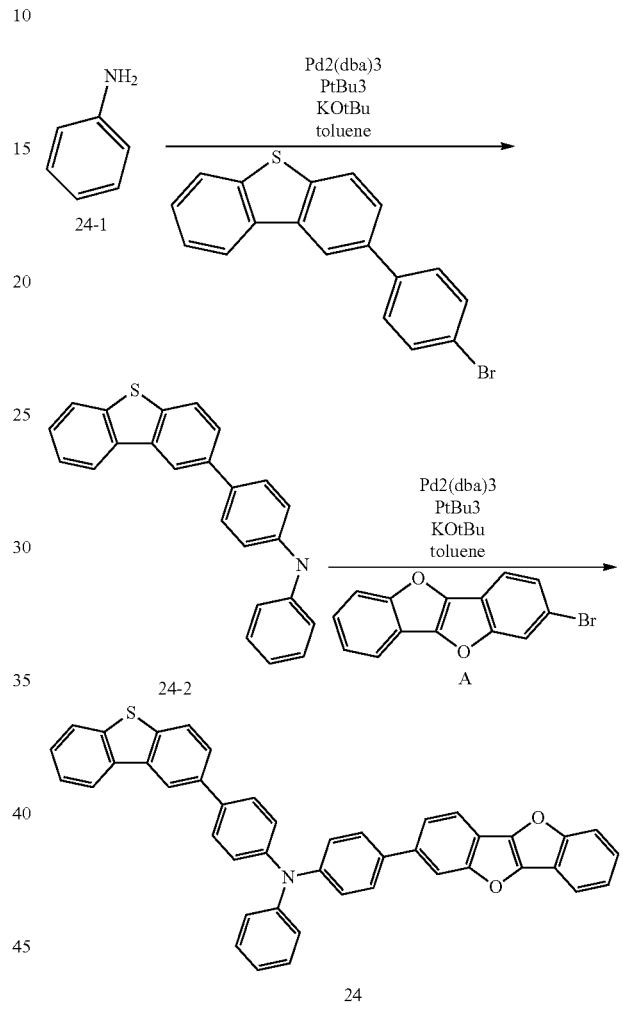

24

Reactant 24-1 (1.1 g), 2-(4-bromophenyl)dibenzo[b,d]thiophene (3.3 g), Pd$_2$(dba)$_3$ (0.5 g), PtBu$_3$ (0.2 ml) and KOtBu (2.8 g) were dissolved in toluene (50 ml) and stirred at about 85° C. for about 1 hour. The temperature of the reaction solution was decreased to room temperature and the reaction was quenched using water. The resultant product was extracted with ethyl ether three times. The organic layer thus separated was dried with anhydrous magnesium sulfate and then distilled in a reduced pressure. The crude product thus obtained was separated by column chromatography to obtain Intermediate 24-2 (2.5 g, yield: 75%).

Compound 24 (2.2 g, yield: 70%) was obtained according to substantially the same method as in the synthetic method of Intermediate 24-2 except for using Intermediate 24-2 (2.5 g) and Compound A (2.2 g) instead of reactant 24-1 and 2-(4-bromophenyl)dibenzo[b,d]thiophene.

3. Synthesis of Compound 32

(1) Synthesis of Reactant C

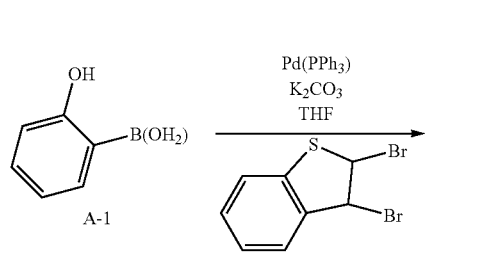

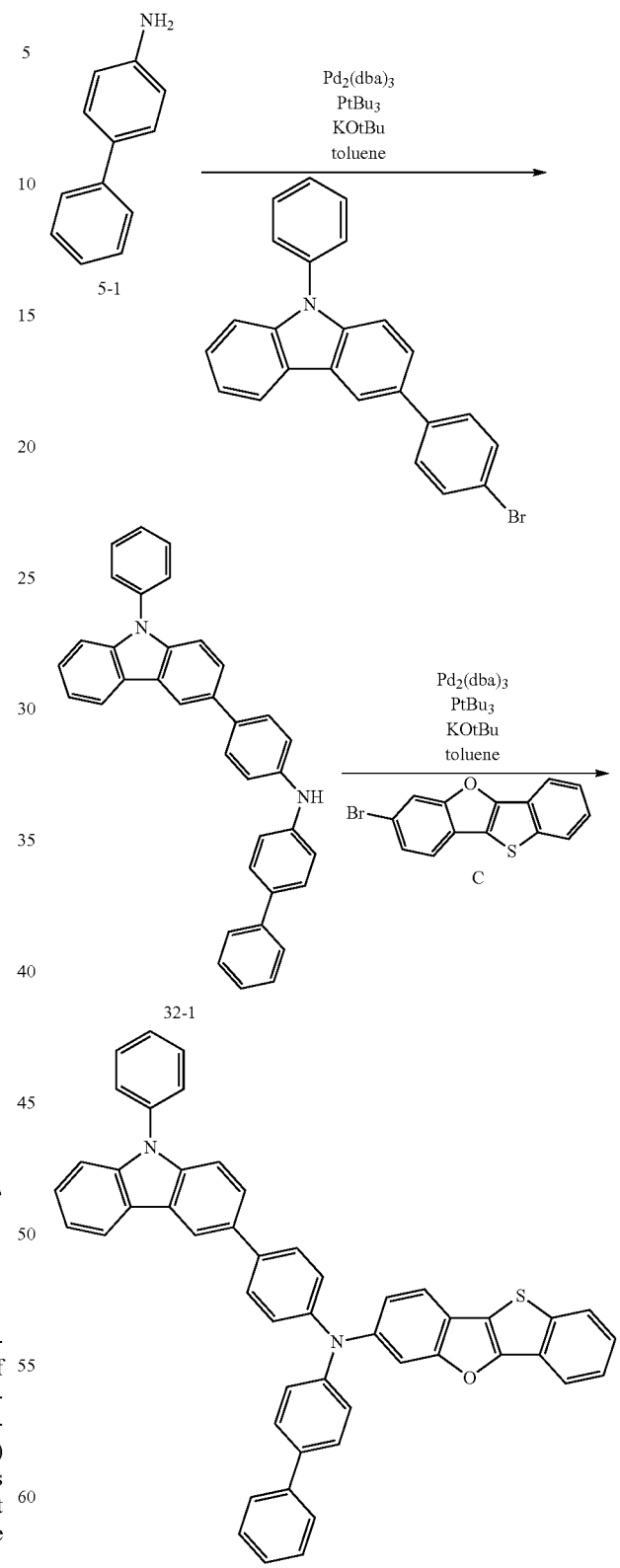

Intermediate B-1 (2.4 g) was obtained according to substantially the same method as in the synthetic method of Intermediate A-2 except for using 2,3-dibromo-2,3-dihydrobenzo[b]thiophene (2.6 g) instead of 2,3-dibromo-2,3-dihydrobenzofuran. Intermediate B-2 (1.6 g, yield: 80%) was obtained according to substantially the same method as in the synthetic method of Intermediate A-3, except that Intermediate B-1 (2.4 g) was used instead of Intermediate A-2.

Compound C (1.5 g, yield 70%) was obtained according to substantially the same method as in the synthetic method of Compound A, except that Intermediate B-2 (1.6 g) was used instead of Intermediate A-3.

(2) Synthesis of Compound 32

5-1 (2.0 g), 3-(4-bromophenyl)-9-phenyl-9H-carbazole (4.3 g), Pd$_2$(dba)$_3$ (0.5 g), PtBu$_3$ (0.2 ml) and KOtBu (2.8 g)

were dissolved in toluene (50 ml) and stirred at about 85° C. for about 1 hour. The temperature of the reaction solution was decreased to room temperature and the reaction was quenched using water. The resultant product was extracted with ethyl ether three times. The organic layer thus separated was dried with anhydrous magnesium sulfate and then distilled in a reduced pressure. The crude product thus obtained was separated by column chromatography to obtain Intermediate 32-1 (3.5 g, yield: 80%).

Compound 32 (2.5 g, yield: 70%) was obtained according to substantially the same method as in the synthetic method of Intermediate 32-1 except for using Intermediate 32-1 (3.5 g) and Compound C (2.3 g) instead of reactant 5-1 (2.0 g) and 3-(4-bromophenyl)-9-phenyl-9H-carbazole (4.3 g).

4. Synthesis of Compound 59

(1) Synthesis of Compound D

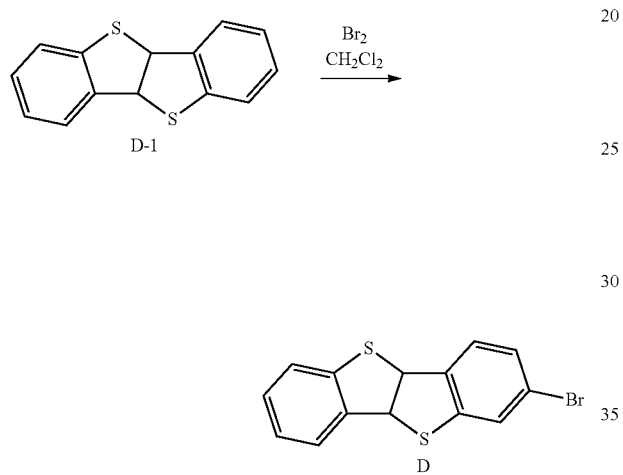

To D-1 (1.7 g), Br$_2$ (1.24 g) dissolved in dichloromethane (30 ml) was added and stirred at room temperature for about 3 hours. The reaction solution was quenched with water, and an aqueous Na$_2$S$_2$O$_3$ solution (100 ml) was added thereto. Then, the resultant product was extracted with dichloromethane and water three times. The organic layer thus separated was dried with anhydrous magnesium sulfate and then distilled in a reduced pressure. The crude product thus obtained was separated by recrystallization to obtain Compound D (1.6 g, yield: 70%).

(2) Synthesis of Compound 59

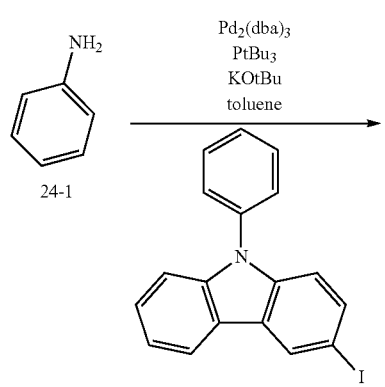

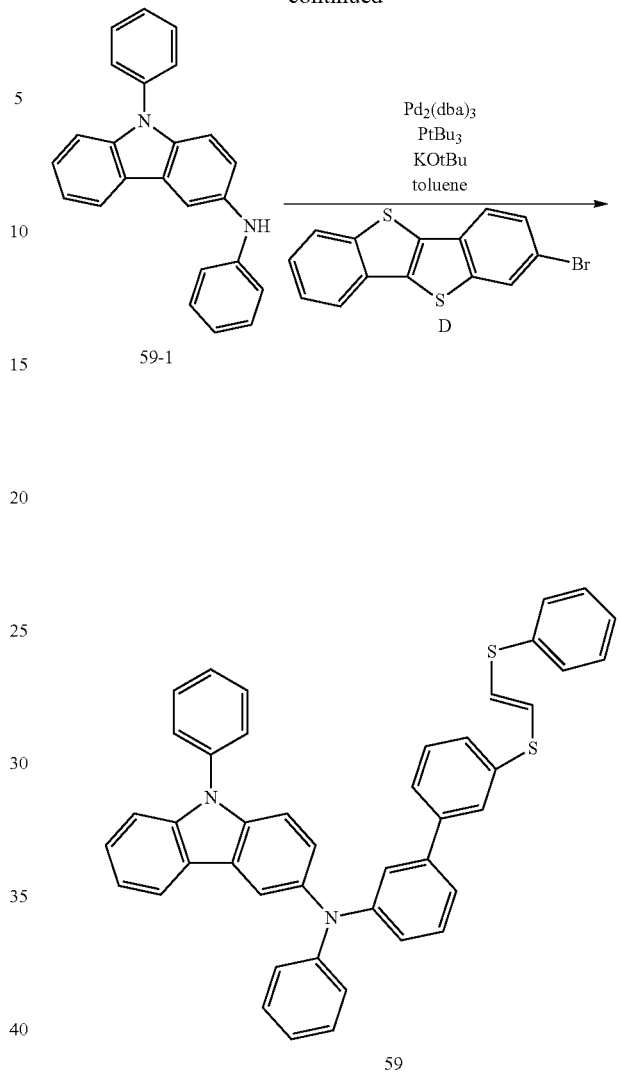

Reactant 24-1 (1.2 g), 3-iodo-9-phenyl-9H-carbazole (3.4 g), Pd$_2$(dba)$_3$ (0.5 g), PtBu$_3$ (0.2 ml) and KOtBu (2.8 g) were dissolved in toluene (50 ml) and stirred at about 85° C. for about 1 hour. The temperature of the reaction solution was decreased to room temperature and the reaction was quenched using water. The resultant product was extracted with ethyl ether three times. The organic layer thus separated was dried with anhydrous magnesium sulfate and then distilled in a reduced pressure. The crude product thus obtained was separated by column chromatography to obtain Intermediate 59-1 (2.2 g, yield: 65%).

Compound 59 (2.4 g, yield: 75%) was obtained according to substantially the same method as in the synthetic method of Intermediate 59-1 except for using Intermediate 59-1 (2.2 g) and Compound D (2.2 g) instead of reactant 24-1 and 3-iodo-9-phenyl-9H-carbazole.

5. Synthesis of Compound 67

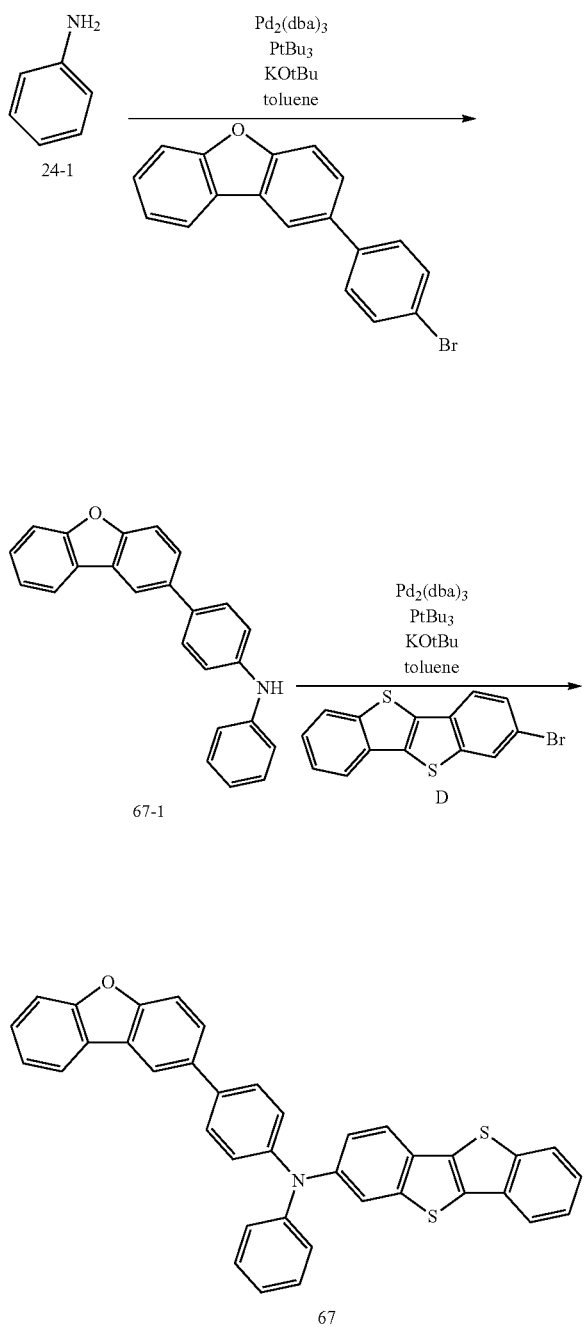

Intermediate 24-1 (1.2 g), 2-(4-bromophenyl)dibenzo[b,d]furan (3.0 g), Pd$_2$(dba)$_3$ (0.5 g), PtBu$_3$ (0.2 ml) and KOtBu (2.5 g) were dissolved in toluene (50 ml) and stirred at about 85° C. for about 1 hour. The temperature of the reaction solution was decreased to room temperature and the reaction was quenched using water. The resultant product was extracted with ethyl ether three times. The organic layer thus separated was dried with anhydrous magnesium sulfate and then distilled in a reduced pressure. The crude product thus obtained was separated by column chromatography to obtain Intermediate 67-1 (2.1 g, yield: 66%).

Compound 67 (3.6 g, yield: 80%) was obtained according to substantially the same method as in the synthetic method of Intermediate 67-1 except for using Intermediate 67-1 (2.1 g) and Compound D (2.3 g) instead of intermediate 24-1 and 2-(4-bromophenyl)dibenzo[b,d]furan.

6. Synthesis of Compound 75
(1) Synthesis of Compound B

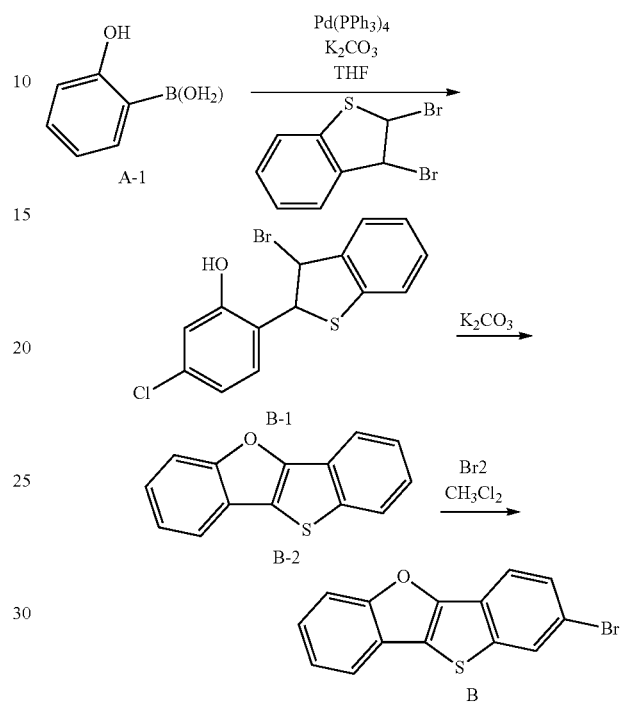

Intermediate B-1 (2.4 g) was obtained according to substantially the same method as in the synthetic method of Intermediate A-2 except for using 2,3-dibromo-2,3-dihydrobenzo[b]thiophene (2.6 g) instead of 2,3-dibromo-2,3-dihydrobenzofuran.

Intermediate B-2 (1.6 g, yield: 80%) was obtained according to substantially the same method as in the synthetic method of Intermediate A-3, except that Intermediate B-1 (2.4 g) was used instead of Intermediate A-2.

Compound B (1.5 g, yield 70%) was obtained according to substantially the same method as in the synthetic method of Compound A, except that Intermediate B-2 (1.6 g) was used instead of Intermediate A-3.

(2) Synthesis of Compound 75

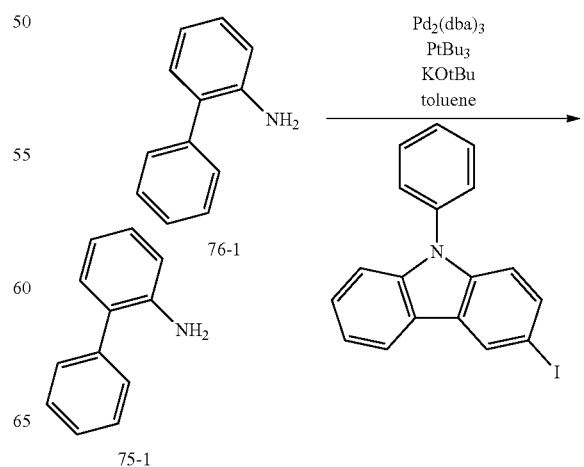

-continued

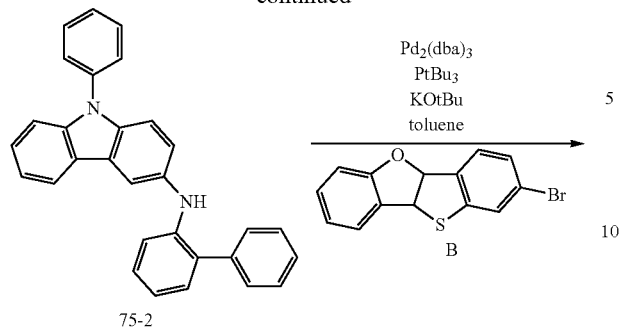

75-2

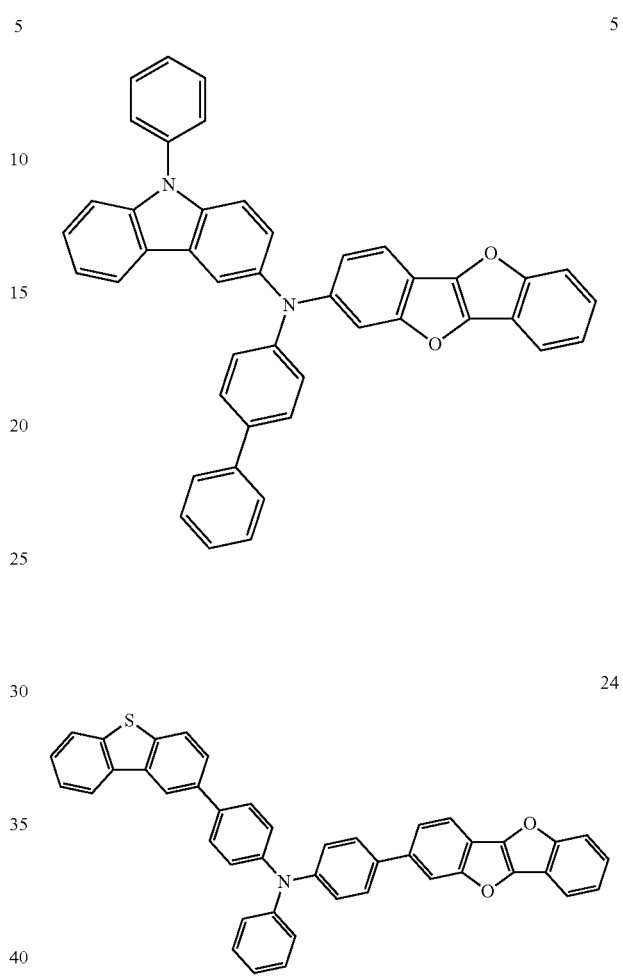

Example Compounds

5

24

32

75

Intermediate 75-1 (1.8 g), 3-iodo-9-phenyl-9H-carbazole (3.9 g), Pd$_2$(dba)$_3$ (0.5 g), PtBu$_3$ (0.2 ml) and KOtBu (2.7 g) were dissolved in toluene (50 ml) and stirred at about 85° C. for about 1 hour. The temperature of the reaction solution was decreased to room temperature and the reaction was quenched using water. The resultant product was extracted with ethyl ether three times. The organic layer thus separated was dried with anhydrous magnesium sulfate and then distilled in a reduced pressure. The crude product thus obtained was separated by column chromatography to obtain Intermediate 75-2 (2.0 g, yield: 60%).

Compound 75 (2.5 g, yield: 79%) was obtained according to substantially the same method as in the synthetic method of Intermediate 75-2, except that Intermediate 75-2 (2.0 g) and Compound B (2.2 g) were used instead of Intermediate 75-1 and 3-iodo-9-phenyl-9H-carbazole.

Device Manufacturing Examples

Organic electroluminescence devices of Examples 1 to 6 were manufactured using the above-described Compounds 5, 24, 32, 59, 67 and 75, respectively, as materials for a hole transport region.

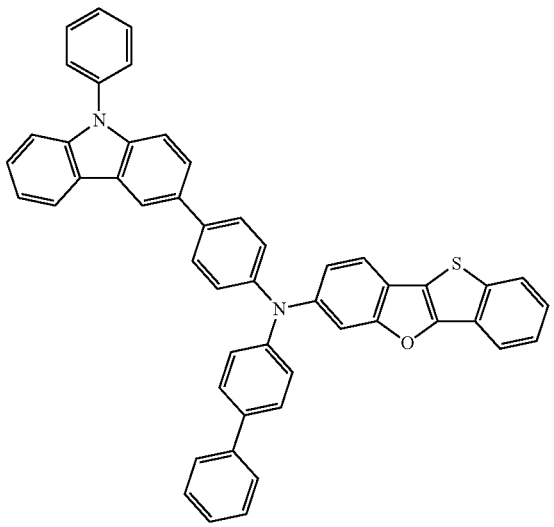

-continued
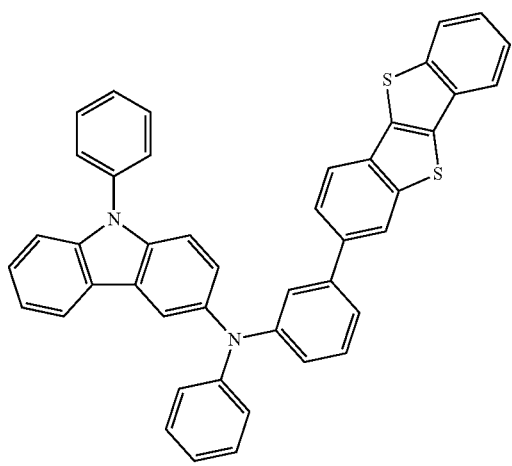
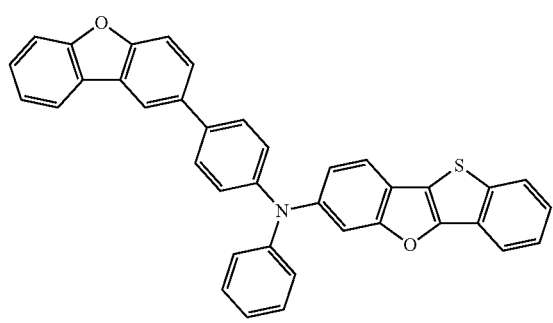
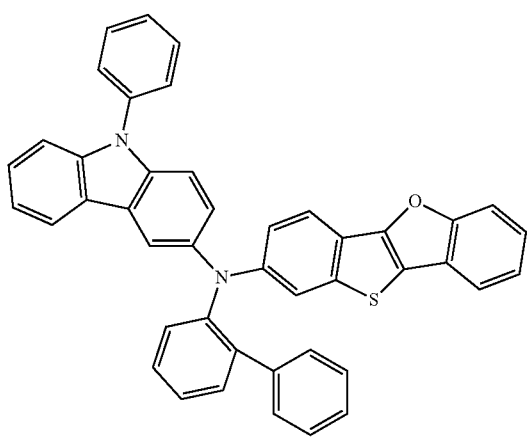
Organic electroluminescence devices of Comparative Examples 1 to 4 were manufactured using Compounds R-1 to R-4, respectively, below as materials for a hole transport region.
Comparative Compounds
R-1
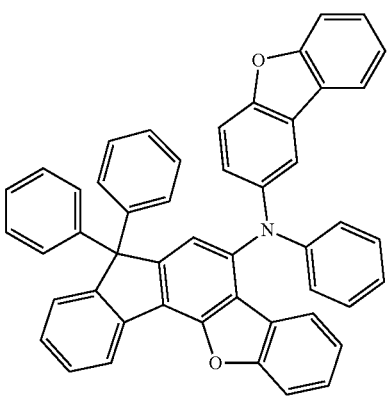
R-2
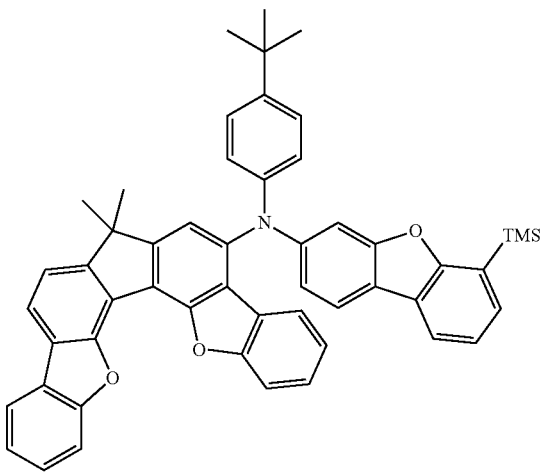
R-3
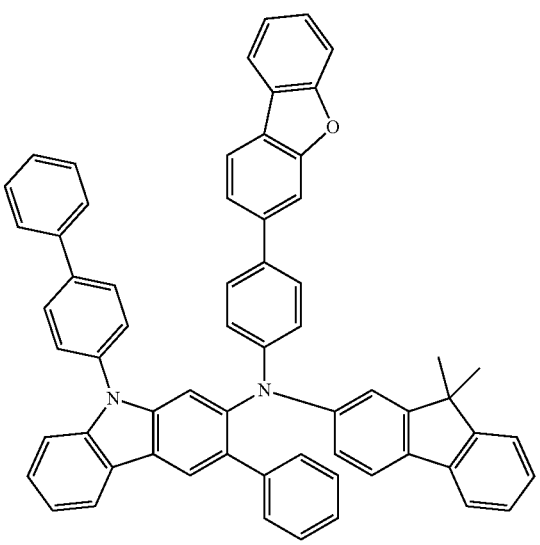

-continued

R-4

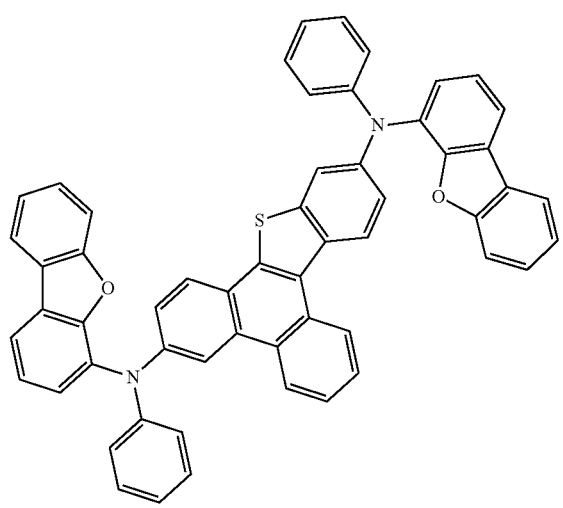

The organic electroluminescence devices of the Examples and the Comparative Examples were manufactured as follows. As an anode, an ITO glass substrate of about 15 Ω/cm² (about 1,200 Å) of Corning Co. was cut to a size of 50 mm×50 mm×0.7 mm and cleansed by ultrasonic waves using isopropyl alcohol and pure water for 5 minutes, respectively, and then cleansed by irradiating ultraviolet rays for about 30 minutes and exposing to ozone. The glass substrate was installed in a vacuum deposition apparatus. On the substrate, 2-TNATA was deposited in vacuum as a hole injection material to a thickness of about 600 Å, and the Example Compound or Comparative Compound was deposited in vacuum as a hole transport compound to a thickness of about 300 Å to form a hole transport layer.

On the hole transport layer, 9,10-di(naphthalen-2-yl)anthracene (hereinafter, DNA) as a blue fluorescence host and 4,4'-bis[2-(4-(N,N-diphenylamino)phenyl)vinyl]biphenyl (hereinafter, DPAVBi) as a blue fluorescence dopant were deposited to a weight ratio of 98:2 to a thickness of about 300 Å to form an emission layer.

Then, on the emission layer, Alq3 was deposited to a thickness of about 300 Å as an electron transport layer. On the electron transport layer, alkali metal halide, LiF was deposited to a thickness of about 10 Å as an electron injection layer, and Al was deposited in vacuum to a thickness of about 3,000 Å (anode electrode) to form a LiF/Al electrode. An organic electroluminescence device was manufactured. Each layer was formed by a vacuum deposition method.

Compounds for Forming Device

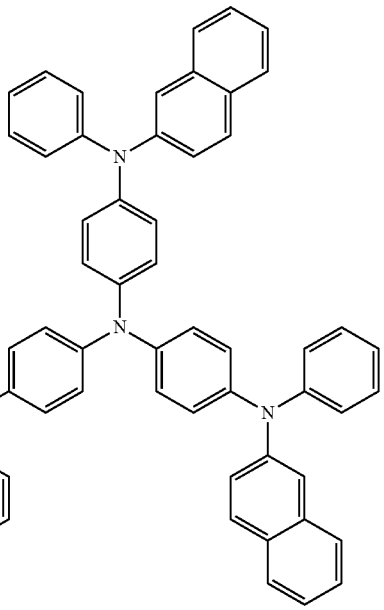

2-TNATA

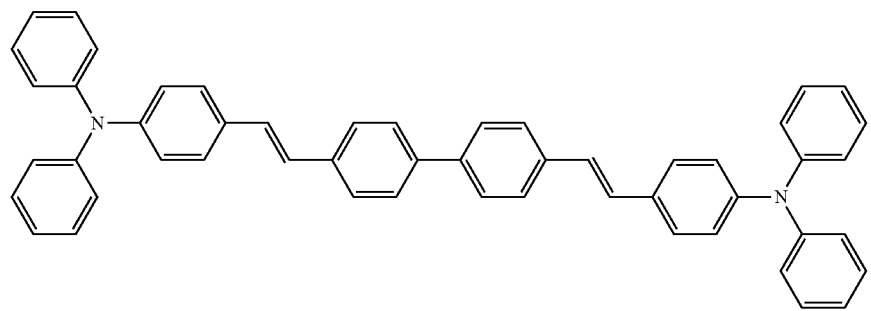

DPAVBi

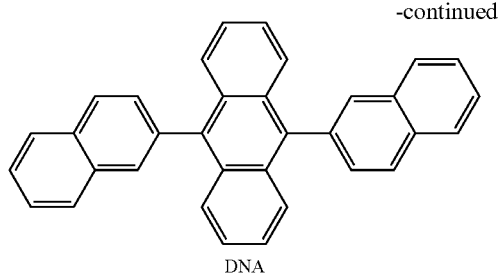

DNA

The respective emission efficiencies of the organic electroluminescence devices according to Examples 1 to 6 and Comparative Examples 1 to 4 are listed in Table 1 below. The emission efficiency is a value measured at about 50 mA/cm², and half life is the test result at 1.0 mA/cm².

TABLE 1

|  | Hole transport layer | Voltage (V) | Luminance (cd/m²) | Efficiency (cd/A) | Life (h) |
|---|---|---|---|---|---|
| Example 1 | Example Compound 5 | 4.89 | 3410 | 6.82 | 412 |
| Example 2 | Example Compound 24 | 4.87 | 3435 | 6.87 | 406 |
| Example 3 | Example Compound 32 | 4.64 | 3385 | 6.77 | 419 |
| Example 4 | Example Compound 59 | 4.56 | 3460 | 6.92 | 423 |
| Example 5 | Example Compound 67 | 4.67 | 3475 | 6.95 | 410 |
| Example 6 | Example Compound 75 | 4.87 | 3300 | 6.60 | 405 |
| Comparative Example 1 | Comparative Compound R-1 | 5.9 | 2645 | 5.29 | 258 |
| Comparative Example 2 | Comparative Compound R-2 | 5.7 | 3121 | 5.4 | 298 |
| Comparative Example 3 | Comparative Compound R-3 | 6.8 | 2854 | 5.2 | 235 |
| Comparative Example 4 | Comparative Compound R-4 | 7.0 | 2587 | 5.5 | 260 |

Referring to Table 1, Examples 1 to 6 were found to accomplish a low voltage, long life, and high efficiency when compared with Comparative Examples 1 to 4. Particularly, due to the improving effect of the life of the devices of the Example, the life was largely increased when compared with the Comparative Examples.

While the present disclosure is not limited by any particular mechanism or theory, the monoamine compound according to embodiments of the present disclosure is thought to have a highest occupied molecular orbital (HOMO) that is shallower (e.g., that has a lower energy level) than that of the comparative materials, and thus, the device efficiency and life of the device are thought to be improved, because the charge balance of holes and electrons is improved through the control of a charge injection rate.

The monoamine compound according to an embodiment of the present disclosure is used in a hole transport region and contributes to the decrease of a driving voltage and the increase of the efficiency and life of an organic electroluminescence device.

The organic electroluminescence device according to an embodiment of the present disclosure has excellent efficiency.

The monoamine compound according to an embodiment of the present disclosure may be used as a material for a hole transport region of an organic electroluminescence device, and by using the monoamine compound, the improving of the efficiency of the organic electroluminescence device may be achieved.

The terminology used herein is for the purpose of describing particular embodiments only and is not intended to be limiting of the present disclosure. As used herein, the singular forms "a" and "an" are intended to include the plural forms as well, unless the context clearly indicates otherwise. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although exemplary embodiments of the present disclosure have been described, it is understood that the present disclosure should not be limited to these exemplary embodiments but various changes and modifications can be made by one ordinary skilled in the art within the spirit and scope of the appended claims, and equivalents thereof.

What is claimed is:

1. A compound, represented by the following Formula 1:

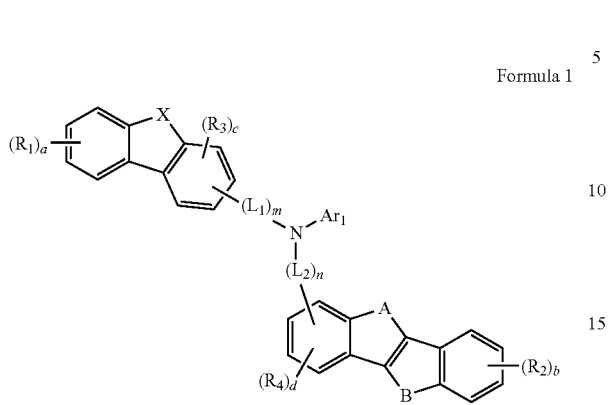

Formula 1 in Formula 1,

X is $NAr_2$, S, or O,

A and B are each independently O or S, $Ar_1$ and $Ar_2$ are each independently a substituted or unsubstituted aryl group of 6 to 30 carbon atoms for forming a ring, or a substituted or unsubstituted heteroaryl group of 2 to 30 carbon atoms for forming a ring, $R_1$ to $R_4$ are each independently a hydrogen atom, a deuterium atom, a halogen atom, a cyano group, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, $L_1$ and $L_2$ are each independently direct linkages, substituted or unsubstituted arylene groups of 6 to 30 carbon atoms for forming a ring, or substituted or unsubstituted heteroarylene groups of 2 to 30 carbon atoms for forming a ring, except when both $L_1$ and $L_2$ are direct linkages, "a" and "b" are each independently integers of 0 to 4, "c" and "d" are each independently integers of 0 to 3, and "m" and "n" are each independently integers of 0 to 2.

2. The compound of claim 1, wherein Formula 1 is represented by the following Formula 2 or Formula 3:

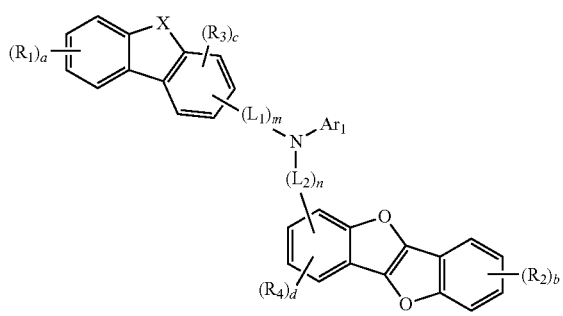

Formula 2

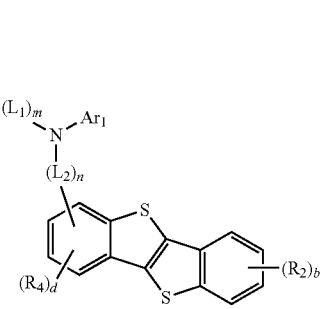

Formula 3 in Formula 2 and Formula 3,

X, $Ar_1$, $R_1$ to $R_4$, $L_1$, $L_2$, "a" to "d", "m" and "n" are the same as defined with respect to Formula 1.

3. The compound of claim 1, wherein Formula 1 is represented by the following Formula 4 or Formula 5:

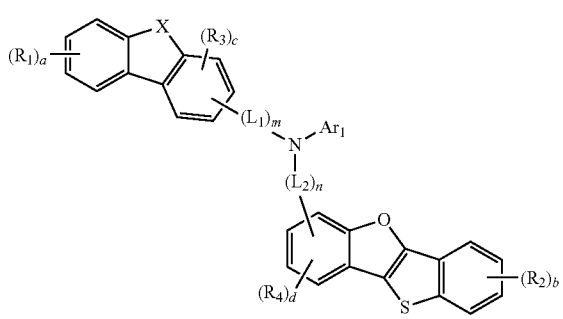

Formula 4

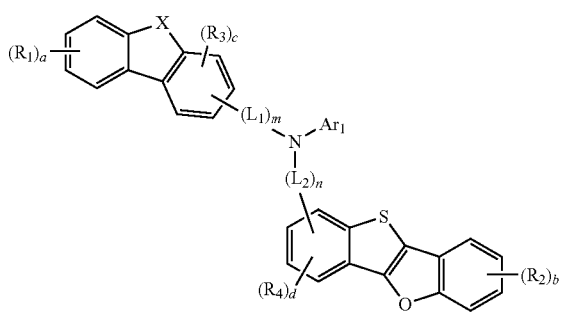

Formula 5 in Formula 4 and Formula 5,

X, $Ar_1$, $R_1$ to $R_4$, $L_1$, $L_2$, "a" to "d", "m" and "n" are the same as defined with respect to Formula 1.

4. The compound of claim 1, wherein:

"m" and "n" are each independently 0 or 1, and $L_1$ and $L_2$ are each independently a direct linkage or a substituted or unsubstituted arylene group of 6 to 12 carbon atoms for forming a ring.

5. The compound of claim 1, wherein $Ar_1$ is a substituted or unsubstituted aryl group of 6 to 18 carbon atoms for forming a ring.

6. The compound of claim 1, wherein Formula 1 is represented by the following Formula 6:

Formula 6

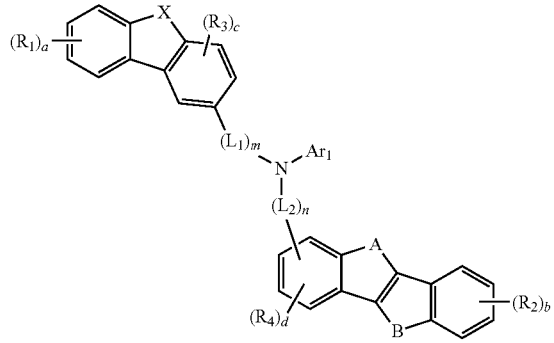

in Formula 6,

X, A, B, Ar$_1$, R$_1$ to R$_4$, L$_1$, L$_2$, "a" to "d", "m" and "n" are the same as defined with respect to Formula 1.

7. The compound of claim 1, wherein R$_1$ to R$_4$ are each independently a hydrogen atom, a deuterium atom, a halogen atom, a cyano group, a substituted or unsubstituted alkyl group of 1 to 20 carbon atoms, or an unsubstituted aryl group of 6 to 30 carbon atoms for forming a ring.

8. The compound of claim 1, wherein the compound represented by Formula 1 is at least one selected from compounds represented in the following Compound Group 1:

Compound Group 1

1

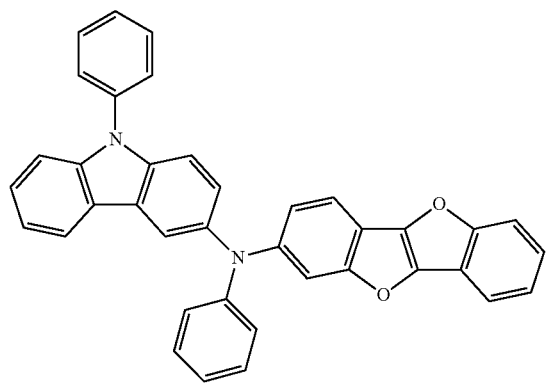

2

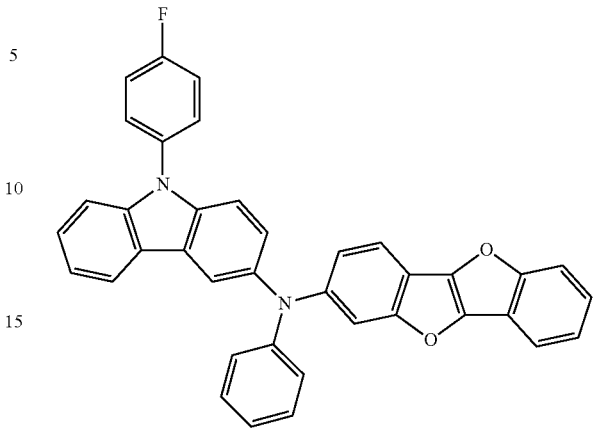

3

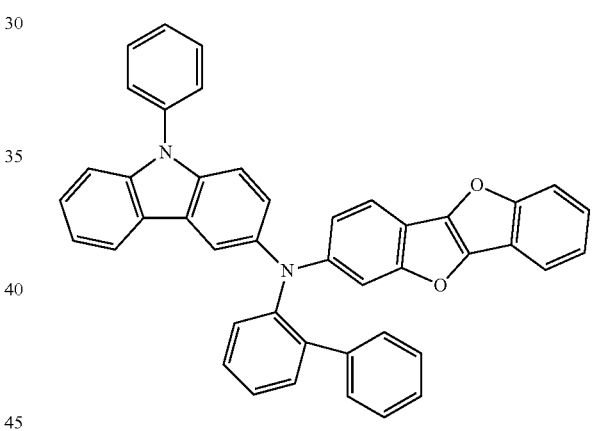

4

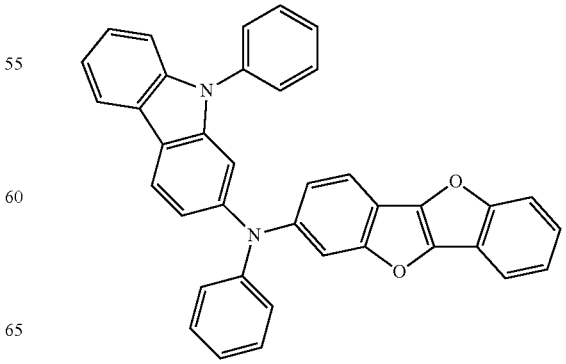

5
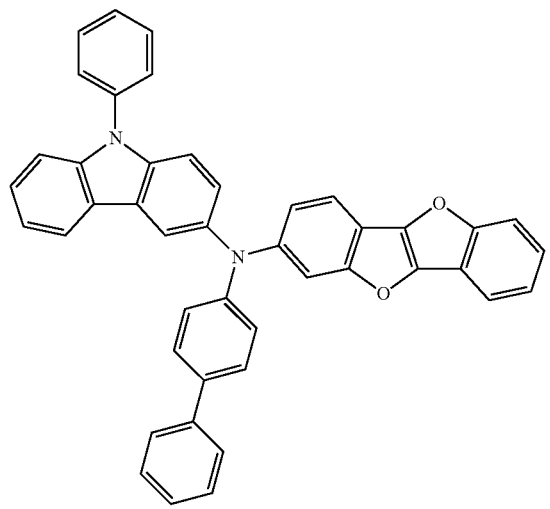
6
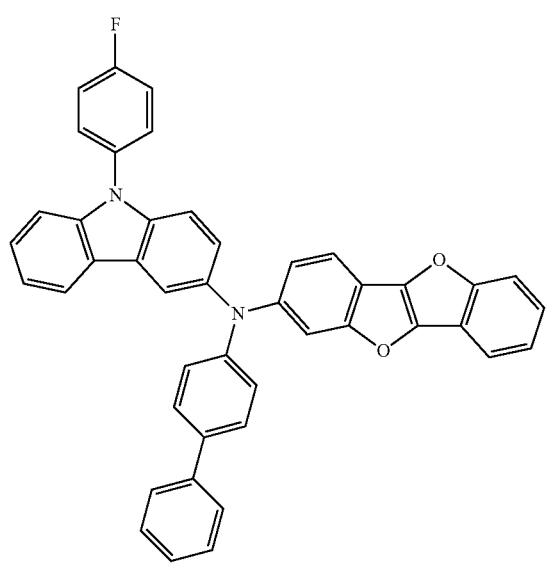
7
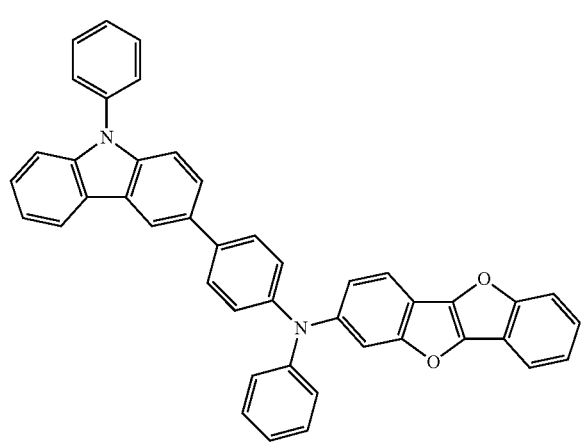
8
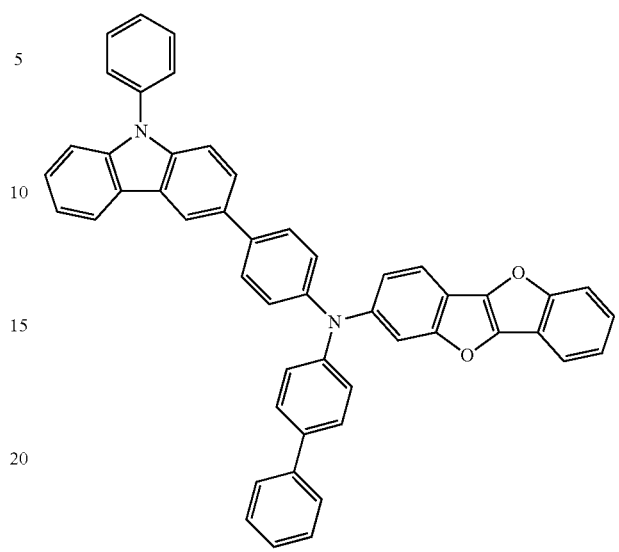
9
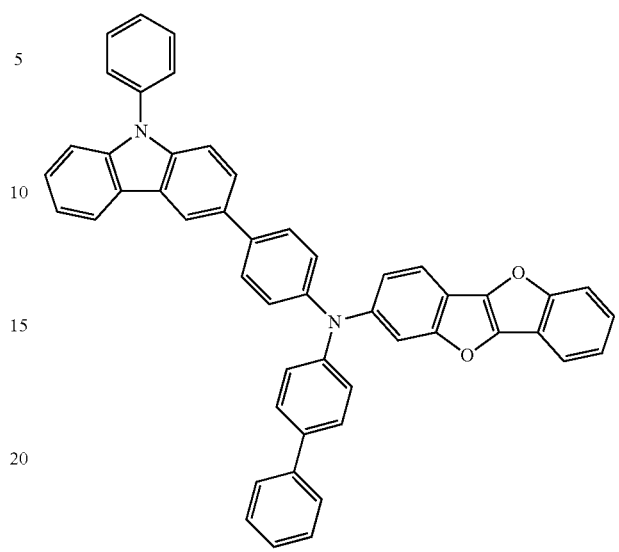
10
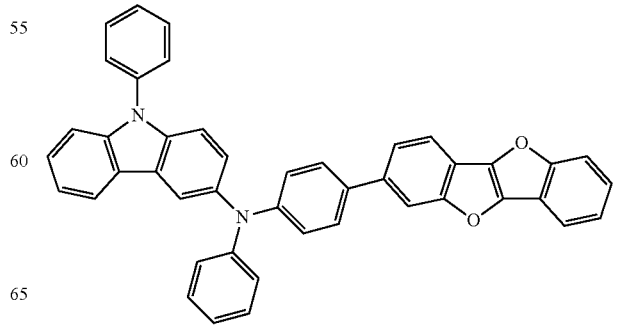

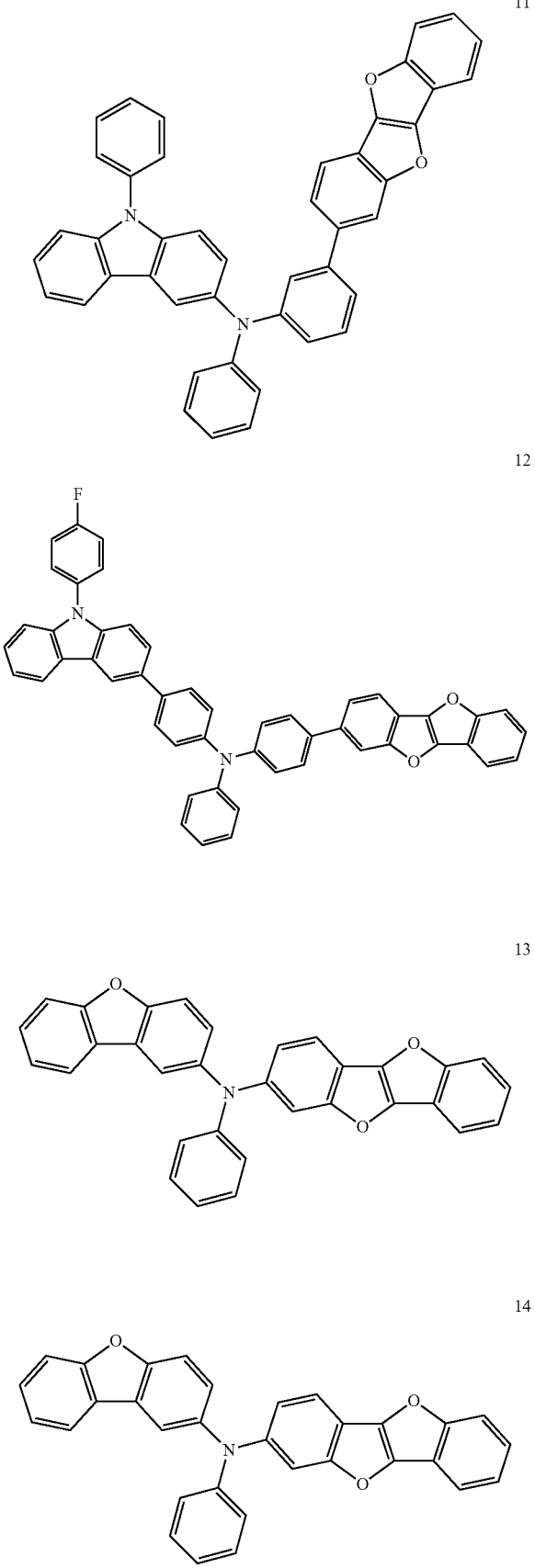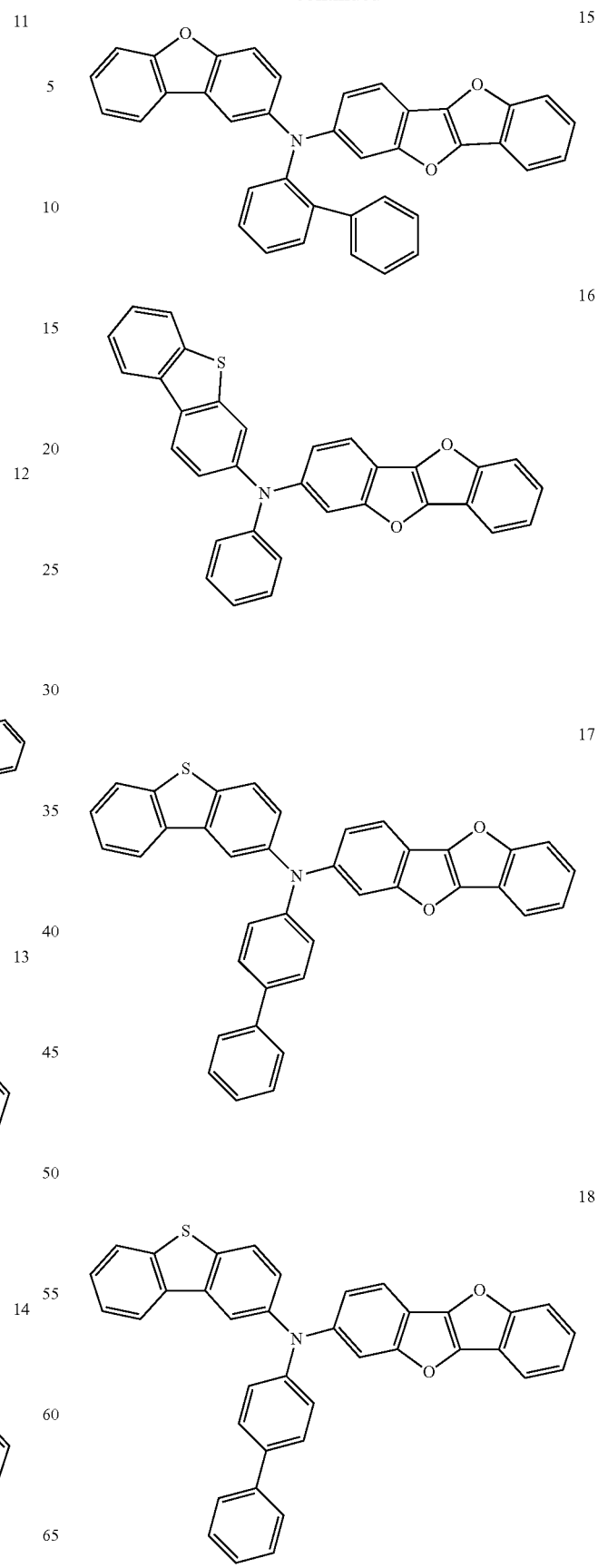

19
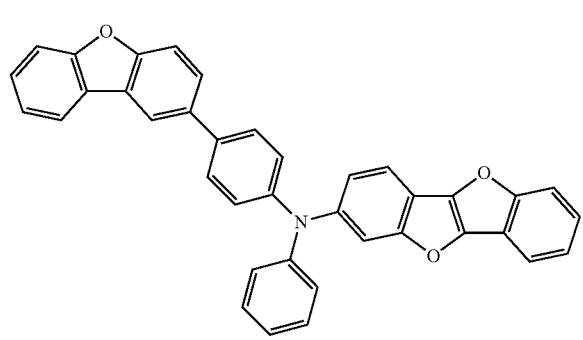
20
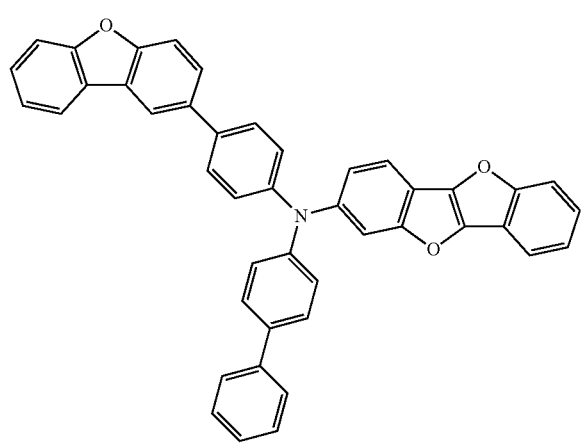
21
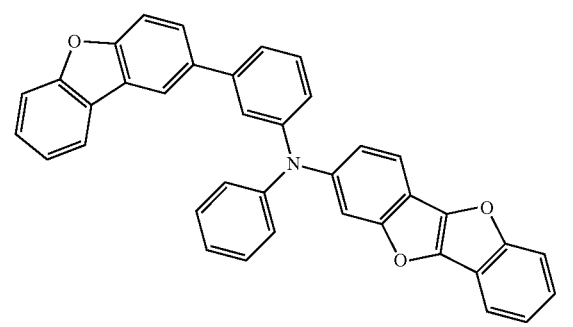
22
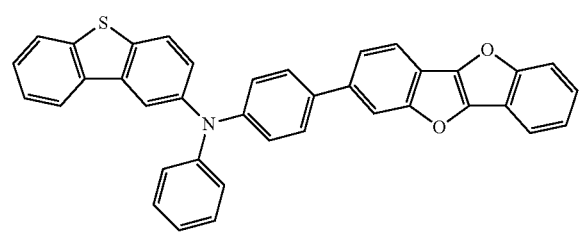
23
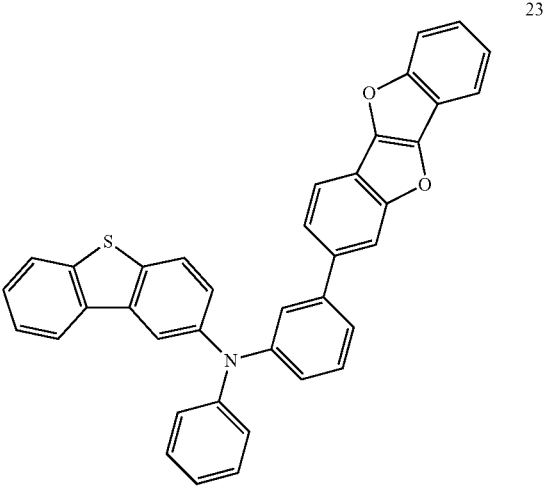
24
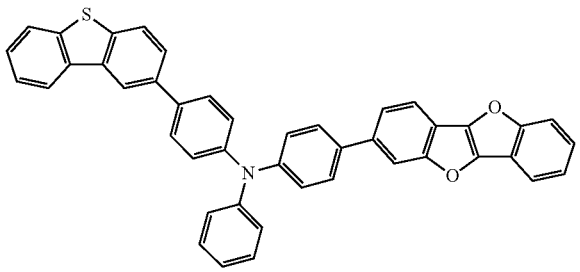
25
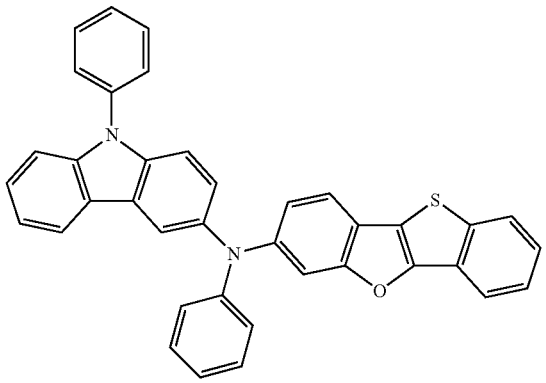
26
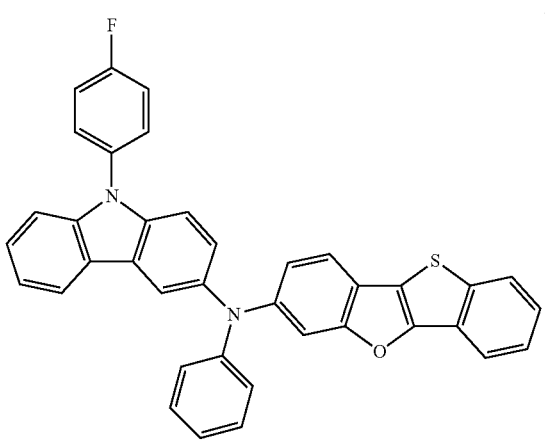

27
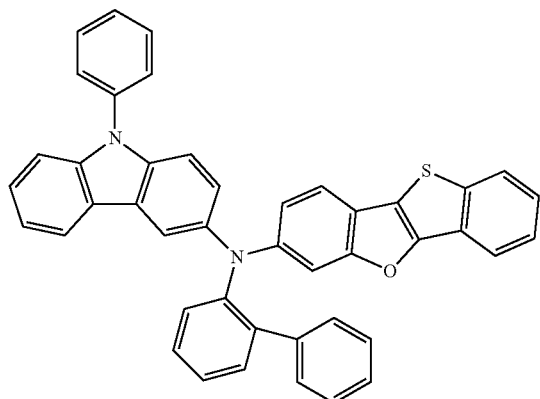
28
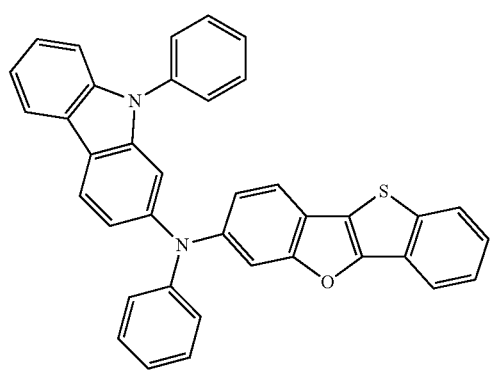
29
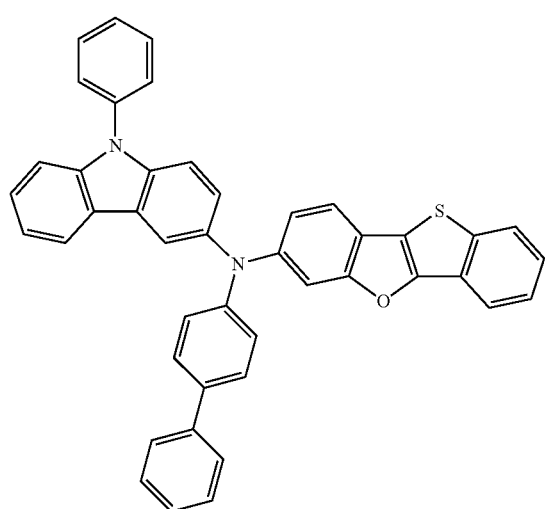
30
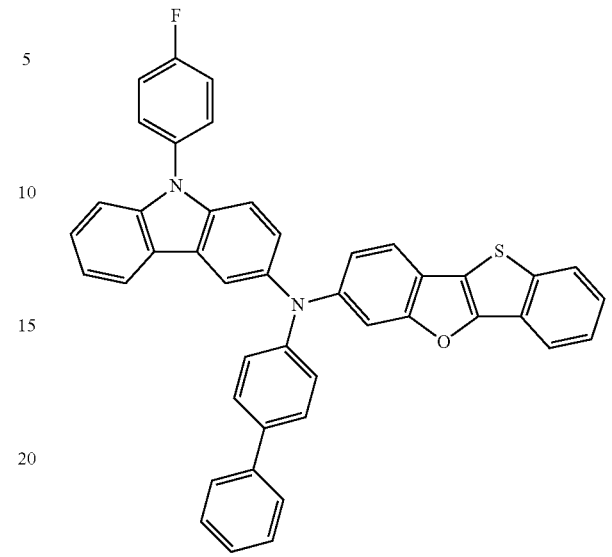
31
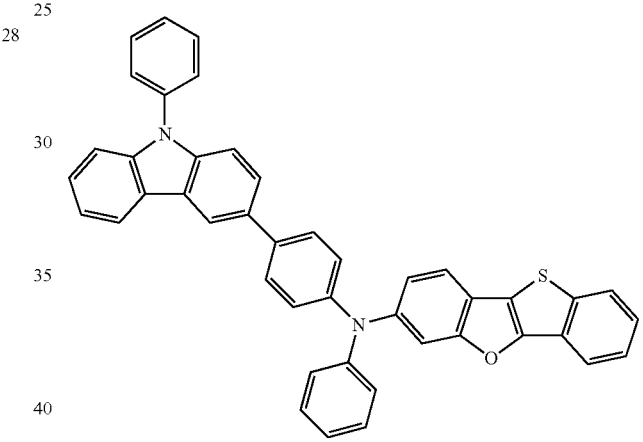
32
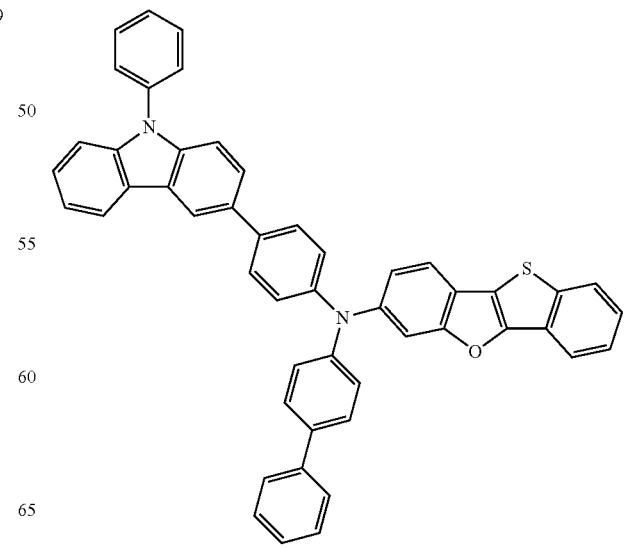

33
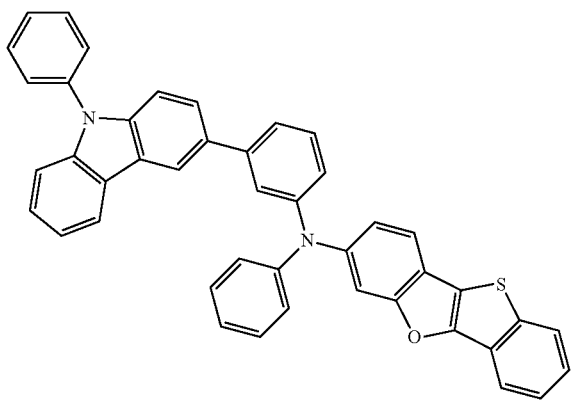
34
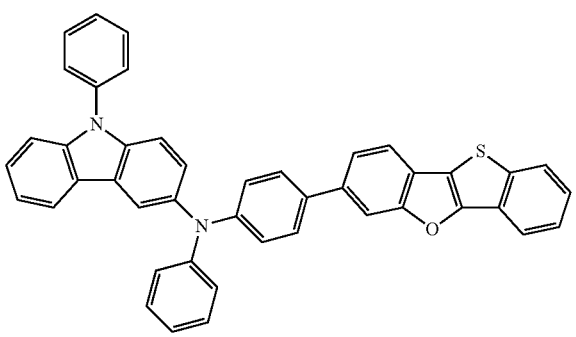
35
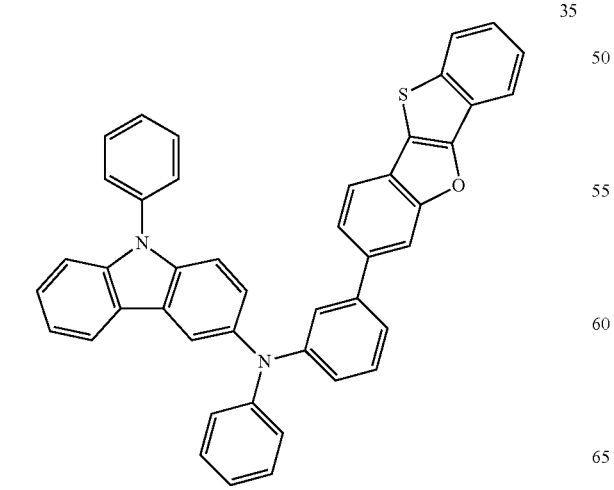
36
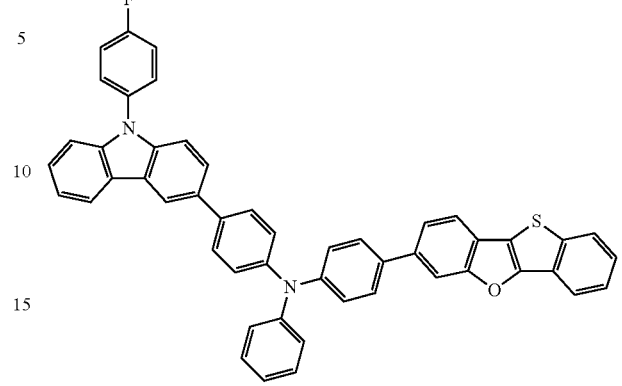
37
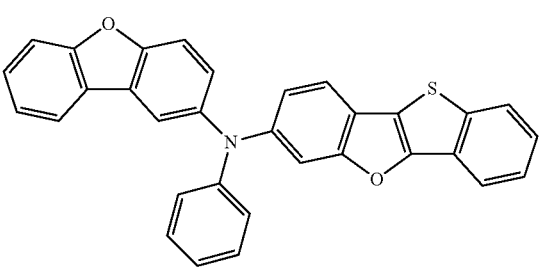
38
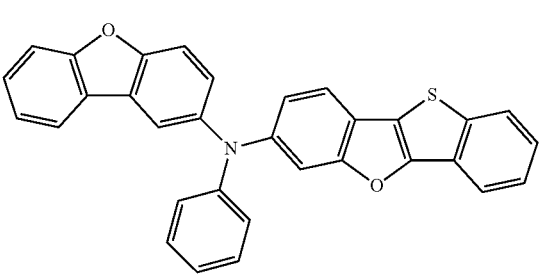
39
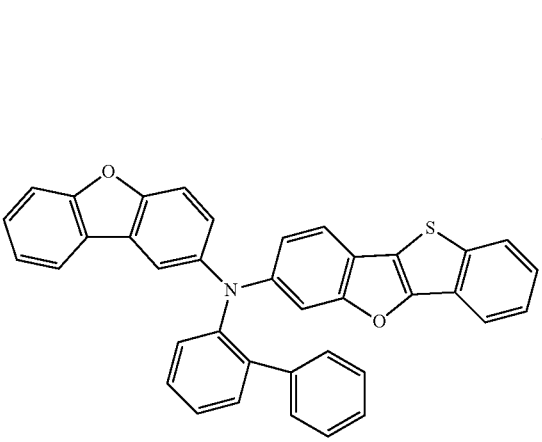

40
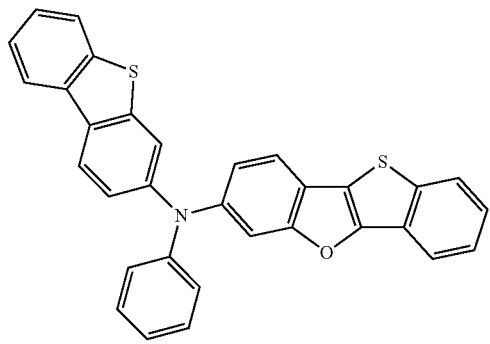
41
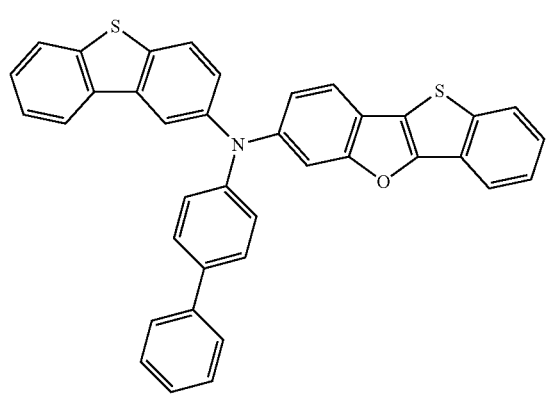
42
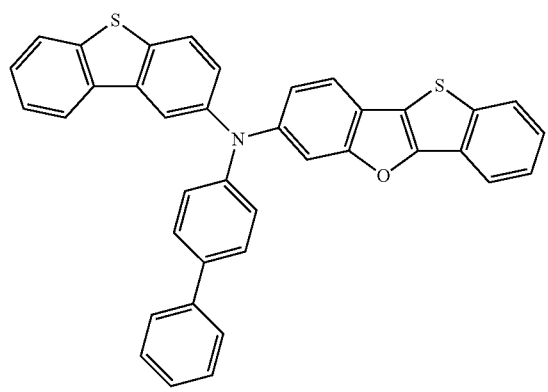
43
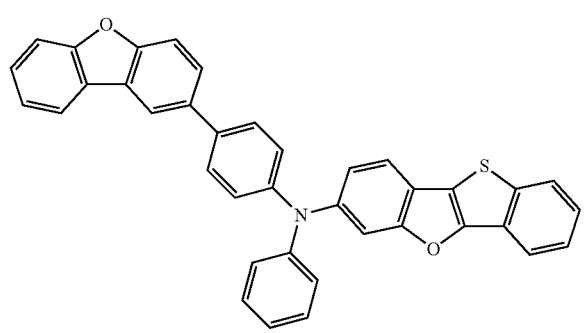
44
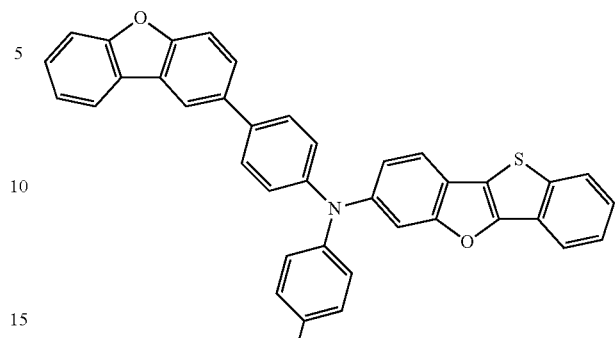
45
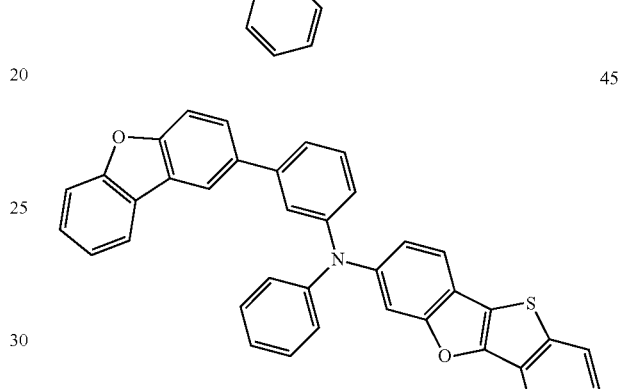
46
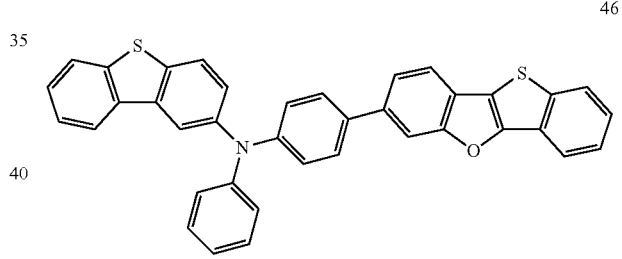
47
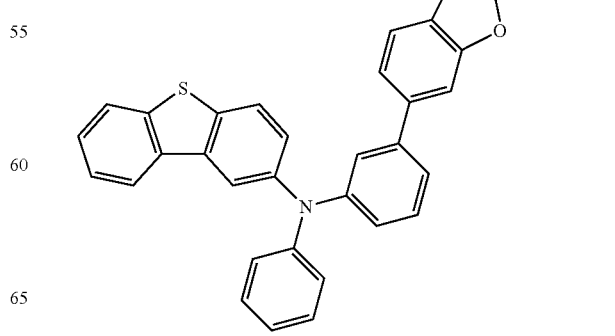

48
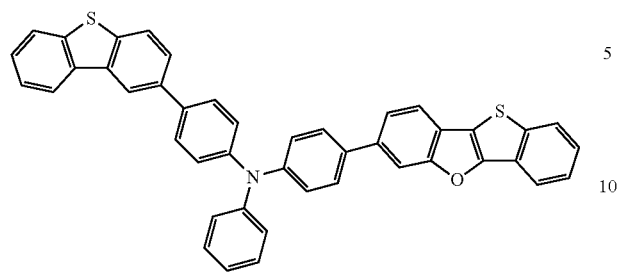
49
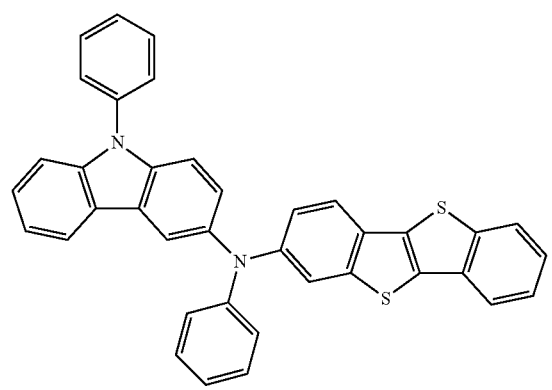
50
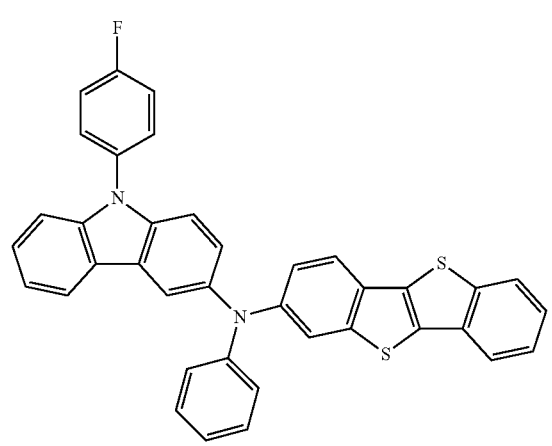
51
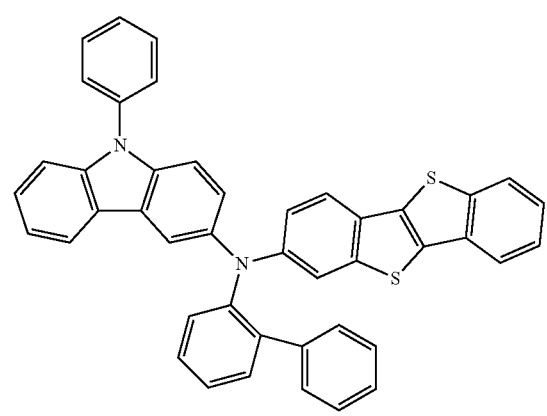
52
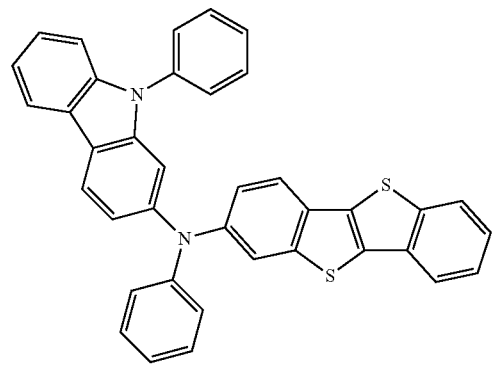
53
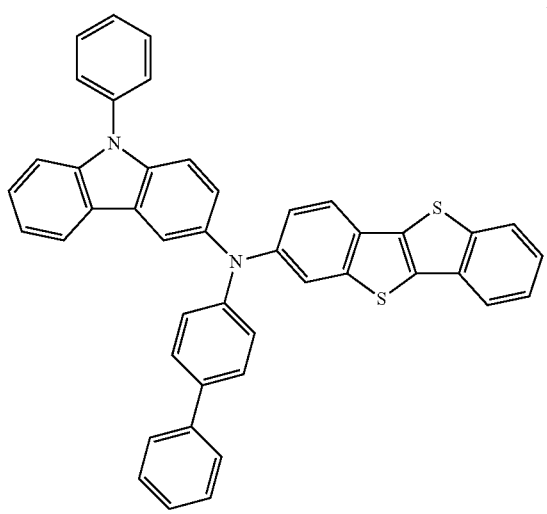
54
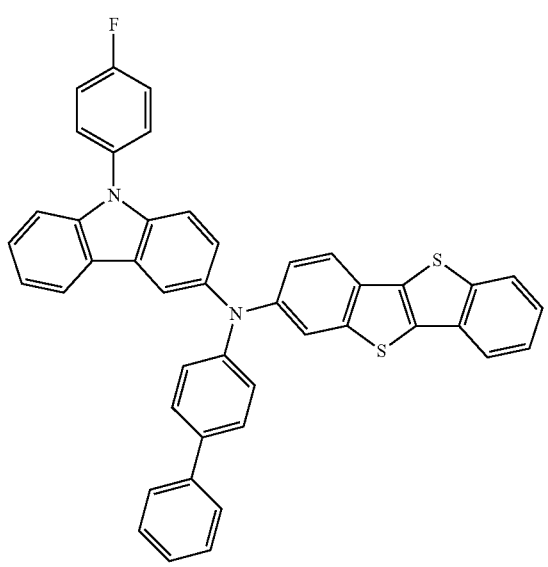

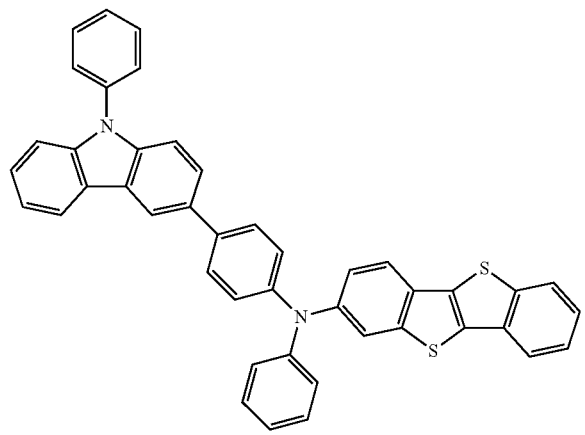
55
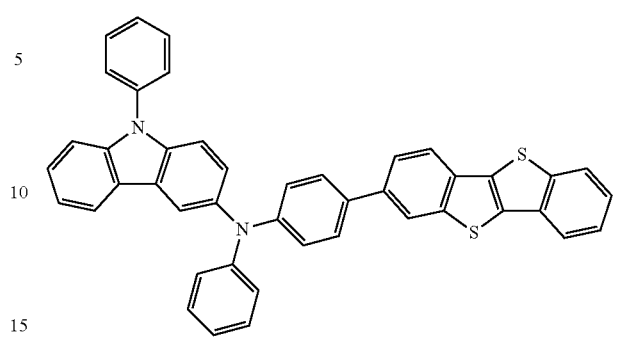
58
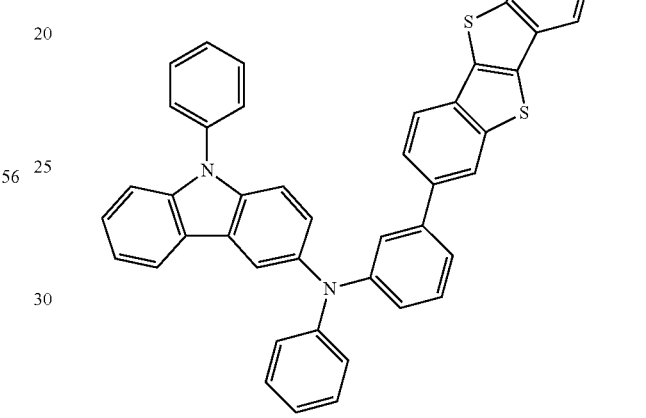
59
56
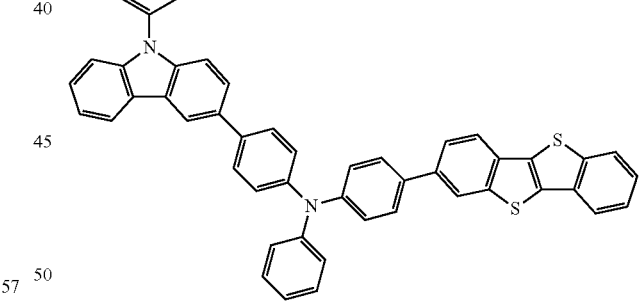
60
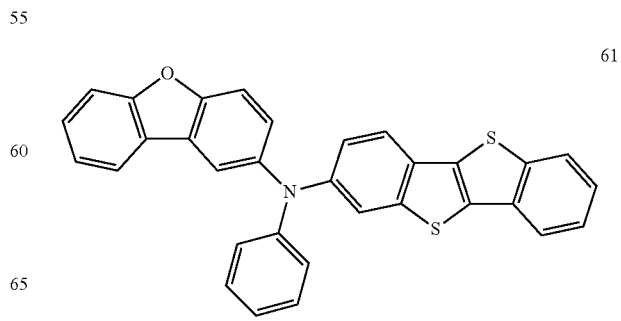
57
61

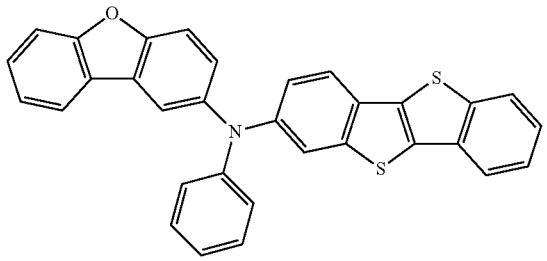
62
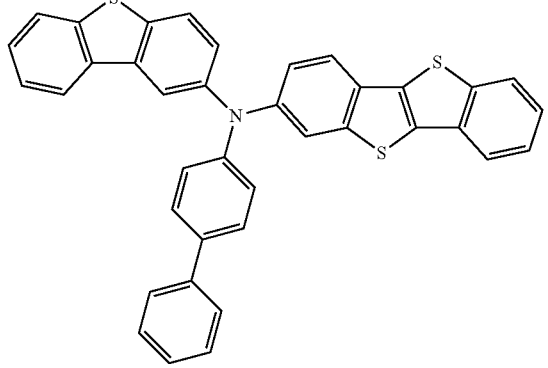
66
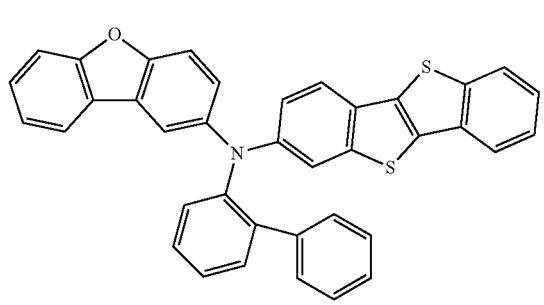
63
67
68
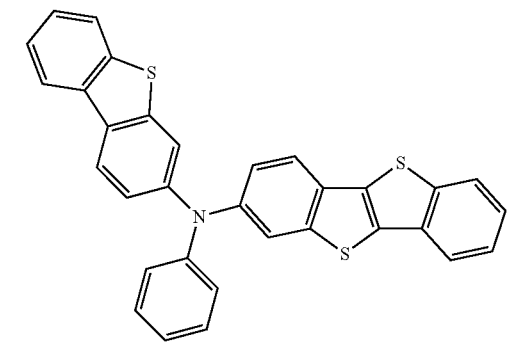
64
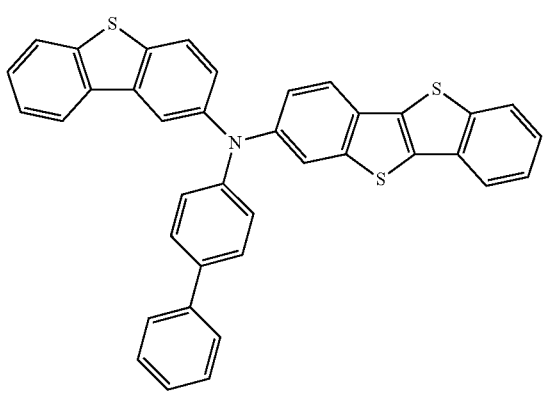
65
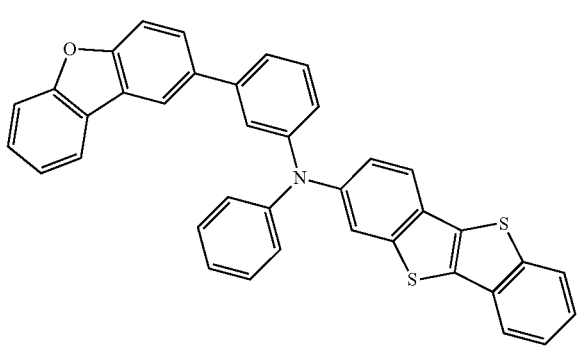
69

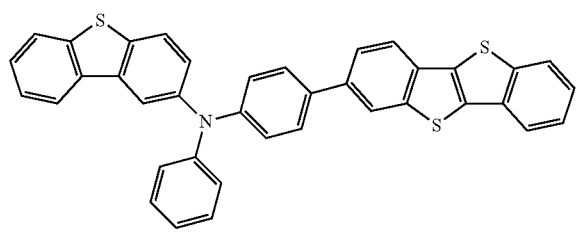
70
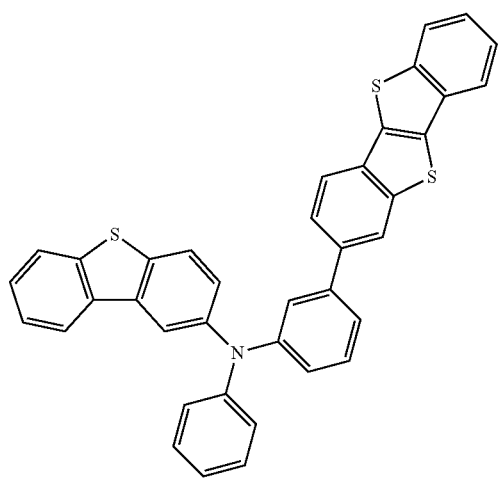
71
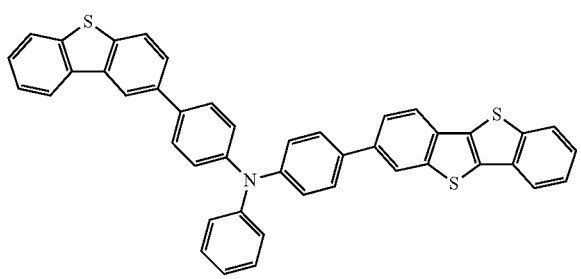
72
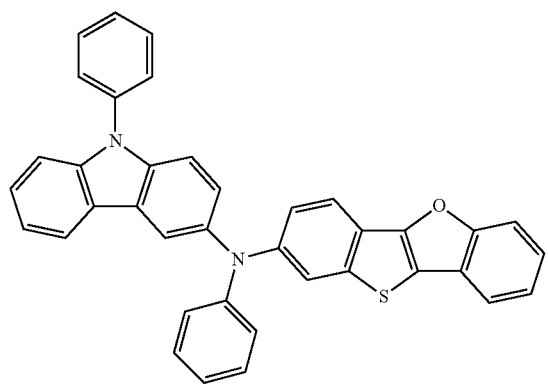
73
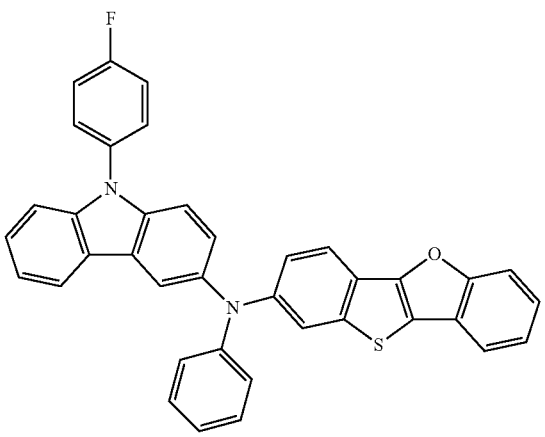
74
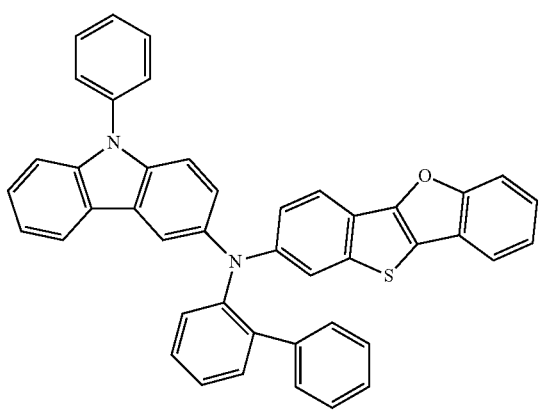
75
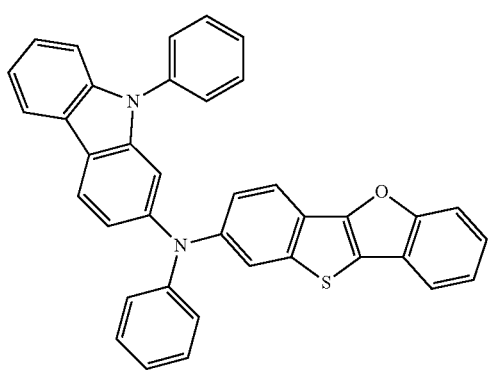
76

77
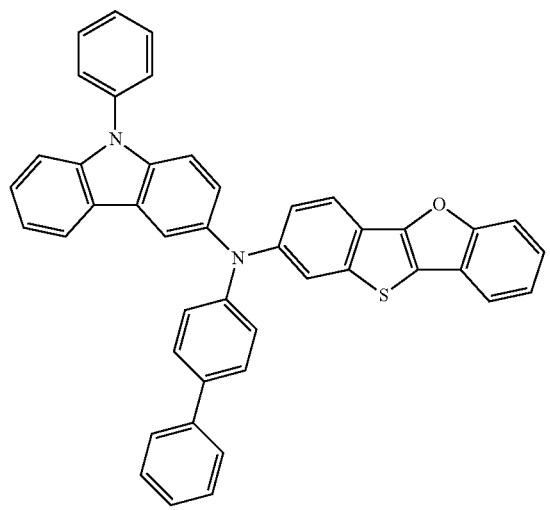
78
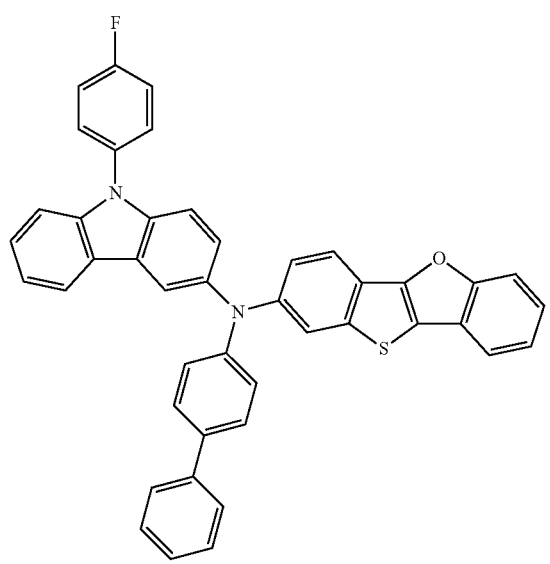
79
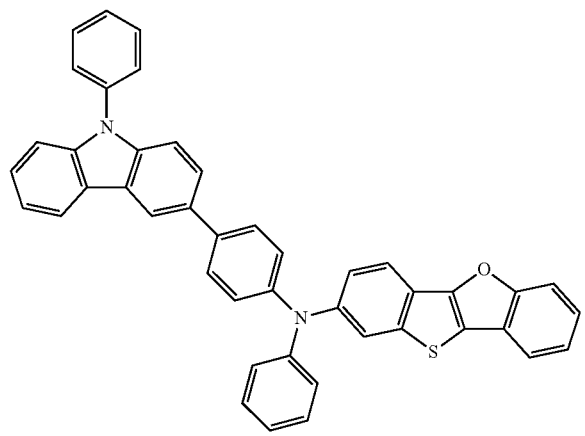
80
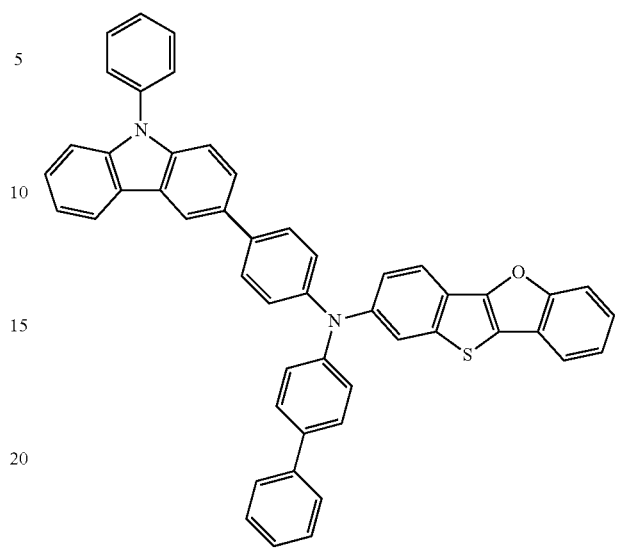
81
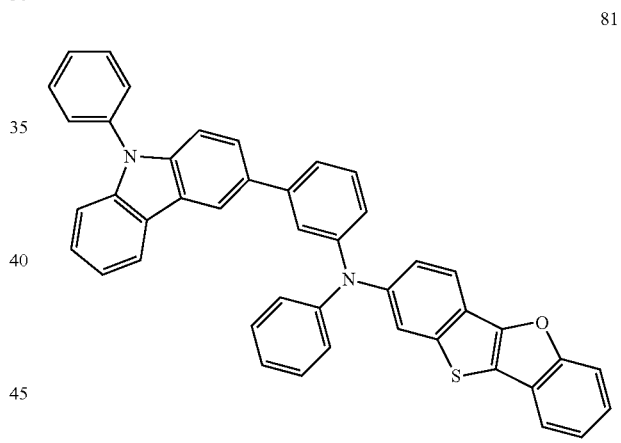
82
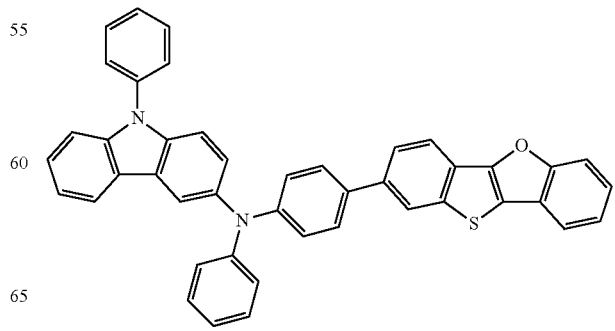

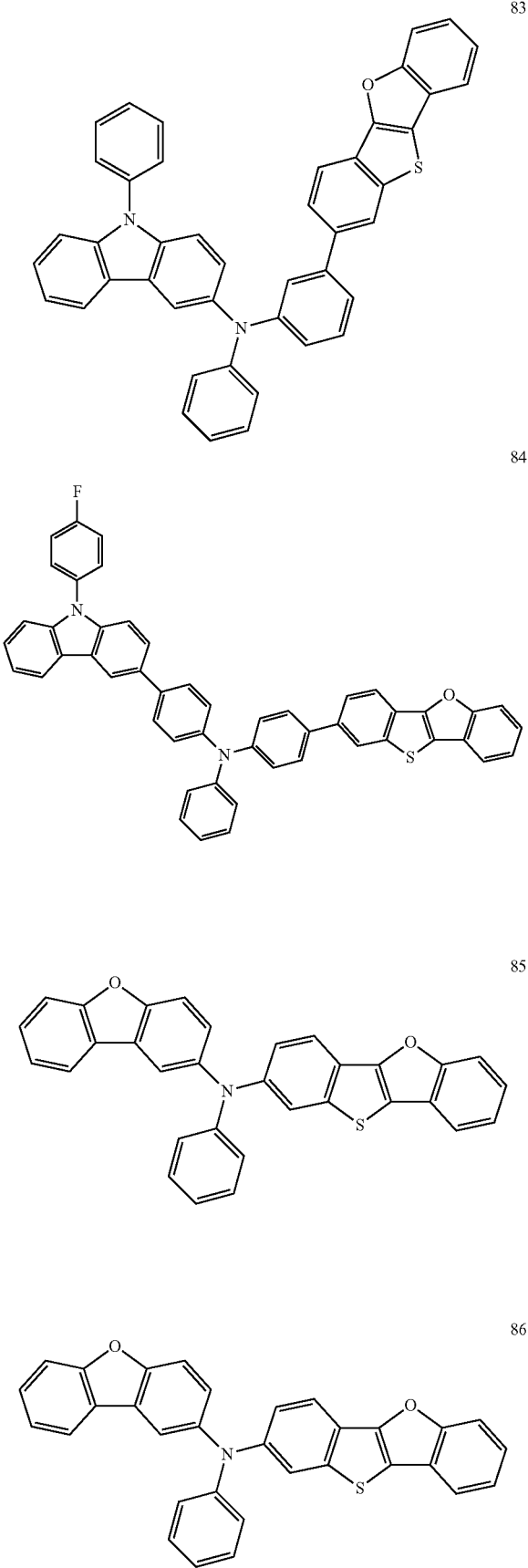
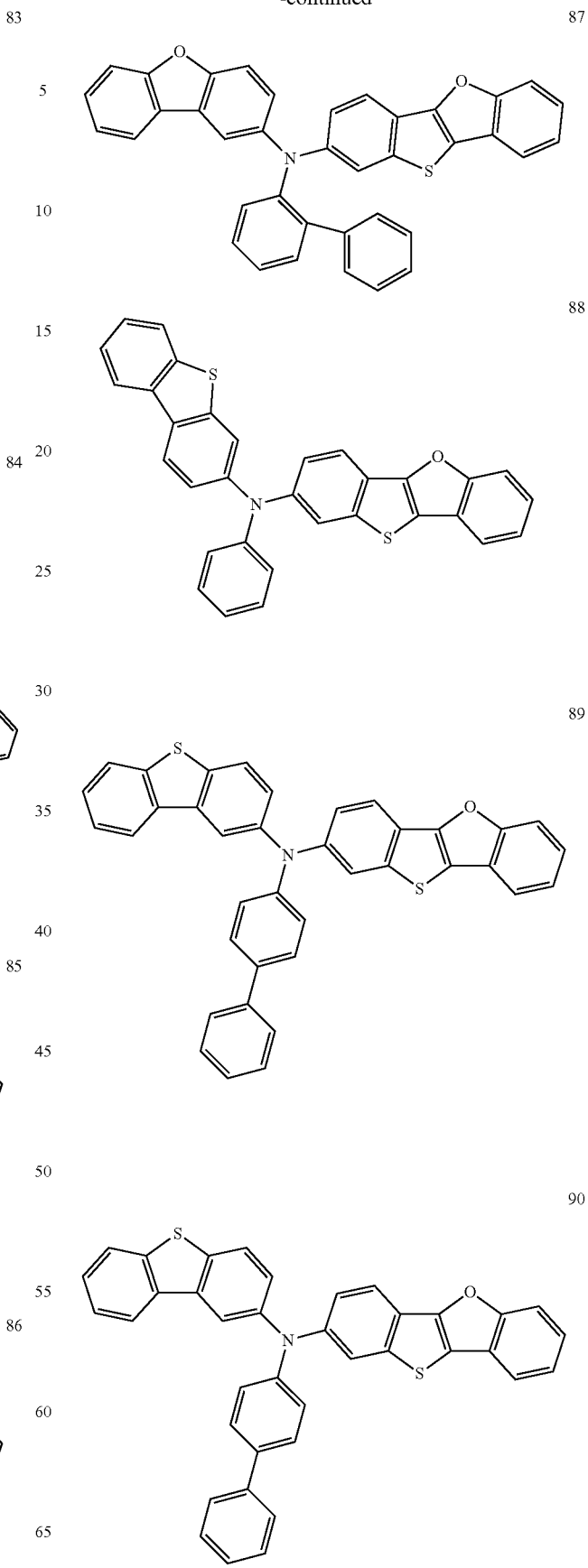

91
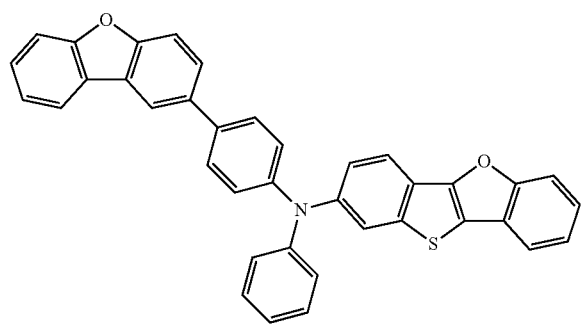
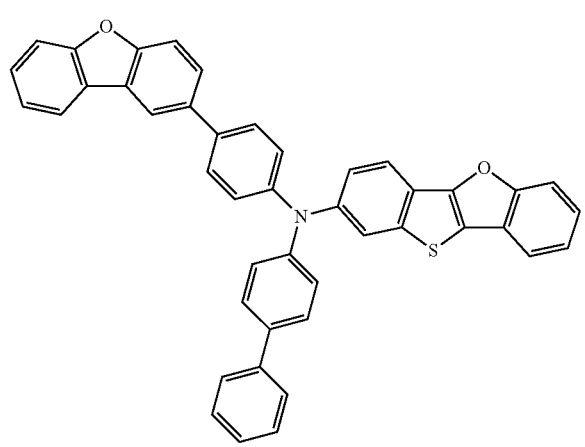
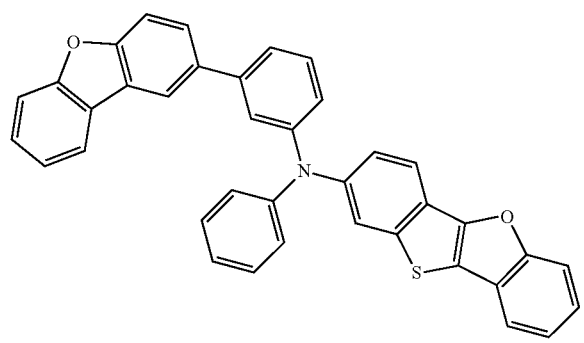
92
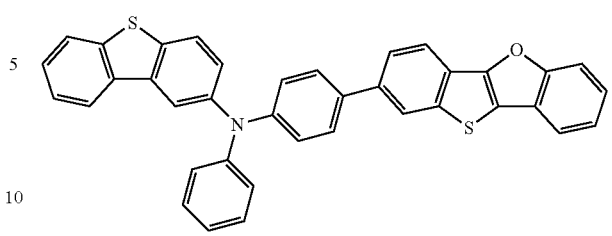
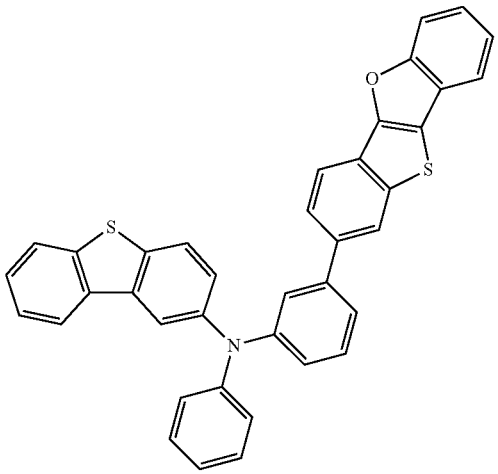
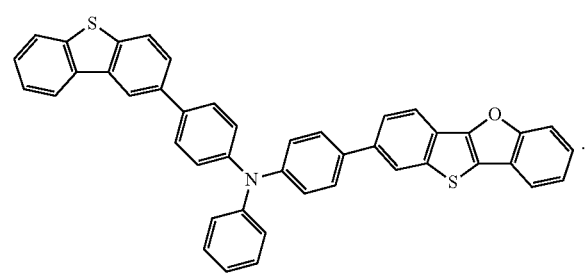
* * * * *